(12) United States Patent
Swager et al.

(10) Patent No.: US 7,700,366 B2
(45) Date of Patent: Apr. 20, 2010

(54) FLUORESCENT, SEMI-CONDUCTIVE POLYMERS, AND DEVICES COMPRISING THEM

(75) Inventors: Timothy M. Swager, Newton, MA (US); Youngmi Kim, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 1285 days.

(21) Appl. No.: 11/005,634

(22) Filed: Dec. 6, 2004

(65) Prior Publication Data

US 2005/0196775 A1 Sep. 8, 2005

Related U.S. Application Data

(60) Provisional application No. 60/526,886, filed on Dec. 4, 2003.

(51) Int. Cl.
*G01N 21/76* (2006.01)
(52) U.S. Cl. .................................................. 436/172
(58) Field of Classification Search .................. 436/72
See application file for complete search history.

(56) References Cited

U.S. PATENT DOCUMENTS 5,514,878 A 5/1996 Holmes et al.

FOREIGN PATENT DOCUMENTS

| GB | 2303633 A | 2/1997 |
| WO | WO 96/10617 | 4/1996 |
| WO | WO 9957222 A1 * | 11/1999 |

OTHER PUBLICATIONS

Yang, J.-S. et al., "Fluorescent Porous Polymer Films as TNT Chemosensors: Electronic and Structural Effects", *J. Am. Chem. Soc.*, 120:11864-11873 (1998).
International Search Report (Form PCT/ISA/210) mailed Sep. 22, 2005.

* cited by examiner

*Primary Examiner*—Walter D Griffin
*Assistant Examiner*—Bobby Ramdhanie
(74) *Attorney, Agent, or Firm*—Foley Hoag LLP

(57) ABSTRACT

The present invention relates to fluorescent, semiconductive polymers comprising electron withdrawing groups bonded to the polymer. The invention also relates to a method of detecting analytes comprising contacting the analyte with the fluorescent, semiconductive polymers of the present invention. The invention also relates to light emitting devices, photovoltaic devices, and sensors comprising the fluorescent, semiconductive polymers of the present invention.

41 Claims, 15 Drawing Sheets

FLUORESCENT, SEMI-CONDUCTIVE POLYMERS, AND DEVICES COMPRISING THEM

RELATED APPLICATIONS

This application claims the benefit of priority to U.S. Provisional Application Ser. No. 60/526,886, filed Dec. 4, 2003; the specification of which is hereby incorporated in its entirety.

GOVERNMENT SUPPORT

This invention was made with support provided by the U.S. Army through the Institute for Soldier Nanotechnologies, under Contract DAAD-19-02-D-0002 with the U.S. Army Research Office; the government, therefore, has certain rights in the invention.

BACKGROUND OF THE INVENTION

Poly(p-phenylene vinylene) (PPV) and its derivatives are among the most extensively studied organic semiconductive polymers. In spite of their processablity, high luminescence, and structural diversity, several challenges remain for further applications. As in many conjugated polymers (CPs), the fluorescence quantum yields of PPVs are substantially lower in the solid state due to interchain interactions. (a) Osaheni, J. A.; Jenekhe, S. A. *J. Am. Chem. Soc.* 1995, 117, 7389-7398. (b) Winnik, F. M. *Chem. Rev.* 1993, 93, 587-614. (c) An, B.-K.; Kwon, S.-K.; Jung, S.-D.; Park, S. Y. *J. Am. Chem. Soc.* 2002, 124, 14410-14415. Successful approaches to enhance the solid state emission efficiency of CPs include the incorporation of bulky side chains or rigid three-dimensional moieties. (a) Jakubiak, R.; Collison, C. J.; Wan, W. C.; Rothberg, L. J.; Hsieh, B. R. *J. Phys. Chem. A.* 1999; 103, 2394-2398. (b) Yang, J.-S.; Swager, T. M. *J. Am. Chem. Soc.* 1998, 120, 11864-11873. Another key issue to be addressed is the tuning of the electron affinity of CPs in order to control their work functions and charge transporting properties. Kraft, A.; Grimsdale, A. C.; Holmes, A. B. *Angew. Chem. Int. Ed.* 1998, 37, 402-428. Traditionally, atoms with lone pair electrons capable of electron donating or electron withdrawing groups (EWGs) connected directly to the π-system have been utilized to modify their electron affinity. (a) Hörhold, H.-H.; Helbig, M. *Makromol. Chem., Macromol. Symp.* 1987, 12, 229-258. (b) Leuze, M.; Hohloch, M.; Hanack, M. *Chem. Mater.* 2002, 14, 3339-3342. Direct attachment of EWGs can produce large effects and such polymers are also disclosed presently. Steric repulsion of bulky substituents at the phenylene or vinylene subunits, however, often induce deviations from planarity and decrease conjugation.

The fluorescent, semiconductive polymers of the present invention can be used in such applications as light emitting devices (LEDs). Recently, there has been reported an organic electroluminescence device (organic EL device) having a double-layer structure in which an organic fluorescent dye as a light-emitting layer is laminated with an organic charge transport compound used in photosensitive layer for electrophotography and the like. Japanese Patent Application Laid-Open (JP-A) No. 59-194393. Because organic EL devices with colored light emissions are obtained easily and have low voltage driving and high luminance as compared to inorganic EL devices, there have been reported trials regarding device structures, organic fluorescent dyes and organic charge transport compounds of organic EL devices. Jpn. J. Appl. Phys., 27, L269 (1988), J. Appl. Phys., 1989, 65, 3610.

Apart from organic EL devices using mainly organic compounds having a lower molecular weight, polymer LEDs using light-emitting materials having a higher molecular weight have been proposed. WO 9013148 published specification; JP-A No. 3-244630; Appl. Phys. Lett., 1991, 58, 1982. WO9013148 discloses in the Examples an EL device using a thin film of poly(p-phenylene vinylene) obtained by forming a film of a soluble precursor on the electrode and subjecting it to a heat treatment to convert the precursor into a conjugated polymer.

Further, JP-A 3-244630 has exemplified conjugated polymers soluble in a solvent and needing no heat treatment. Also, a polymeric light-emitting material soluble in a solvent and a polymer LED using the same has been reported. Appl. Phys. Lett., 1991, 58, 1982.

Soluble, fluorescent polymers are advantageous for forming films having large areas at reduced cost since the organic layer can easily be formed by coating methods, as compared to vapor deposition of low molecular weight materials. The mechanical strength of the resulting film is believed to be greater due to the higher molecular weight of the fluorescent polymers.

Conventionally, in addition to the above-described poly(p-phenylene vinylene), there have been reported polyfluorene, poly p-phenylene derivative and the like, as the light-emitting materials used in these polymeric LEDs. Jpn. J. Appl. Phys., 1991, 30, L1941; Adv. Mater., 1992, 4, 36.

In order to utilize the film-formable characteristics of a polymeric fluorescent substance by coating, there is needed polymeric fluorescent substances having excellent solubility in organic solvents. To realize the practical flat panel display, there is needed a polymer LED having high efficiency and long lifetime.

One object of the present invention is to provide fluorescent, semiconductive polymers having increased solubility in organic solvents, enhanced photochemical and thermal stability, and a polymer LED having high performance which can be driven at higher efficiency and longer lifetime using the fluorescent, semiconductive polymer.

Another application of the fluorescent, semiconductive polymers of the present invention is sensors, in particular, biosensors. Recent developments in the world political situation, exemplified by the disintegration of the Soviet Union, continued geopolitical pressures in the Middle East and Eastern Europe and the proliferation of terrorist activities throughout the world, have raised increased concerns about the use of chemical and biological warfare materials in local conflicts. The defense against chemical and biological warfare agents includes detection of potential threats, development and use of protective equipment, development of vaccination post-exposure prophylaxis measures and fabrication of structures providing barriers to the toxic agents which are suitable for decontamination procedures. Threat identification is imperative prior to engagement, during battle and after battle during decontamination procedures. In addition, chemical sensors for detecting chemical warfare materials are needed for treaty verification, demilitarization, environmental monitoring and characterization of materials acting as barriers to agent diffusion.

Existing methods of detection have proven inadequate. Existing methods for long-range threat identification, such as light detection and ranging (LIDAR), and for laboratory analysis of chemical warfare agents using gas chromatography to provide a chemical agent monitor (miniCAMS), light addressable potentiometric sensor (LAPS) or ion mobility sensor (IMS) technology, have all proven slow and cumbersome to carry out. A need exists for lightweight, high-sensitivity sensors having rapid response times.

Existing sensors have proven capable of meeting the requirements of several applications, but no sensor has provided the combined sensitivity and speed of response needed for each application. Needs exist for field-usable chemical and biological sensors for the detection of vapor and liquid dispersed chemical warfare agents, toxins of biological origin and aerosol dispersed pathogenic microorganisms. Existing instrumentation used in identifying chemical warfare agents rely on ion mobility spectroscopy or gas chromatography for detection. The Advanced Chemical Agent Detection/Alarm System (ACADA) uses ion-mobility spectroscopy to achieve sensitivities to Sarin and Soman on the order of 1 mg/m$^3$ (170 parts per billion (ppb)) in ten seconds and 0.1 mg/m$^3$ (17 ppb) in 30 seconds. In addition to the system's slow response and low sensitivity, the size and weight characteristics of the ACADA system (one cubic foot in volume and 25 pounds in weight) reduces the applicability of the system for distributed sensing or remote sensing applications. Sensors such as the miniCAMS system provide unparalleled sensitivity but require preconcentration times on the order of minutes. That response time is unsuitable for rapid detection of conditions that are immediately dangerous to life and health. Other existing methods use acoustic or optical/electrochemical methods of detection, such as surface acoustic wave (SAW)-based instruments and light addressable potentiometric sensors (LAPS). Neither method has proven effective in meeting the sensitivity and response times required. At best, the SAW instrument has demonstrated sensitivities to Sarin/Soman at 0.01 mg/m$^3$ (1.7 ppb), but requires preconcentration times ranging from 2 minutes to 14 minutes. Needs exist for field-usable sensors that provide for highly-sensitive, rapid response measurements of the concentration of analytes in solution or in air.

The need still exists for stable, soluble, fluorescent, semiconductive polymers with unique electronic properties to meet the demands of the various applications described above.

SUMMARY OF THE INVENTION

The present invention relates to fluorescent, semiconductive polymers that are thermally, photochemically, and chemically stable in thin films and soluble in organic solvents. These fluorescent polymers comprise a conjugated backbone and use electron withdrawing groups (EWGs) to affect the electron affinity of the polymers.

In one embodiment the present invention relates to a fluorescent, semiconductive polymer comprising a conjugated backbone and electron withdrawing groups bonded to the polymer. The fluorescent, semiconductive polymers may comprise one or both types of EWGs; i.e., portions where the EWG is directly bonded to the conjugated backbone and portions where the EWG is not bonded directly to the conjugated backbone.

In a further embodiment, the fluorescent, semiconductive polymer is soluble in an organic solvent. In a further embodiment the electron withdrawing groups of the fluorescent, semiconductive polymer are not bonded directly to the conjugated backbone and the flurorescent, semiconductive polymer has a hyperconjugated 3-D structure. In a further embodiment, the electron withdrawing groups of the fluorescent, semiconductive polymer are directly bonded to the conjugated backbone. In a further embodiment, the fluorescent, semiconductive polymer comprises a moiety where the electron withdrawing group is not bonded directly to the conjugated backbone, and a moiety where the electron withdrawing group is bonded directly to the conjugated backbone.

In a further embodiment, the electron withdrawing groups of the fluorescent, semiconductive polymer are selected from the group consisting of esters, perhalogenated alkyls, perhalogenated aryls, nitriles, or electron deficient heteroaryls. In a further embodiment, the electron withdrawing groups of the fluorescent, semiconductive polymer are perfluorinated alkyls. In a further embodiment, the perfluorinated alkyls are perfluorinated $C_1$-$C_{12}$ alkyls. In a further embodiment, the perfluorinated alkyls are selected from the group consisting of —$CF_3$, —$C_4F_9$, —$C_8F_{17}$, —$C_{10}F_{21}$, or mixtures thereof.

In a further embodiment, the present invention relates to a fluorescent, semiconductive polymer represented by formula Ia, Ib, Ic or Id:

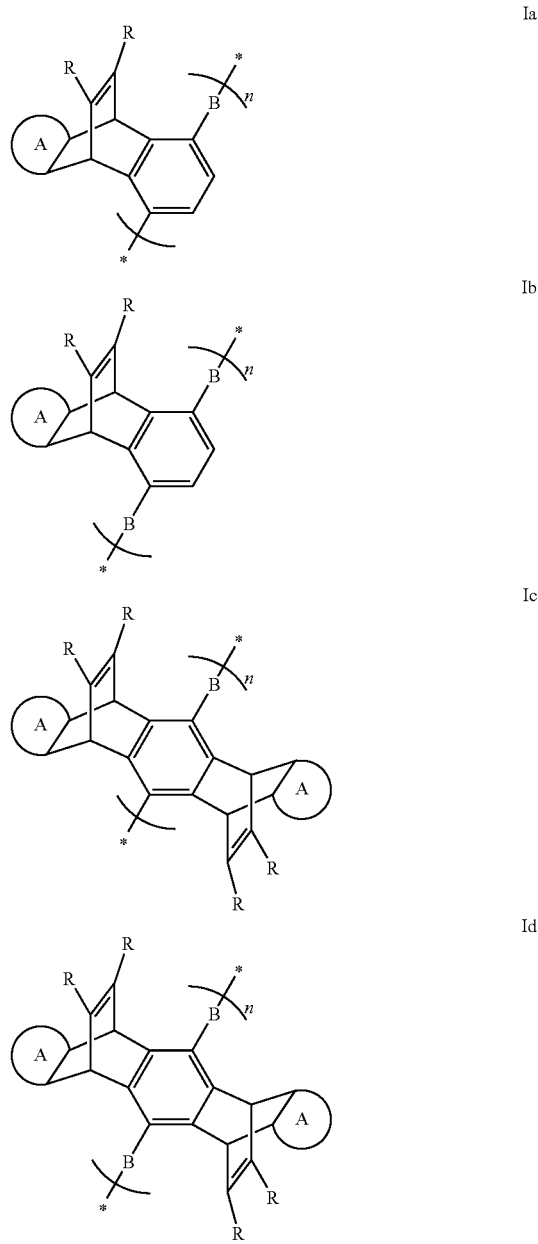

wherein, independently for each occurrence:

R is an electron withdrawing group or the two instances of R taken together form an electron deficient ring;

B is a double bond, triple bond, or aryl; optionally substituted by one or more $R_1$;

$R_1$ is R, H, $C_{1-12}$ alkyl, $C_{2-12}$ alkenyl, $C_{2-12}$ alkynyl, aryl, aralkyl, heteroaryl, or heteroaralkyl;

A is a fused aryl, cycloalkyl, or cycloalkenyl ring;

* depicts an end group for the polymer selected from the group consisting of H, halide, alkyl, alkoxy, and aryl; and n is an integer greater than 1.

In a further embodiment, the present invention relates to a fluorescent, semiconductive polymer of formula Ia-Id and the attendant definitions, wherein R is an ester or a perfluorinated alkyl group.

In a further embodiment, the present invention relates to a fluorescent, semiconductive polymer of formula Ia-Id and the attendant definitions, wherein R is an ester.

In a further embodiment, the present invention relates to a fluorescent, semiconductive polymer of formula Ia-Id and the attendant definitions, wherein R is —$CO_2CH_3$ or —$CO_2C(CH_3)_3$.

In a further embodiment, the present invention relates to a fluorescent, semiconductive polymer of formula Ia-Id and the attendant definitions, wherein R is a perhalogenated alkyl group.

In a further embodiment, the present invention relates to a fluorescent, semiconductive polymer of formula Ia-Id and the attendant definitions, wherein R is a perfluorinated alkyl group.

In a further embodiment, the present invention relates to a fluorescent, semiconductive polymer of formula Ia-Id and the attendant definitions, wherein R is a perfluorinated $C_{1-12}$ alkyl group.

In a further embodiment, the present invention relates to a fluorescent, semiconductive polymer of formula Ia-Id and the attendant definitions, wherein $R_1$ is —$CF_3$, —$C_4F_9$, $C_8F_{17}$, or —$C_{10}F_{21}$.

In a further embodiment, the present invention relates to a fluorescent, semiconductive polymer of formula Ia-Id and the attendant definitions, wherein $R_1$ is —$CF_3$.

In a further embodiment, the present invention relates to a fluorescent, semiconductive polymer of formula Ia-Id and the attendant definitions, wherein $R_1$ is —$C_4F_9$.

In a further embodiment, the present invention relates to a fluorescent, semiconductive polymer of formula Ia-Id and the attendant definitions, wherein $R_1$ is —$C_8F_{17}$.

In a further embodiment, the present invention relates to a fluorescent, semiconductive polymer of formula Ia-Id and the attendant definitions, wherein $R_1$ is —$C_{10}F_{21}$.

In a further embodiment, the present invention relates to a fluorescent, semiconductive polymer of formula Ia-Id and the attendant definitions, wherein at least one set of two R groups taken together form an electron deficient heteroaryl moiety.

In a further embodiment, the present invention relates to a fluorescent, semiconductive polymer of formula Ia-Id and the attendant definitions, wherein $R_1$ is H.

In a further embodiment, the present invention relates to a fluorescent, semiconductive polymer of formula Ia-Id and the attendant definitions, wherein A is a fused benzene ring.

In a further embodiment, the present invention relates to a fluorescent, semiconductive polymer of formula Ia-Id and the attendant definitions, wherein n is greater than about 10, 100, or 1000.

In a further embodiment, the present invention relates to a fluorescent, semiconductive polymer of formula Ia-Id and the attendant definitions, wherein R is —$CO_2Me$, $R_1$ is H, A is a fused benzene ring, and n is greater than about 10, 100, or 1000.

In a further embodiment, the present invention relates to a fluorescent, semiconductive polymer of formula Ia-Id and the attendant definitions, wherein R is —$CF_3$, $R_1$ is H, A is a fused benzene ring, and n is greater than about 10, 100, or 1000.

In a further embodiment, the present invention relates to a fluorescent, semiconductive polymer comprising formula II:

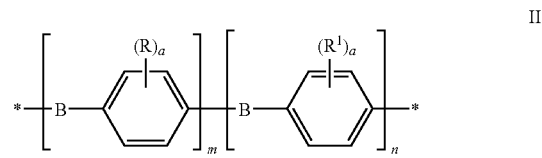

wherein, independently for each occurrence:

B is a double bond, triple bond, or aryl;

R is an electron withdrawing group;

$R^1$ is R, H, $C_{1-6}$ alkyl, $C_{2-8}$ alkenyl, $C_{2-8}$ alkynyl, aryl, aralkyl, heteroaryl, heteroaralkyl, $C_{1-12}$ alkoxy, electron deficient ring, or any two adjacent $R^1$ taken together form a monocyclic, bicyclic, tricyclic, or tetracyclic ring which may be substituted by one or more instance of R;

* depicts an end group for the polymer selected from the group consisting of H, halide, alkyl, alkoxy or aryl;

a is an integer from 1-4 inclusive; and m and n are integers 1 or greater than or equal to 1.

In a further embodiment, the present invention relates to a fluorescent, semiconductive polymer of formula II and the attendant definitions, wherein B is a double bond.

In a further embodiment, the present invention relates to a fluorescent, semiconductive polymer of formula II and the attendant definitions, wherein B is a triple bond.

In a further embodiment, the present invention relates to a fluorescent, semiconductive polymer of formula II and the attendant definitions, wherein B is an aryl.

In a further embodiment, the present invention relates to a fluorescent, semiconductive polymer of formula II and the attendant definitions, wherein R is a perhalogenated alkyl.

In a further embodiment, the present invention relates to a fluorescent, semiconductive polymer of formula II and the attendant definitions, wherein R is a perflourinated alkyl.

In a further embodiment, the present invention relates to a fluorescent, semiconductive polymer of formula II, wherein R is an ester.

In a further embodiment, the present invention relates to a fluorescent, semiconductive polymer of formula II, wherein R is —$CO_2CH_3$ or —$CO_2C(CH_3)_3$.

In a further embodiment, the present invention relates to a fluorescent, semiconductive polymer of formula II and the attendant definitions, wherein R is —$CF_3$, —$C_4F_9$, —$C_8F_{17}$, or —$C_{10}F_{21}$.

In a further embodiment, the present invention relates to a fluorescent, semiconductive polymer of formula II and the attendant definitions, wherein R is —$CF_3$.

In a further embodiment, the present invention relates to a fluorescent, semiconductive polymer of formula II and the attendant definitions, wherein R is —$C_4F_9$.

In a further embodiment, the present invention relates to a fluorescent, semiconductive polymer of formula II and the attendant definitions, wherein R is —$C_8F_{17}$.

In a further embodiment, the present invention relates to a fluorescent, semiconductive polymer of formula II and the attendant definitions, wherein R is —$C_{10}F_{21}$.

In a further embodiment, the present invention relates to a fluorescent, semiconductive polymer of formula II and the attendant definitions, wherein at least one $R^1$ is a perfluorinated $C_{1-12}$ alkyl.

In a further embodiment, the present invention relates to a fluorescent, semiconductive polymer of formula II and the attendant definitions, wherein two $R^1$ are perfluorinated $C_{1-12}$ alkyls.

In a further embodiment, the present invention relates to a fluorescent, semiconductive polymer of formula II and the attendant definitions, wherein at least one $R^1$ is a $C_{1-12}$ alkoxy group.

In a further embodiment, the present invention relates to a fluorescent, semiconductive polymer of formula II and the attendant definitions, wherein two $R^1$ are $C_{1-12}$ alkoxy groups.

In a further embodiment, the present invention relates to a fluorescent, semiconductive polymer of formula II and the attendant definitions, wherein a is 2.

In a further embodiment, the present invention relates to a fluorescent, semiconductive polymer of formula II and the attendant definitions, wherein m and n are greater than about 10, 100, or 1000.

In a further embodiment, the present invention relates to a fluorescent, semiconductive polymer of formula II and the attendant definitions, wherein two sets of adjacent $R^1$ each form a monocyclic ring.

In a further embodiment, the present invention relates to a fluorescent, semiconductive polymer of formula II and the attendant definitions, wherein two sets of adjacent $R^1$ each form a bicyclic ring.

In a further embodiment, the present invention relates to a fluorescent, semiconductive polymer of formula II and the attendant definitions, wherein two sets of adjacent $R^1$ each form a tricyclic ring.

In a further embodiment, the present invention relates to a fluorescent, semiconductive polymer of formula II and the attendant definitions, wherein two sets of adjacent $R^1$ each form a tetracyclic ring.

In a further embodiment, the present invention relates to a fluorescent, semiconductive polymer of formula II and the attendant definitions, wherein two sets of adjacent $R^1$ each form either a monocyclic, bicyclic, tricyclic, or tetracyclic structure wherein at least one structure comprises a heteroaryl ring.

In a further embodiment, the present invention relates to a fluorescent, semiconductive polymer of formula II and the attendant definitions, wherein two sets of $R^1$ are each independently selected from the group consisting of

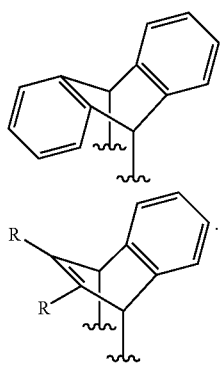

and

In another embodiment, the present invention relates to a method of detecting an analyte, comprising:

a) contacting an analyte with a fluorescent, semiconductive polymer thereby aggregating the fluorescent, semiconductive polymers and thereby optionally forming an emissive exciplex; wherein the maximum emission wavelength of said exciplex is not the same as the maximum emission wavelength of the fluorescent, semiconductive polymer; and b) detecting the partial or complete quenching of the fluorescence of the fluorescent, semiconductive polymer or the emission of the exciplex or both.

In a further embodiment, the present invention relates to the method of detecting an analyte, wherein said analyte is a molecule comprising an electron donating moiety.

In a further embodiment, the present invention relates to the method of detecting an analyte, wherein said contact results in the partial or complete quenching of the fluorescence of the fluorescent, semiconductive polymer.

In a further embodiment, the present invention relates to the method of detecting an analyte, wherein the maximum emission wavelength of the fluorescent, semiconductive polymer and the maximum emission wavelength of the exciplex are separated by at least about 150 nm.

In a further embodiment, the present invention relates to the method of detecting an analyte, wherein the maximum emission wavelength of the fluorescent, semiconductive polymer and the maximum emission wavelength of the exciplex are separated by at least about 200 nm.

In a further embodiment, the present invention relates to the method of detecting an analyte, wherein the maximum emission wavelength of the fluorescent, semiconductive polymer and the maximum emission wavelength of the exciplex are separated by at least about 250 nm.

In a further embodiment, the present invention relates to the method of detecting an analyte, wherein the maximum emission wavelength of the fluorescent, semiconductive polymer and the maximum emission wavelength of the exciplex are separated by at least about 300 nm.

In a further embodiment, the present invention relates to the method of detecting an analyte, the fluorescent, semiconductive polymer having a first emission spectrum and the exciplex having a second emission spectrum, wherein the first emission spectrum and the second emission spectrum overlap by less than about 10%.

In a further embodiment, the present invention relates to the aforementioned method of detecting an analyte, wherein the overlap is less than about 5%.

In a further embodiment, the present invention relates to the method of detecting an analyte, the fluorescent, semiconductive polymer having a first emission lifetime, the exciplex having a second emission lifetime, wherein the first emission lifetime is at least about 100 times greater than the second emission lifetime.

In a further embodiment, the present invention relates to the method of detecting an analyte, wherein the fluorescent, semiconductive polymer has a maximum emission wavelength less than about 700 nanometers.

In a further embodiment, the present invention relates to the method of detecting an analyte, wherein the exciplex has a maximum emission wavelength greater than about 700 nanometers.

In a further embodiment, the present invention relates to the method of detecting an analyte, wherein the analyte is a biological molecule. In a further embodiment, the present invention relates to the method of detecting an analyte, wherein the biological molecule is a protein. In a further embodiment, the present invention relates to the method of detecting an analyte, wherein the biological molecule is a peptide. In a further embodiment, the present invention relates to the method of detecting an analyte, wherein the biological molecule is a mono- or oligonucleotide. In a further embodiment, the present invention relates to the method of detecting an analyte, wherein the biological molecule is an RNA. In a further embodiment, the present invention relates to the method of detecting an analyte, wherein the biological molecule is a DNA. In a further embodiment, the present invention relates to the method of detecting an analyte, wherein the biological molecule is detected when it complexes with another peptide molecule, small molecule, RNA, or DNA.

In another embodiment, the present invention relates to a method of detecting the presence of a molecule comprising an electron donating moiety, comprising:

a) contacting a molecule comprising an electron donating moiety with a fluorescent, semiconductive polymer, thereby quenching partially or completely the fluorescence of the semiconductive polymer and thereby optionally forming an emissive exciplex; wherein the maximum emission wavelength of said exciplex is not the same as the maximum emission wavelength of the polymer; and b) detecting the partial or complete quenching of the fluorescence of the semiconductive polymer or the emission of the exciplex or both.

In a further embodiment, the present invention relates to the method of detecting a molecule comprising an electron donating moiety, wherein the maximum emission wavelength of the fluorescent, semiconductive polymer and the maximum emission wavelength of the exciplex are separated by at least about 150 nm.

In a further embodiment, the present invention relates to the method of detecting a molecule comprising an electron donating moiety, wherein the maximum emission wavelength of the fluorescent, semiconductive polymer and the maximum emission wavelength of the exciplex are separated by at least about 200 nm.

In a further embodiment, the present invention relates to the method of detecting a molecule comprising an electron donating moiety, wherein the maximum emission wavelength of the fluorescent, semiconductive polymer and the maximum emission wavelength of the exciplex are separated by at least about 250 nm.

In a further embodiment, the present invention relates to the method of detecting a molecule comprising an electron donating moiety, wherein the maximum emission wavelength of the fluorescent, semiconductive polymer and the maximum emission wavelength of the exciplex are separated by at least about 300 nm.

In a further embodiment, the present invention relates to the method of detecting a molecule comprising an electron donating moiety, the fluorescent, semiconductive polymer having a first emission spectrum and the exciplex having a second emission spectrum, wherein the first emission spectrum and the second emission spectrum overlap by less than about 10%.

In a further embodiment, the present invention relates to the aforementioned method, wherein the overlap is less than about 5%.

In a further embodiment, the present invention relates to the method of detecting a molecule comprising an electron donating moiety, the fluorescent, semiconductive polymer having a first emission lifetime, the exciplex having a second emission lifetime, wherein the first emission lifetime is at least about 100 times greater than the second emission lifetime.

In a further embodiment, the present invention relates to the method of detecting a molecule comprising an electron donating moiety, wherein the fluorescent, semiconductive polymer has a maximum emission wavelength less than about 700 nanometers.

In a further embodiment, the present invention relates to the method of detecting a molecule comprising an electron donating moiety, wherein the exciplex has a maximum emission wavelength greater than about 700 nanometers.

In a further embodiment, the present invention relates to the method of detecting a molecule comprising an electron donating moiety, wherein the molecule is a biological molecule. In a further embodiment, the biological molecule is a protein. In a further embodiment, the biological molecule is a peptide. In a further embodiment, the biological molecule is a mono- or oligonucleotide. In a further embodiment, the biological molecule is an RNA. In a further embodiment, the biological molecule is a DNA. In a further embodiment, the biological molecule is detected when it complexes with another peptide molecule, small molecule, RNA, or DNA.

In another embodiment, the present invention relates to a light emitting device comprising a fluorescent, semiconductive polymer of the present invention and a source of electrical current comprising electrodes capable of supplying the fluorescent, semiconductive polymer with electrons. In a further embodiment, the fluorescent, semiconductive polymer comprises perfluorinated alkyls and/or perfluorinated aryls, wherein at the interface between the electrodes and fluorescent, semiconductive polymer, metal-carbon bonds are formed. In a further embodiment, the fluorescent, semiconductive polymer comprises perfluorinated alkyls and/or perfluorinated aryls, wherein at the interface between the electrode and the fluorescent, semiconductive polymer, metal-fluoride complexes are formed. In a further embodiment, the fluorescent, semiconductive polymer comprises a nitrogen containing electron deficient heteroaryl, wherein at the interface between the electrode and the fluorescent, semiconductive polymer, metal-nitrogen bonds are formed. In a further embodiment, the fluorescent, semiconductive polymer comprises a nitrogen containing electron deficient heteroaryl and perfluorinated alkyls and/or perfluorinated aryls, wherein at the interface between the electrode and the fluorescent, semiconductive polymer, metal-nitrogen bonds are formed. In a further embodiment, the fluorescent, semiconductive polymer comprises a nitrogen containing electron deficient heteroaryl and perfluorinated alkyls and/or perfluorinated aryls, wherein at the interface between the electrode and the fluorescent, semiconductive polymer, metal-carbon bonds are formed. In a further embodiment, the fluorescent, semiconductive polymer comprises a nitrogen containing electron deficient heteroaryl and perfluorinated alkyls and/or perfluorinated aryls, wherein at the interface between the electrode and the fluorescent, semiconductive polymer, metal-fluoride complexes are formed.

In another embodiment, the present invention relates to a sensor comprising a fluorescent, semiconductive polymer of the present invention and a detector capable of detecting a decrease in fluorescence and increase in fluorescence or both. In a further embodiment, the sensor is a biosensor.

In another embodiment, the present invention relates to a photovoltaic device comprising the fluorescent, semiconductive polymer of the present invention and a source of electrical current comprising an electrode, wherein the photovoltaic cell is capable of displaying a current or voltage in response to the presence of photons that can be absorbed by the polymer. In a further embodiment, the fluorescent, semiconductive polymer comprises perfluorinated alkyls and/or perfluorinated aryls, wherein at the interface between the electrode and the fluorescent, semiconductive polymer, metal-carbon bonds are formed. In a further embodiment, the fluorescent, semiconductive polymer comprises perfluorinated alkyls and/or perfluorinated aryls, wherein at the interface between the electrode and the fluorescent, semiconductive polymer, metal-fluoride complexes are formed. In a further embodiment, the fluorescent, semiconductive polymer comprises a nitrogen containing electron deficient heteroaryl, wherein at the interface between the electrode and the fluorescent, semiconductive polymer, metal-nitrogen bonds are formed. In a further embodiment, the fluorescent, semiconductive polymer comprises a nitrogen containing electron deficient heteroaryl and perfluorinated alkyls and/or perfluorinated aryls, wherein at the interface between the electrode and the fluorescent, semiconductive polymer, metal-nitrogen bonds are formed. In a further embodiment, the fluorescent, semiconductive polymer comprises a nitrogen containing electron deficient heteroaryl and perfluorinated alkyls and/or perfluorinated aryls, wherein at the interface between the electrode and the fluorescent, semiconductive polymer, metal-carbon bonds are formed. In a further embodiment, the fluorescent, semiconductive polymer comprises a nitrogen containing electron deficient heteroaryl and perfluorinated alkyls and/or perfluorinated aryls, wherein at the interface between the electrode and the fluorescent, semiconductive polymer, metal-fluoride complexes are formed.

DETAILED DESCRIPTION OF THE INVENTION

Definitions

Figure 1:
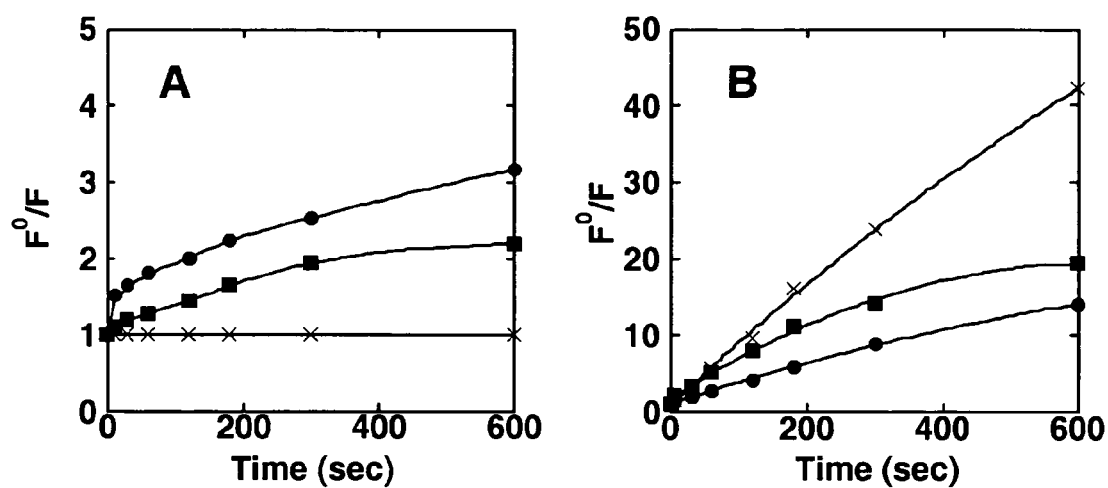
FIG. 1 depicts Stern-Volmer plots of polymers 4a (■), 4b (●) and 4d (X) in spin-cast films with DMT (A) and DNT (B) vapor.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59 (McGraw Hill Book Company: New York, 1977). The Hammett constant values are generally negative for electron donating groups (σ(P)=−0.66 for $NH_2$) and positive for electron withdrawing groups (σ(P)=0.78 for a nitro group), σ(P) indicating para substitution. Exemplary electron-withdrawing groups include halogenated alkyl groups such as trifluoromethyl, acyl, formyl, sulfonyl, sulfonium, sulfate, nitrile, halide, any electron deficient ring as compared to benzene (e.g. a benzene ring with an electron withdrawing group attached to the ring or a nitrogen containing aromatic ring), esters, and the like.

The term "polymer" is art-recognized and refers to large molecules formed by the union of simple molecules known as monomers. For example polyethylene is a polymer resulting from the polymerization of ethylene.

The term "fluorescence" is art-recognized and refers to the emission of electromagnetic radiation caused by an electronic transition from an excited electronic state of a given spin to a lower energy electronic state of the same spin state, i.e., singlet to singlet. Whereas, phosphorescence is due to an electronic transition from an excited state of a given spin to a lower energy state of a different spin.

The term "sensor" is art-recognized and refers to any device that senses either the absolute value or a change in a physical or chemical quantity, such as temperature, pressure, flow rate, or pH, or the intensity of light, sound, or radio waves, or presence of a small molecule, or presence of a biological molecule, or a change in the property of a bound molecule, and converts that change into a useful input signal for an information gathering system. For example, the fluorescent, semiconductive polymers of the present invention may be used as a sensor because they sense the presence of different chemical entities by displaying a change in energy flow and emitted light as a useful input signal.

The term "voltaic cell" is art-recognized and refers to a cell comprising two dissimilar or similar electrodes in contact with one or more substances that can be acted upon chemically or photochemically to produce a change in the volatage and current flowing between the two electrodes.

The term "OLED" is art-recognized and stands for "organic light emitting device."

The term "PLED" is art-recognized and stands for "polymer light emitting device."

The term "photobleaching" is art-recognized and refers to upon exposure to light, the decrease in absorbance intensity and/or, in the case of fluorescent materials, a decrease in emission intensity.

As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

Various aspects of the present invention include conjugated polymers that may be fluorescent. Polymers are generally extended molecular structures comprising backbones which optionally contain pendant side groups. As used herein, "backbone" is given its ordinary meaning as used in the art, e.g., a linear chain of atoms within the polymer molecule by which other chains may be regarded as being pendant. Typically, but not always, the backbone is the longest chain of atoms within the polymer.

A conjugated polymer is a polymer in which at least a portion of the polymer is conjugated, i.e. the polymer has at least one conjugated portion. "Conjugated," as used herein, refers to an interconnected chain of at least three atoms, each atom participating in delocalized pi-bonding. Electron density or electronic charge can be conducted along the conjugated portion of the polymer. Each p-orbital participating in conjugation may have sufficient overlap with adjacent conjugated p-orbitals. In one embodiment, the conjugated portion is at least about 3 nm in length. In another embodiment, the entire backbone may be conjugated. An example of a conjugated polymer is a polyacetylene chain. Other non-limiting examples include polyethylenes, poly(ethylene terephthalate)s, polyarylenes such as polyphenylenes, polythiophenes, polypyrroles, poly(arylene vinylene)s such as poly(phenylene vinylene)s, poly(arylene ethynylene)s such as poly(phenylene ethynylene)s, ladder polymers, etc., where "aryl" generally refers to an aromatic moiety, i.e., a moiety having at least one ring in which some electrons are delocalized in the ring. For instance, the aromatic moiety may include a benzene moiety, a naphthalenyl moiety, an anthracenyl moiety, a pyridinyl moiety, a furanyl moiety, etc. As used herein, a "ladder polymer" is a polymer having a backbone that cannot be severed without breaking at least two bonds. Co-polymers of these and/or other polymers are also polymers that can be used in the invention, for example, block, alternating, or random co-polymers, etc.

The conjugated polymer may have, in some cases, a chromophore that can absorb or emit electromagnetic radiation, for example, in the ultraviolet and/or visible range. For example, the chromophore may absorb energy, allowing the chromophore to achieve an excited state. The chromophore may also emit energy (e.g., as radiation) to achieve a lower energy state, and/or transmit energy through at least a portion of the conjugated polymer. Those of ordinary skill in the art will be able to identify the presence of a chromophore within a polymer. For instance, in one embodiment, the chromophore is a conjugated group. In another embodiment, the emitted radiation is created through luminescence, in which "luminescence" is defined as including ultraviolet and/or visible radiation. Specific types of luminescence include "fluorescence" and "phosphorescence." A chromophore able to fluoresce is also referred to herein as a "fluorophore." In some cases, the chromophore may have a maximum emission wavelength (i.e., the wavelength at the maximum intensity of the emission spectrum) greater than about 500 nm, greater than about 600 nm, greater than about 700 nm, or greater than about 800 nm. In some embodiments, the maximum emission wavelength may be between about 400 nm and about 700 nm, between about 300 micrometers and 700 nm, between about 400 nm and about 10 nm, etc. In some cases, the maximum emission wavelength may be between about 350 nm and about 1000 nm, between about 300 micrometers and about 500 nm, between about 500 nm and about 1 nm, between about 400 nm and about 700 nm, between about 600 nm and about 1000 nm, between about 500 nm and about 50 nm, etc. Those of ordinary skill in the art will be able to determine the emission (e.g., fluorescence, phosphorescence, etc.) of a polymer, for example, using known spectrofluorimetric techniques such as fluorometers, plate readers, fluorescence scanners, flow cytometers, fluorescence microscopes, etc.

A conjugated polymer may also allow energy transfer to occur along an "energy migration pathway" of the polymer, for example, a conjugated portion of the polymer. An energy migration pathway is a pathway which allows for the conduction of energy (i.e., without emission) away from a chromophore which has absorbed energy. The energy may be transferred, e.g., to another chromophore (e.g., a fluorophore) within the same polymer, and/or a chromophore of a different polymer located proximate the chromophore and/or the polymer comprising the chromophore. In some cases, an energy exchange mechanism, such as a Dexter energy transfer mechanism or the strong coupling effect, may facilitate energy transfer between a first chromophore on a first polymer and a second chromophore. The second chromophore may be, for example, present on the first polymer or present on a second polymer (which may be the same as or different than the first polymer), as further described below.

When a polymer includes conjugated portions, the polymer can, in some cases, undergo a phenomena known as "pi-stacking," which involves electron interactions between pi-orbitals of the conjugated portions of the same and/or different polymer molecules. If the polymer also includes a chromophore, a pi-stacking arrangement may also facilitate energy transfer between chromophores species.

The term "exciplex" is art-recognized and refers to an electronically excited complex of definite stoichiometry, 'non-bonding' in the ground state. For example, a complex formed by the interaction of an excited molecular entity with a ground state counterpart of a different structure.

As used herein, "binding" can involve any hydrophobic, non-specific, or specific interaction, and the term "biological binding" refers to the interaction between a corresponding pair of molecules that exhibit mutual affinity or binding capacity, typically specific or non-specific binding or interaction. Biological binding defines a type of interaction that occurs between pairs of molecules including proteins, nucleic acids, glycoproteins, carbohydrates, hormones, and the like.

Specific examples include protein/carbohydrate, antibody/antigen, antibody/hapten, biotin/streptavidin, biotin/avidin, enzyme/substrate, enzyme/inhibitor, enzyme/cofactor, protein/substrate, lectin/carbohydrate, receptor/hormone, receptor/effector, complementary strands of nucleic acid (e.g., DNA and/or RNA), protein/nucleic acid, repressor/inducer, ligand/receptor, virus/ligand, etc. Further, the term "binding partner" refers to a molecule that can undergo binding with a particular molecule. "Specific interaction" is given its ordinary meaning as used in the art, i.e., an interaction between pairs of molecules where the molecules have a higher recognition or affinity for each other than for other, dissimilar molecules. Biotin/avidin and biotin/streptavidin are examples of specific interactions. In some cases, the specific interaction involves uncharged molecules or neutral ligands.

As used herein, a "biological entity," is an entity deriving at least partially from a biological source. Non-limiting examples of biological entities include proteins, peptides, nucleic acids (e.g., oligonucleotides, which may include DNA and/or RNA), fatty acids, carbohydrates, sugars, hormones, enzymes, receptors, lipids, viruses, bacteria, cells, and the like. In some cases, the biological entity has the capability for reproduction, which can be self-reproduction, i.e., a biological entity is a cell (e.g., a bacterium) or a virus. In certain cases, the biological entity is a "pathogen," i.e., an entity capable of causing a disease when introduced into a subject, for example, a human, a dog, a cat, a horse, a cow, a pig, a sheep, a goat, a chicken, a primate, a rat, a mouse, etc.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term alkyl also includes perhalogenated alkyls.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryls." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art recognized and includes an aromatic or non-aromatic ring in which each atom of the ring is carbon. The flowing art-recognized terms have the following meanings: "nitro" means —$NO_2$; the term "halogen" designates —F, —Cl, —Br or —I; the term "sulfhydryl" means —SH; the term "hydroxyl" means —OH; and the term "sulfonyl" means —$SO_2^-$.

The terms "amine" and "amino" are art-recognized and include both unsubstituted and substituted amines, e.g., a moiety that may be represented by the general formulas:

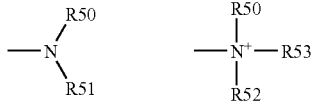

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

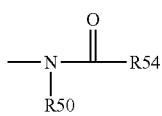

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

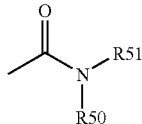

wherein R50 and R51 are as defined above. Certain embodiments of the amide in the present invention will not include imides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

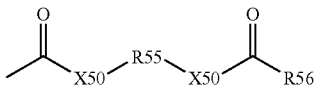

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and includes a moiety that may be represented by the general formula:

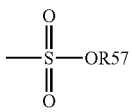

in which R57 is an electron pair, hydrogen, alkyl, cycloalkyl, or aryl.

The term "sulfate" is art recognized and includes a moiety that may be represented by the general formula:

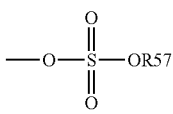

in which R57 is as defined above.

The term "sulfonamido" is art recognized and includes a moiety that may be represented by the general formula:

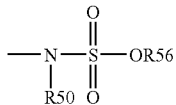

in which R50 and R56 are as defined above.

The term "sulfamoyl" is art-recognized and includes a moiety that may be represented by the general formula:

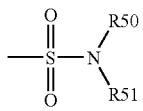

in which R50 and R51 are as defined above.

The term "sulfonyl" is art recognized and includes a moiety that may be represented by the general formula:

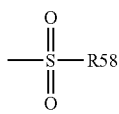

in which R58 is one of the following: hydrogen, alky, alkenyl, alkynyl, cycloalkyl, heterocyclyl, aryl or heteroaryl.

The term "sulfoxido" is art recognized and includes a moiety that may be represented by the general formula:

in which R58 is defined above.

The term "phosphoramidite" is art recognized and includes moieties represented by the general formulas:

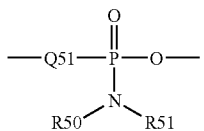 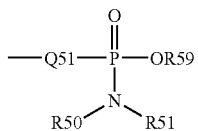

wherein Q51, R50, R51 and R59 are as defined above.

The term "phosphonamidite" is art recognized and includes moieties represented by the general formulas:

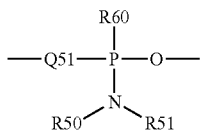 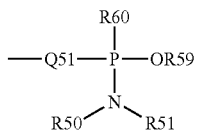

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

For purposes of this invention, the chemical elements are identified in accordance with the Periodic Table of the Elements, CAS version, Handbook of Chemistry and Physics, 67th Ed., 1986-87, inside cover.

Overview

In part, the present invention discloses CP designs that produce high fluorescence quantum yields and also tune electron affinity. Simultaneously, architectures are presented for the covalent attachment of the CPs to peptides, nucleic acids or antibodies for biosensor applications that avoid deleterious reductions in their electronic delocalization. Herein, CPs having three-dimensional structures that display highly efficient solid-state fluorescence and demonstrate how hyperconjugation can be used to tune their electron affinity are disclosed, as well as CPs having dramatically different electronic properties due to strongly electron withdrawing groups directly attached to their conjugated backbone.

The direct attachment of electron withdrawing substituents to the conjugated portion of semiconductive polymers results in a number of important technological consequences. Semiconductive polymers containing perfluorinated alkyl groups as the electron withdrawing group have a very high electron affinity that prevents oxidative degradation (photobleaching). Photobleaching studies reveal that the perfluoro-alkyl materials have vastly superior stability when compared to other semiconductive organic polymers. The perfluorinated alkyl polymers are completely stable with their fluorescence intensity undiminished after hours of irradiation with UV light (e.g. a 450 W, short-arc, Xe lamp) in a solid state under ambient atmosphere. This extraordinary durability is unprecedented for semiconductive organic polymers and endows the materials with the critical stability needed for many sensor, photovoltaic, display, and electronic technologies.

Additionally, the perfluoro-alkyls in some cases provide solubility that the analogous polymers of equal chain length hydrocarbon substituents do not possess. The greater size of the perfluoro-alkyl also appears to prevent strong interpolymer interactions; and as a consequence, thin films of these materials maintain a brilliant solid-state fluorescence. The high electron affinity of these perfluoro-alkyl substituted polymers also complements other sensor materials in that they respond to a different classes of materials. For example, although high electron withdrawing compounds, such as nitro aromatics, strongly quench other polymers, the perfluoro-alkyl semiconducting polymers described herein are quenched only modestly, if at all, by nitro aromatics. In contrast, the perfluoro-alkyl semiconducting polymers are strongly quenched by highly electron donating molecules. Typical semiconductive organic sensory polymers do not respond to electron donating materials; hence, these materials have a unique sensory function. In particular, it has been demonstrated that these materials are highly quenched by indole, which is an electron rich aromatic moiety found in many peptides. It is anticipated that the perfluoronated alkyl semiconductive polymers will have general utility for the transduction of peptides, RNA, and DNA.

In addition to their sensory function, these materials have many applications for light emitting devices, including organic light emitted devices (OLEDs). There is a general need for materials which are n-type conductors for these technologies. Additionally, the high electron affinity of these materials, and the presence of perfluoro alkyls, can give rise to unique interactions at metal polymer interfaces. In particular, the perfluoro alkyls provide a thermodynamically favorable and unique type of activity with reactive metal interfaces. It is anticipated that by evaporating metal onto these materials will generate highly stable metal fluorides and new perfluorinated alkyl groups bound to the metal ions. Metals bound to perfluorinated alkyl groups are known to be more stable than their hydrocarbon analogs; hence, these structures can give rise to very stable interfaces between the metals and polymers. This is important because many OLED technologies suffer from degradation of the cathode interface, and these materials may offer a general solution for stabilizing such interfaces. For photovoltaic applications, the high durability of these perfluoro alkyl group materials is also useful. For long-term use in exterior applications, stability to UV light is a necessity. Indeed, the extraordinary stability of these materials makes them unique among present day organic polymers and viable for these demanding applications. The fact that the polymers are processable with minimal amounts of insulating (electronically inactive) substituents makes them attractive for electrical conduction. This is important for the design of superior photovoltaic materials, and also lends itself to the use of these materials in different types of electronic functions, such as organic transistors, which may be photo activated in sensory devices.

Semiconducting Polymers Having Electron Withdrawing Groups Bonded to a Non-Conjugated Portion.

To perturb the electronic structure of CPs without interrupting conjugation by adding steric bulk in the plane of polymer backbone, a [2.2.2] bicyclic ring system that contains an electron deficient double bond that can interact with the polymer backbone in a hyperconjugative fashion was designed (Scheme 1).

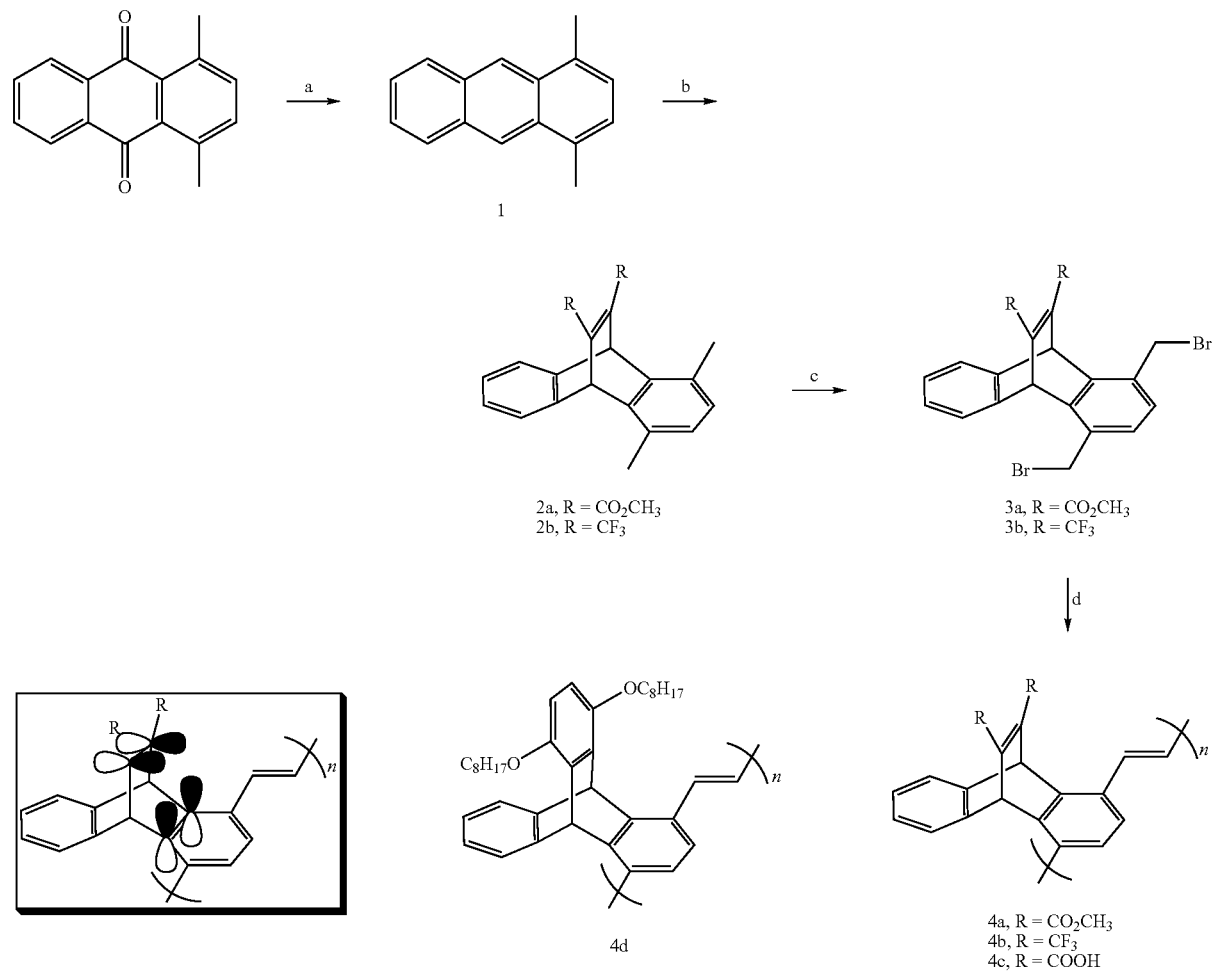

Scheme 1. Synthesis of [2.2.2] bicylic ring PPV. NaBH₄, 2-propanol, reflux.

2a, R = CO₂CH₃
2b, R = CF₃

3a, R = CO₂CH₃
3b, R = CF₃

4a, R = CO₂CH₃
4b, R = CF₃
4c, R = COOH (b) dimethylacetylenedicaboxylate or hexafluoroacetylene, xylene, 140° C.
(c) NBS, AIBN, CCl₄, reflux.
(d) KO^tBu, THF, r.t.

Compounds 3a and 3b, which have at least one electron withdrawing group appended to the alkene of the bicyclic ring system, were synthesized and then polymerized by reaction with excess KO$^t$Bu to give polymers 4a and 4b (Scheme 1). (a) Huang, N. Z.; Jia, J. H.; Wang, L. L. *Tetrahedron Letters*, 1982, 23, 4797-4800. (b) Chan, T-L.; Mak, T. C. W.; Poon, C.-D.; Wong, H. N. C.; Jia, J. H.; Wang, L. L. *Tetrahedron*, 1986, 42, 655-661. Ester groups in polymer 4a included both methyl and (30%) tert-butyl groups, with the latter being produced by transesterification under the polymerization conditions. The triptycene polymer 4d (Scheme 2) represents an electron-rich model polymer for the comparison with relative electron-poor polymers 4a and 4b. The absorption and emission maxima of polymers 4a and 4b are extremely similar (Table 1). High fluorescence quantum yields were observed for all of the polymers in THF solution and in thin films. The latter feature is attributed to the greatly reduced interchain interactions enforced by the three-dimensional frameworks. Yang, Y. S., Swager, T. M. *J. Am. Chem. Soc.*, 1998, 120, 11864.

Scheme 2. Preparation of polymer 4d with electron donating groups.

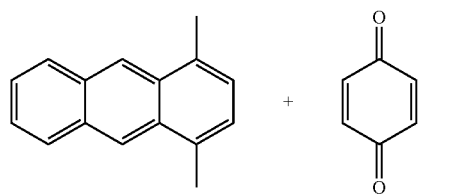

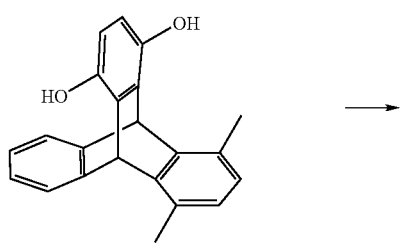

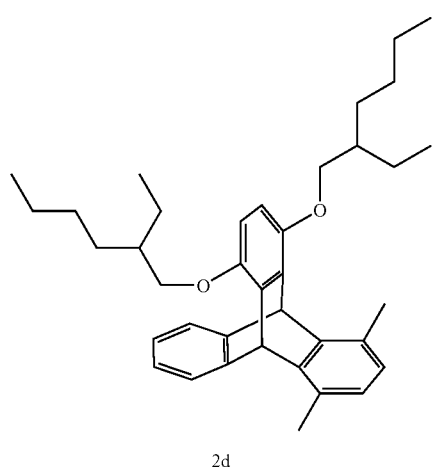

2d

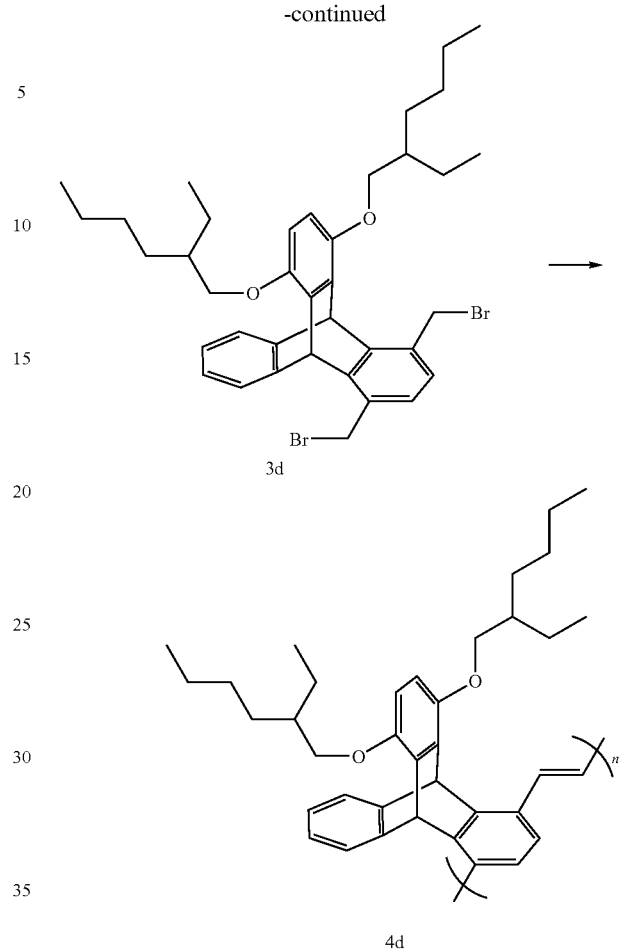

TABLE 1

Summary of Molecular Weight and Photophysical Data

| Polymer | GPC (Mn) | PDI | Abs $\lambda_{max}$ (nm) (log ε) | em $\lambda_{max}$ (nm) | Φ | τ (ns) |
|---|---|---|---|---|---|---|
| 4a (THF) | $1.2 \times 10^5$ | 2.5 | 401 (3.83) | 473, 498 | 0.58 | 1.16 |
| 4a (Film) | | | 401 | 507 | 0.42 | |
| 4b (THF) | $6.8 \times 10^4$ | 2.6 | 403 (3.48) | 471, 497 | 0.86 | 0.75 |
| 4b (Film) | | | 405 | 506 | 0.43 | |
| 4d (THF) | $7.9 \times 10^5$ | 2.1 | 413 (4.32) | 469, 499 | 0.76 | 0.62 |
| 4d (Film) | | | 414 | 477, 511 | 0.61 | |

Fluorescence Quenching Studies

The effect of hyperconjugative perturbations on the sensory properties was determined by investigating fluorescence quenching responses of thin films with exposure to vapors of electron-rich (N,N-dimethyl p-toluidine (DMT)) and electron-deficient (2,4-dinitrotoluene (DNT)) aromatic compounds. All of thin films displayed the largest quenching response (FIG. 1) to DNT despite the fact that it has lower vapor pressure ($1.47\times10^{-4}$ mm Hg) than DMT ($1.78\times10^{-1}$ mm Hg). This result is likely due to the formers' strong π-acid character that favors association with electron-donating π-electron systems. Yang, Y-S.; Swager, T. M. *J. Am. Chem.*

Soc. 1998, 120, 11864-11873. As shown in FIG. 1 the relative quenching response of 4a, 4b and 4d reflects the expected hyperconjugative effects with 4b being the most oxidizing and 4d being the most reducing. Hence, 4b gives the strongest relative response to DMT and the weakest relative response to DNT. Correspondingly 4d displays the opposite behavior having a larger response relative to the other polymers to DNT and a weaker relative response to DMT. Polymer 4a exhibits responses intermediate to those of 4b and 4d.

Figure 2:
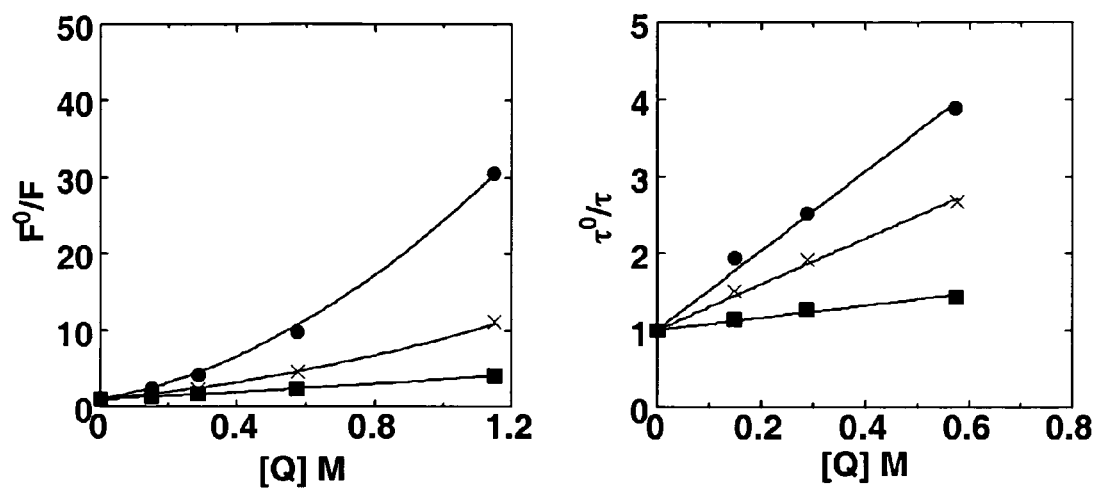
FIG. 2 depicts Stern-Volmer plots of polymers 4a (■), 4b (●) and 4d (X) with N,N-dimethyl p-toluidine (DMT) in THF.

To further investigate the quenching behavior, solution Stem-Volmer quenching studies were conducted to determine the rates of static and dynamic quenching by performing steady state and time-resolved experiments (FIG. 2). Lakowicz, J. R. Principles of Fluorescence Spectroscopy; Plenum Press: New York, 1986. Static quenching, involving a preformed complex, does not reduce the excited state lifetime whereas dynamic quenching, resulting from diffusion, lowers the lifetime.

The trends in the solution Stern-Volmer rate constants, summarized in Table 2, contrast markedly to those from the thin film studies. As expected the electron-poor polymer 4b exhibits the largest quenching (both static and dynamic) with DMT (FIG. 2). However, polymer 4d, the most electron-rich polymer, has a much higher diffusive quenching rate than diester containing 4a. The deviations from thin film behaviors are even more pronounced with DNT quenching. In this case 4d exhibits the lowest static quenching ($K_{sv}$) even though it has the best sensitivity in thin films. These results underscore the fact that the sensory behaviors of conjugated polymers in solution can be very different than their responses in devices that often employ thin films. There are multiple origins for these differences including different hydrodynamic volumes for each polymer that can be influenced by the analyte, steric effects that restrict the close approach of quenchers, and the degree of amplification by energy migration. For 4d its lower than expected solution sensitivity to DNT is likely due to the steric bulk of its alkyl sidechains and as a result it exhibits smaller static quenching than 4a and 4b even though it should be a better π-base.

TABLE 2

The Quenching Constants of Polymers 4a, 4b and 4d.[a]

| Polymer | Quencher | $K_D$ (M$^{-1}$) | $K_S$ (M$^{-1}$) | $k_q$ (M$^{-1}$s$^{-1}$) |
|---|---|---|---|---|
| 4a | DMT | 0.80 | 0.92 ± 0.58 | 6.9 × 10$^8$ |
| 4b | DMT | 5.19 | 2.49 ± 0.60 | 7.0 × 10$^9$ |
| 4d | DMT | 2.99 | 0.94 ± 0.67 | 4.8 × 10$^9$ |
| 4a | DNT | 11.00 | 86 ± 65 | 9.4 × 10$^9$ |
| 4b | DNT | 7.60 | 108 ± 93 | 1.0 × 10$^{10}$ |
|    | DNT | 8.00 | 25 ± 15 | 1.3 × 10$^{10}$ |

[a]See supporting information for details of experimental conditions. ($K_D$, $K_S$, and $k_q$: Stern-Volmer quenching constant for dynamic, static quenching and bimolecular quenching constant, respectively).

Acid-Base Response of PPV Polymers

Figure 3:
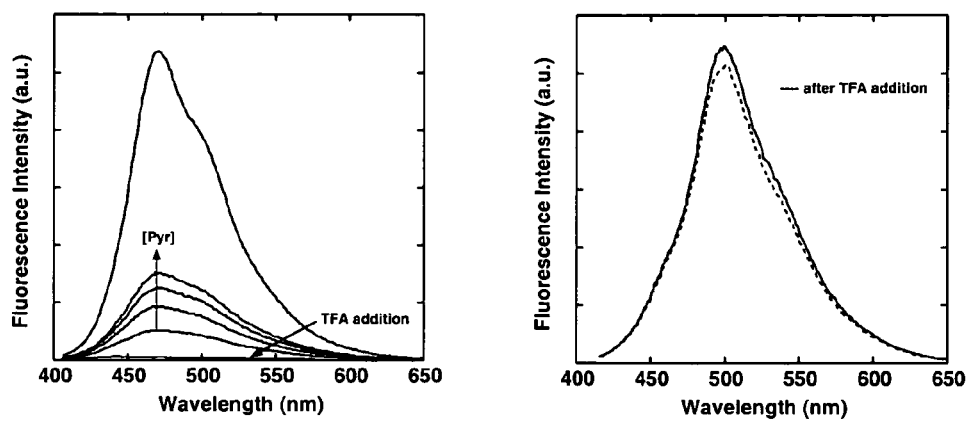
FIG. 3 depicts emission spectra of polymer 4a (left) and 4b (right) when treated with TFA and then pyridine.
Figure 4:
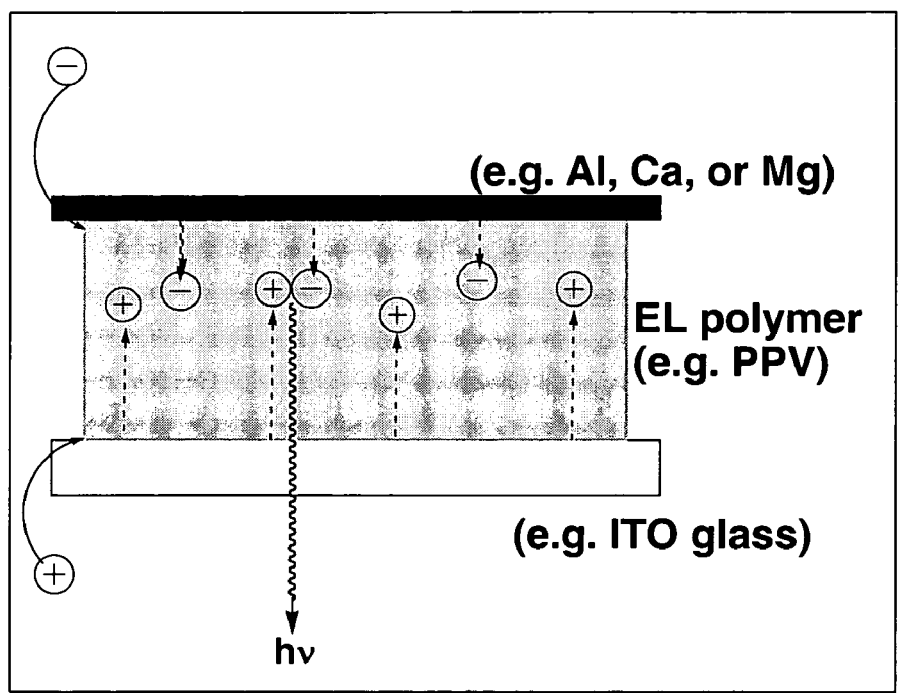
FIG. 4 depicts the charge transfer process across the interface between a metal electrode and a semiconductive polymer.
Figure 5:
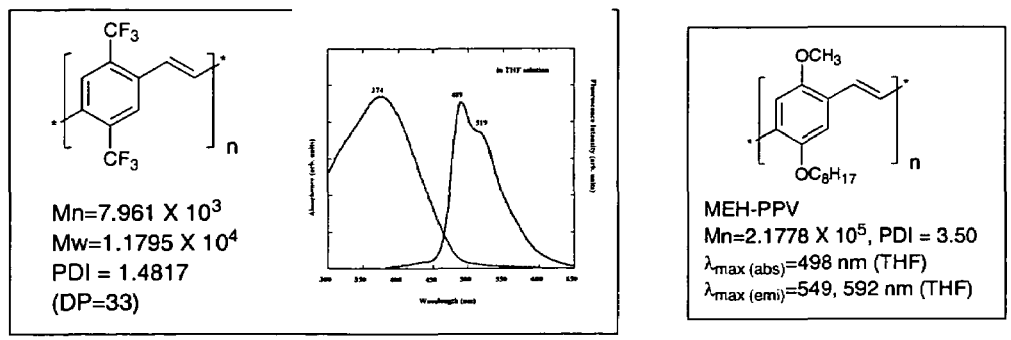
FIG. 5 depicts various perfluorinated alkyl PPVs and corresponding physical data.
Figure 5:
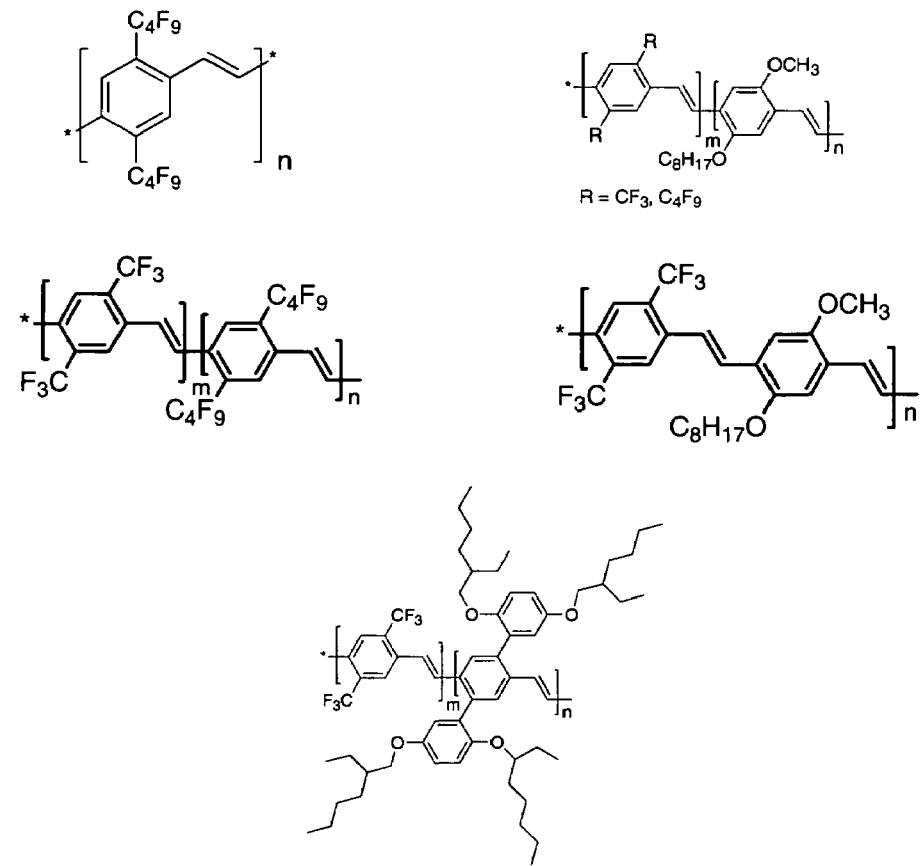

Emerging sensor applications of CPs require conjugation to biorecognition elements and to this end we have tested the stability of 4a and 4b to conditions associated with solid phase peptide synthesis. (a) McQuade, D. T.; Pullen, A. E.; Swager, T. M. Chem. Rev. 2000; 100, 2537-2574. (b) Swager, T. M. Acc. Chem. Res. 1998, 31, 201-207. Conjugated polymers often exhibit reactivity with strong electrophiles such as trifluoroacetic acid (TFA), however exposure of 4b in $CH_2Cl_2$ solutions of TFA or immersion of solids in neat TFA results in no apparent reduction/modification of its emission. Three drops of trifluoroacetic acid (TFA) was added to 1 cm quartz cuvette containing polymer 4a and 4b dissolved in $CH_2Cl_2$ at room temperature, respectively and then their emission spectra were observed. In the case of polymer 4a, the fluorescence spectra were recorded with the increase of concentration of pyridine added to the $CH_2Cl_2$-TFA suspension of polymer 4a (FIG. 3). Methylene chloride solutions 4a are quenched with the addition of TFA, however its fluorescence was immediately and completely recovered without any spectral shift after neutralization with pyridine. Aqueous acid treatment of the polymer 4a leads to the hydrolysis of both ester groups to give 4c. Polymer 4a is also readily modified with amide or glycol moieties, which are of interest from the standpoint of biocompatibility. (a) Kuroda, K.; Swager, T. M. Chem. Commun. 2003, 26-27. (b) Newkome, G. R.; Behera, R. K.; Moorefield, C. N.; Baker, G. R. J. Org. Chem. 1991, 7162-7167.

Semiconducting Polymers Having Electron Withdrawing Groups Bonded Directly to the Conjugated Backbone Synthesis of PPV Polymers with Electron Withdrawing Groups Bonded to the Conjugated Backbone.

The polymers may be prepared by any conventional method useful for the preparation of analogous polymers and as described in the examples below. Starting materials for the processes described in the present patent application are known or can be prepared by known processes from commercially available materials. A polymer of the present invention can be converted to another polymer of the present invention using conventional methods. The products of the reactions described herein are isolated by conventional means such as extraction, crystallization, distillation, chromatography, and the like. The general synthetic procedure is disclosed in Schemes 3-15 wherein the electron withdrawing group is a perfluorinated alkyl.

Scheme 3. Preparation of monomers 4 and 5 with trifluoromethyl groups.

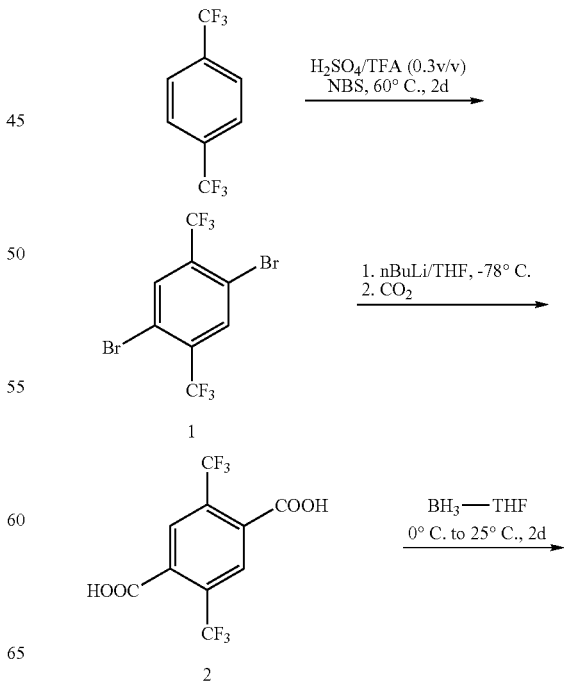

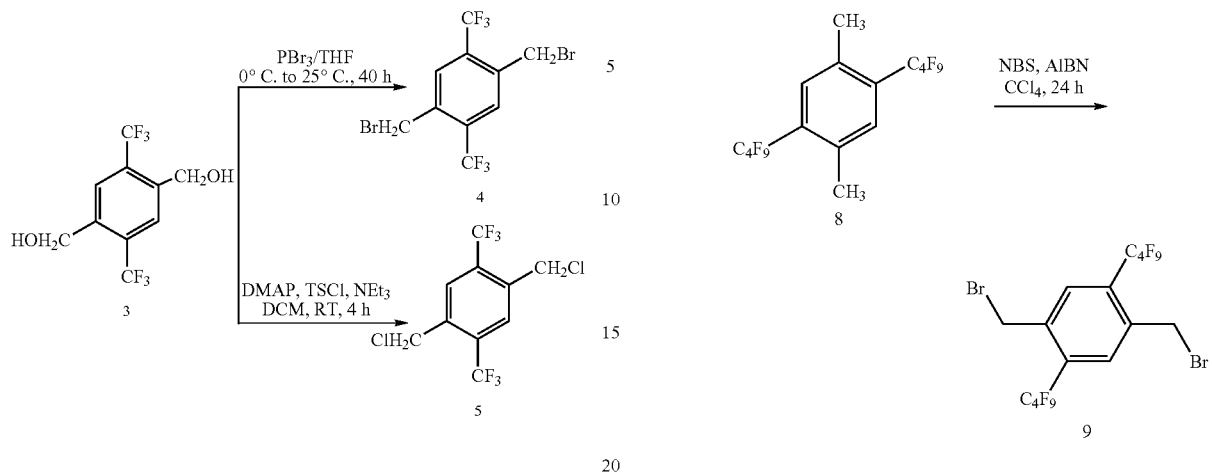
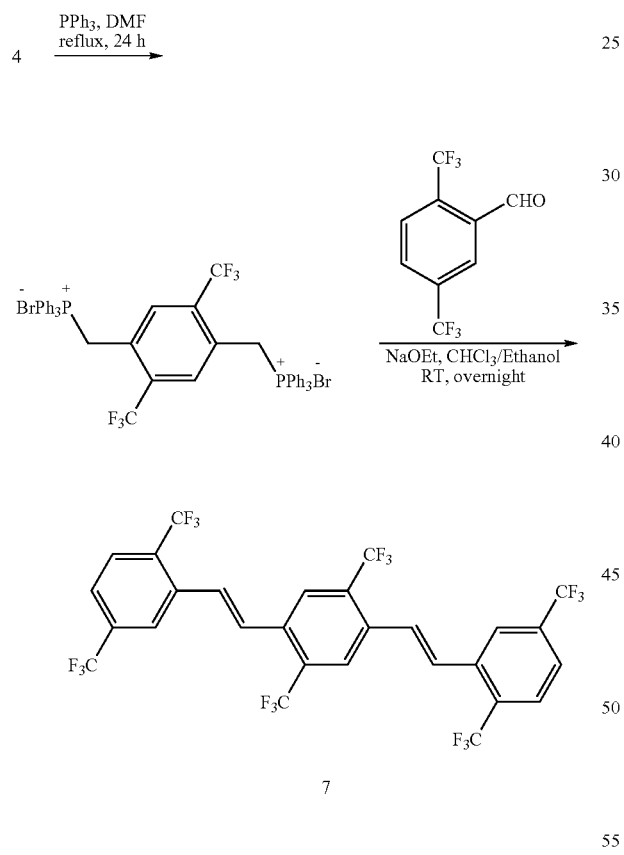
Scheme 4. Preparation of oligomer 7.
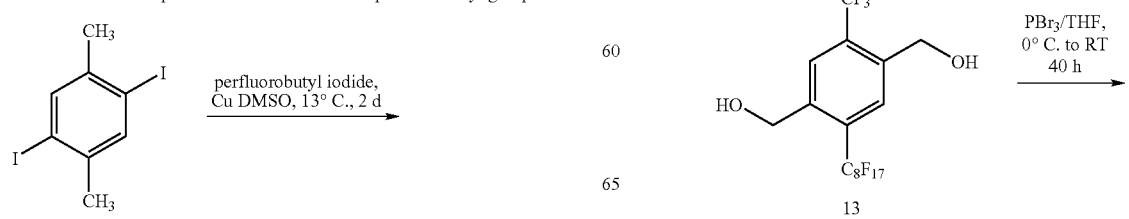
Scheme 6. Preparation of monomer 14 with perfluorooctyl groups.
Scheme 5. Preparation of monomer 9 with perfluorobutyl groups.

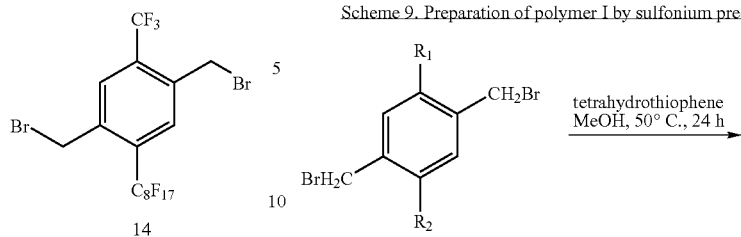
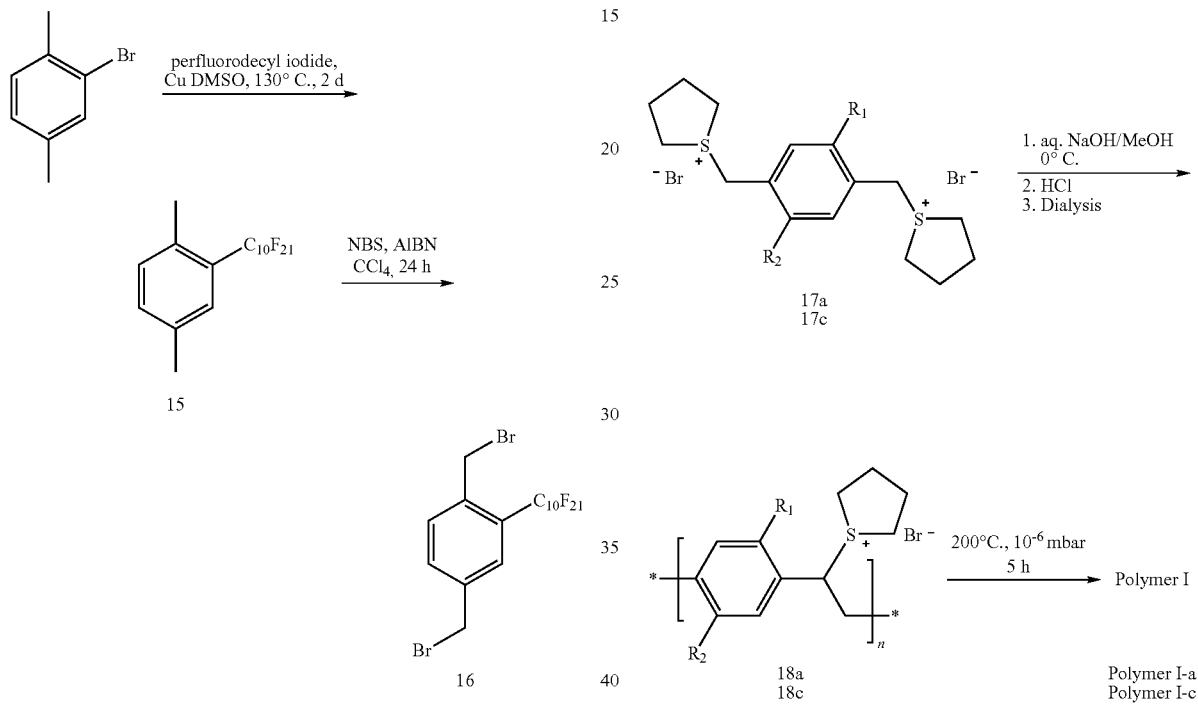
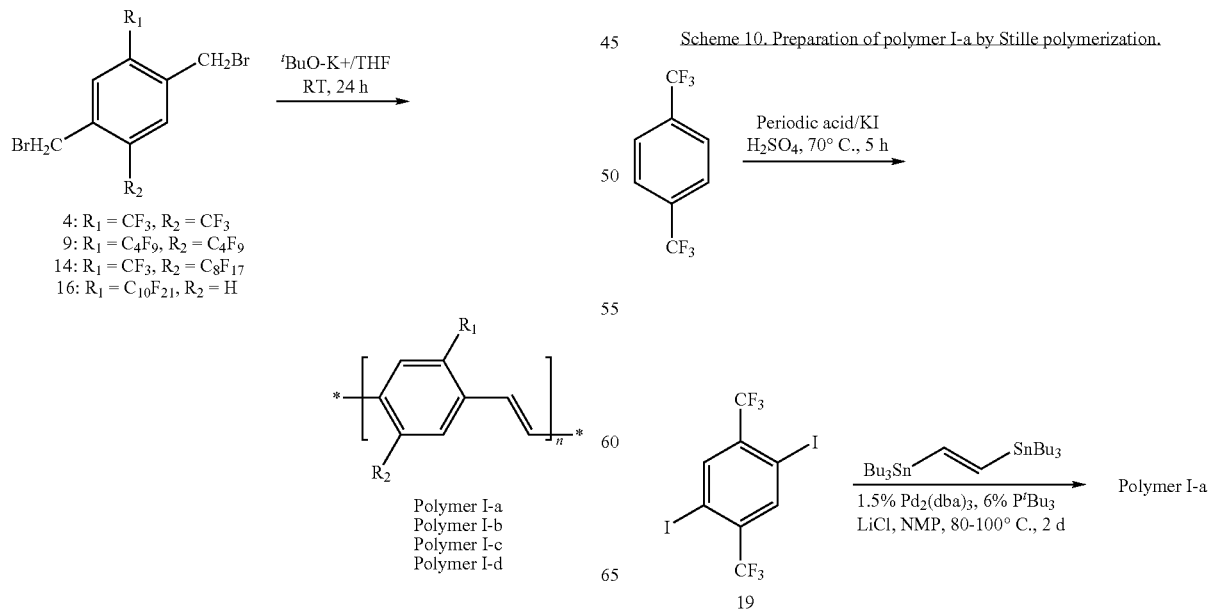

Scheme 11. Preparation of alternating copolymers II-a.
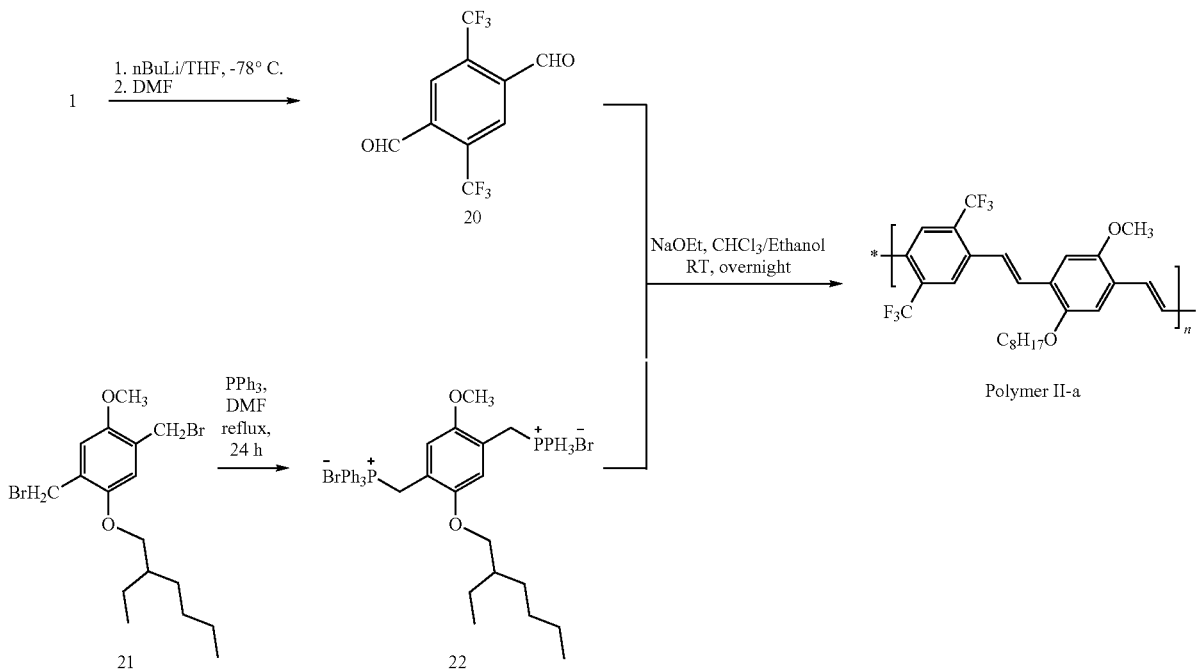
Scheme 12. Preparation of alternating copolymers II-b and II-c.
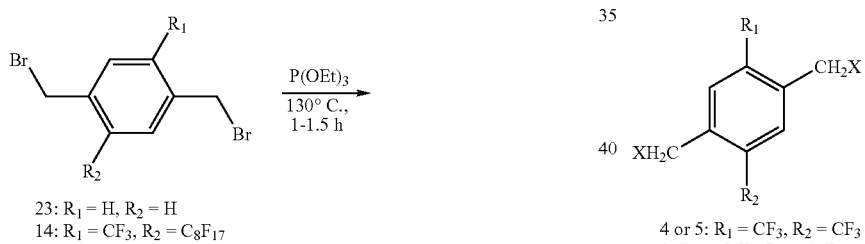
Scheme 13. Preparation of random copolymers III.
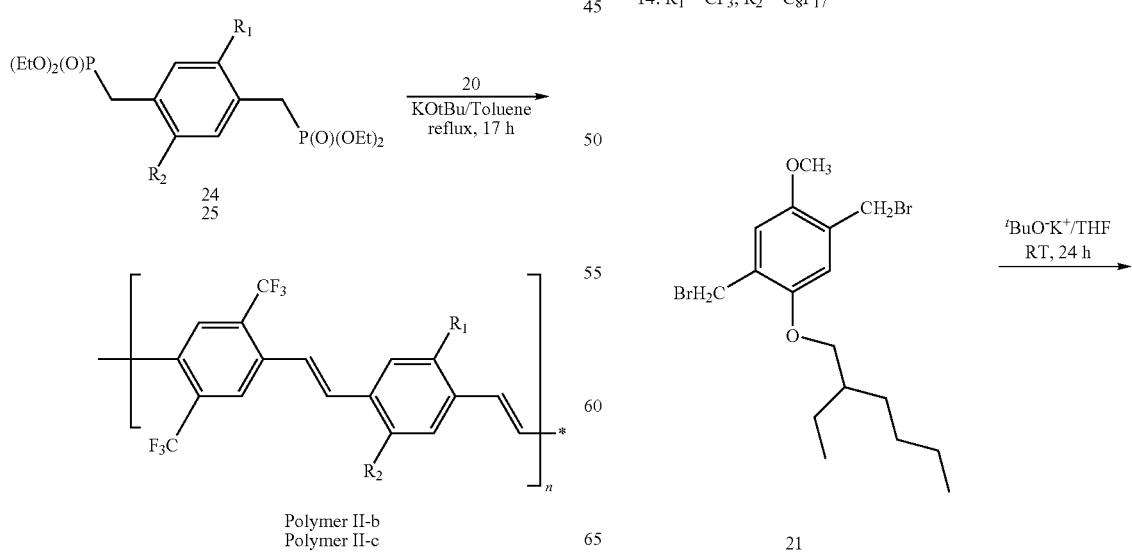

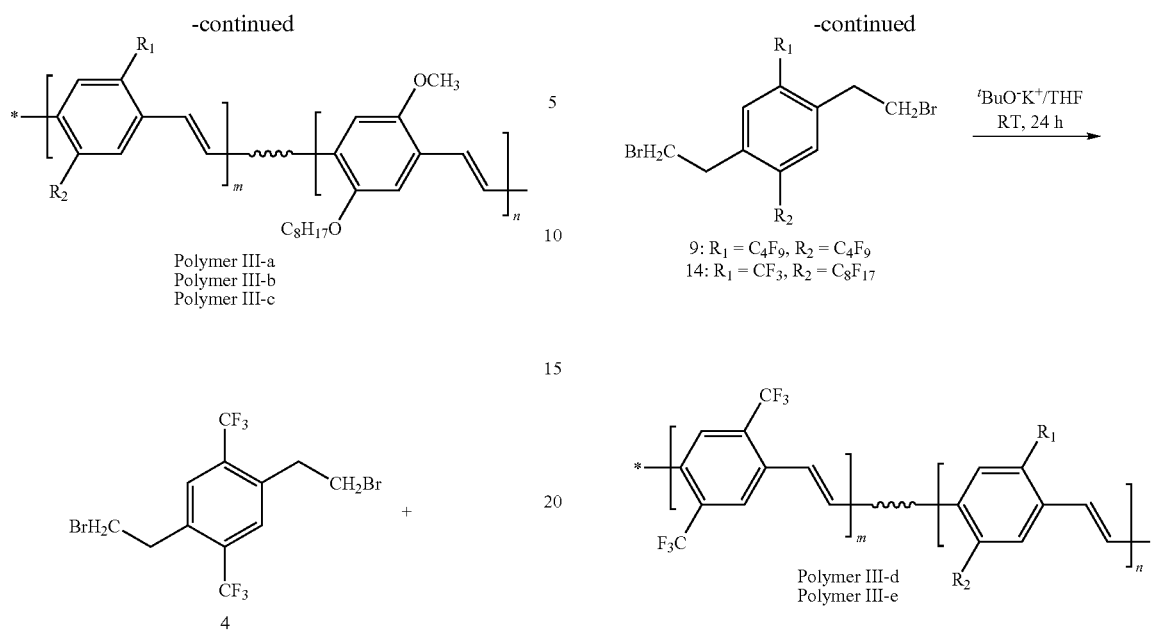
9: $R_1 = C_4F_9, R_2 = C_4F_9$
14: $R_1 = CF_3, R_2 = C_8F_{17}$
Polymer III-d
Polymer III-e
Scheme 14. Synthesis of perfluorinated alkyl PPE.
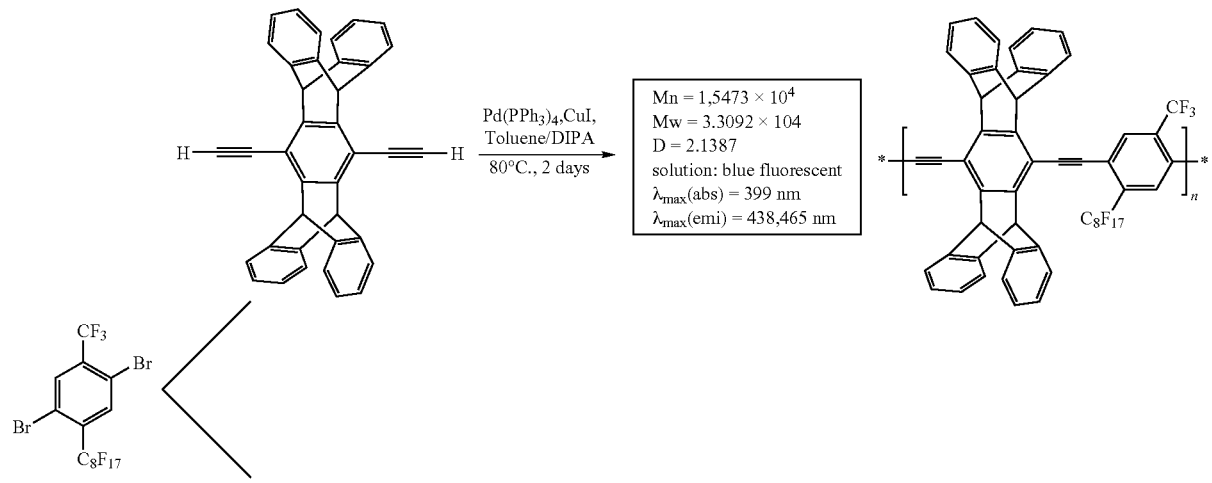
Mn = 1,5473 × 10⁴
Mw = 3.3092 × 10⁴
D = 2.1387
solution: blue fluorescent
$\lambda_{max}$(abs) = 399 nm
$\lambda_{max}$(emi) = 438,465 nm
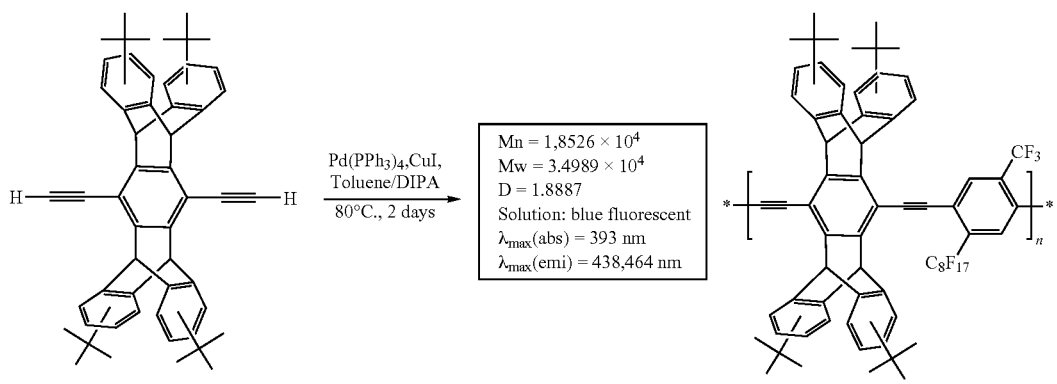
Mn = 1,8526 × 10⁴
Mw = 3.4989 × 10⁴
D = 1.8887
Solution: blue fluorescent
$\lambda_{max}$(abs) = 393 nm
$\lambda_{max}$(emi) = 438,464 nm Scheme 15. A proposed synthetic route for PPEs combining both electron withdrawing group bonding modes (i.e. directly attached and not directly attached to the conjugated backbone).

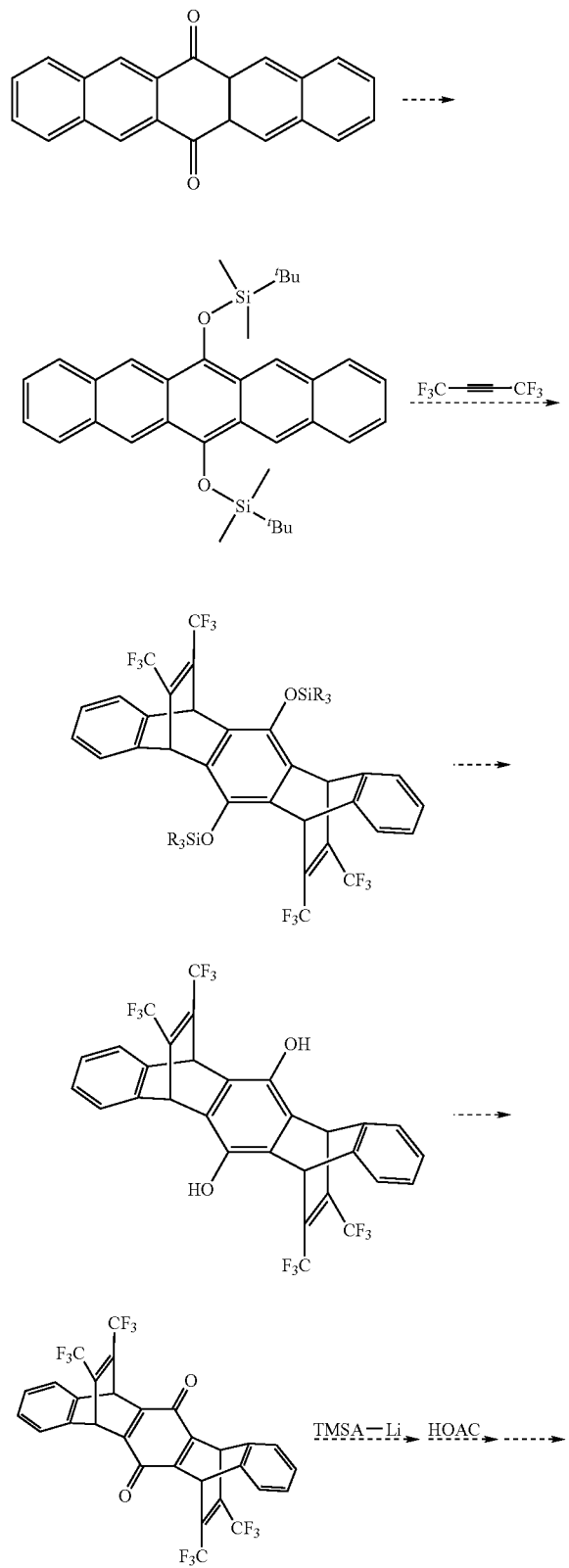

Scheme 16. A synthetic route for PPEs combining both electron withdrawing group bonding modes (i.e. directly attached and not directly attached to the conjugated backbone). Synthesis of Polymers A-F.

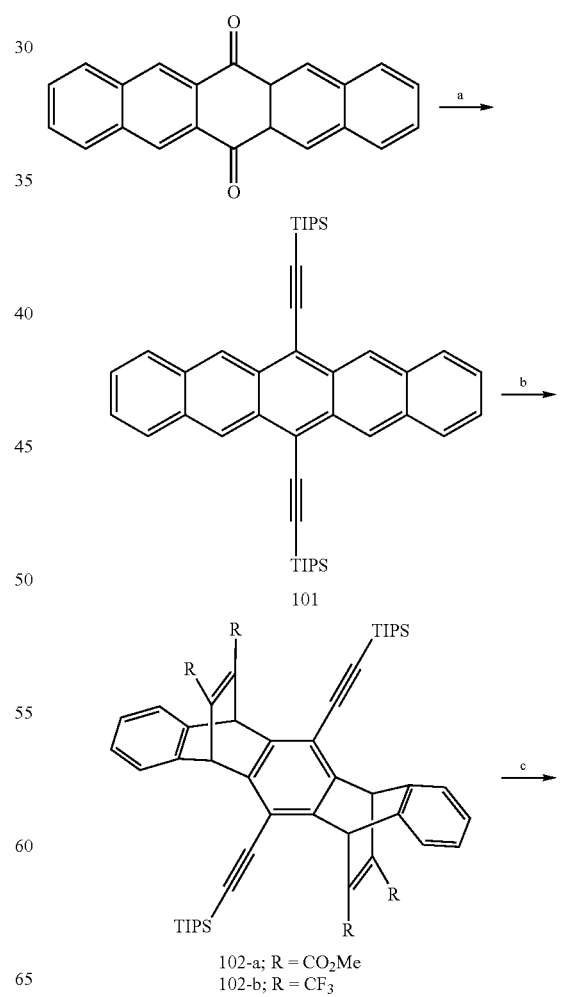

102-a; R = CO$_2$Me
102-b; R = CF$_3$

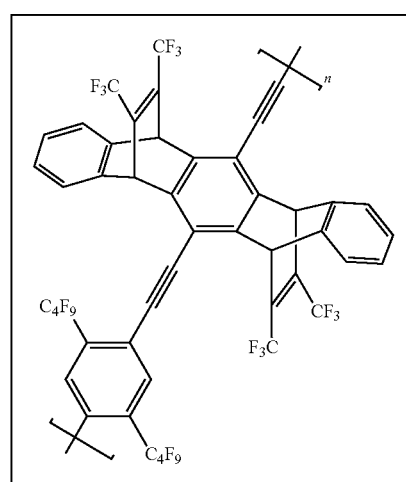

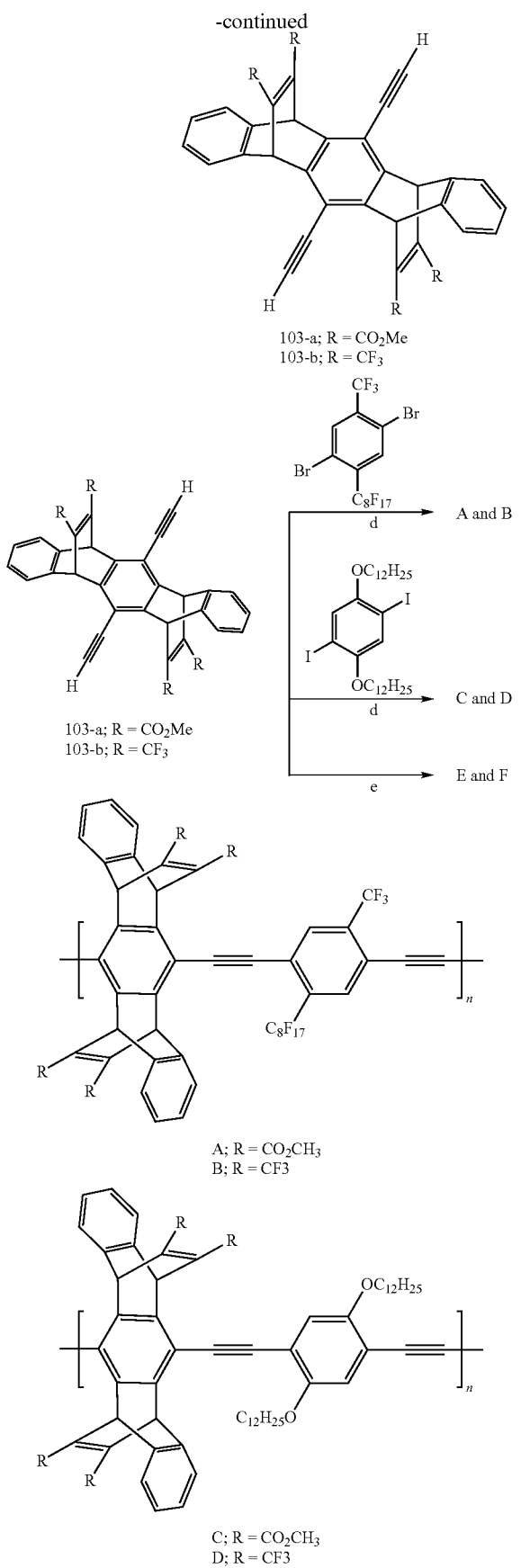

103-a; R = CO₂Me
103-b; R = CF₃

103-a; R = CO₂Me
103-b; R = CF₃

A; R = CO₂CH₃
B; R = CF₃

C; R = CO₂CH₃
D; R = CF₃

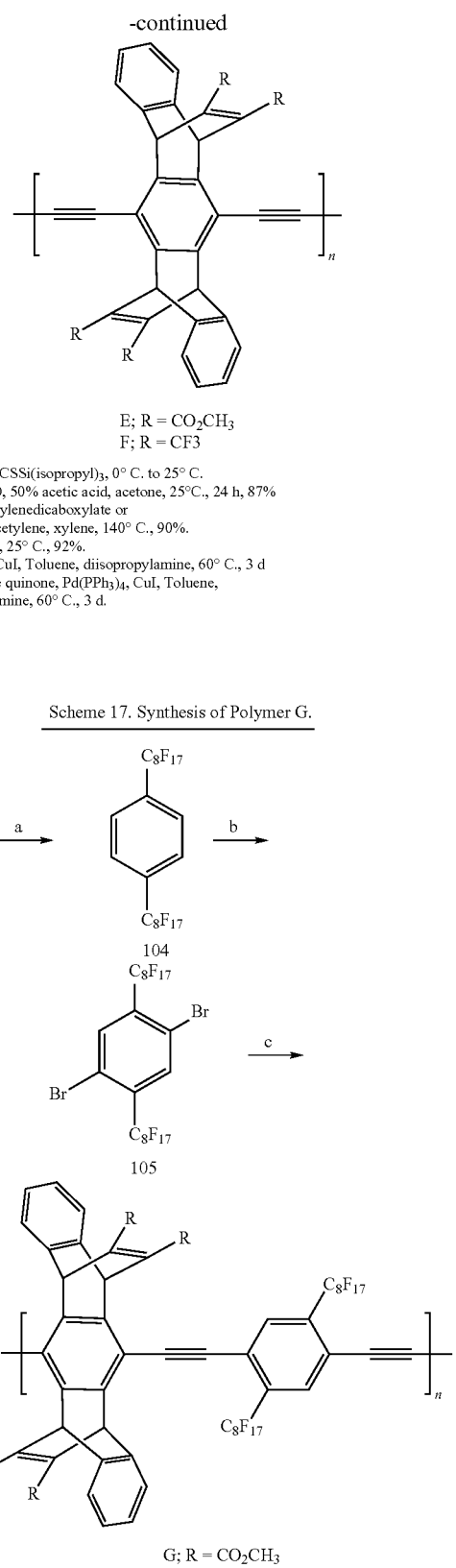

E; R = CO₂CH₃
F; R = CF₃

Key: (a) (i) LiCCSSi(isopropyl)₃, 0° C. to 25° C.
(ii) SnCl₂·2H₂O, 50% acetic acid, acetone, 25°C., 24 h, 87%
(b) dimethylacetylenedicaboxylate or
   hexafluoroacetylene, xylene, 140° C., 90%.
(c) TBAF, THF, 25° C., 92%.
(d) Pd(PPh₃)₄, CuI, Toluene, diisopropylamine, 60° C., 3 d
(e) pentiptycene quinone, Pd(PPh₃)₄, CuI, Toluene,
   diisopropylamine, 60° C., 3 d.

Scheme 17. Synthesis of Polymer G.

104

105

G; R = CO₂CH₃

Key: (a) C₈F₁₇I, Cu, DMSO, 140° C., 3 d, 20%
(b) H₂SO₄/TFA (0.3 v/v), NBS, 60° C., 2 d, 25%
(c) 3-a, Pd(PPH₃)₄, CuI, Toluene, diisopropylamine, 60° C., 3 d.

Stability of PPV Comprising Perfluorinated Alkyls

Semiconductive polymers containing perfluorinated alkyls have a high electron affinity that prevents oxidative degradation (photobleaching). Photobleaching studies reveal that the perfluoroalkyl semiconductive polymers have superior stability when compared to other semiconductive organic polymers.

Figure 6:
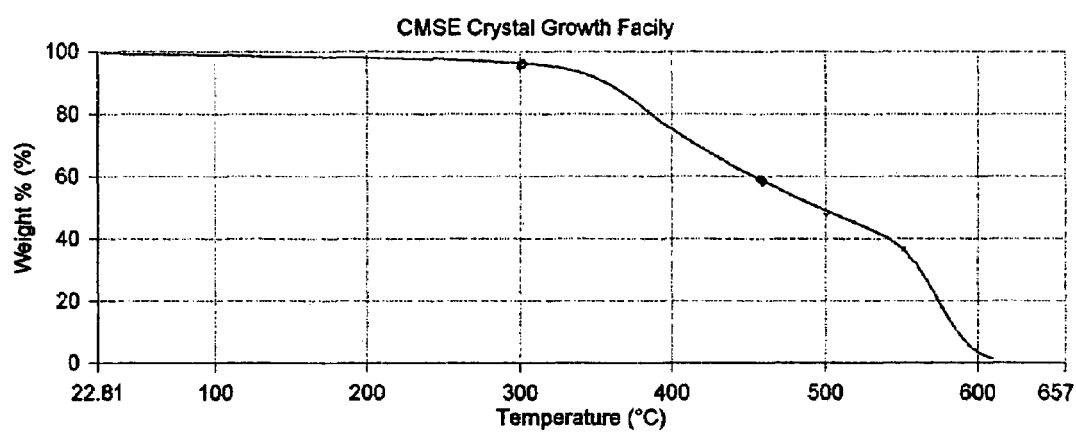
FIG. 6 depicts (top) a thermogravimetric analysis of a trifluoromethyl substituted PPV showing no weight loss up to 300° C.; and (bottom) the results of a photobleaching study of a trifouromethyl substituted PPV showing no change with excitation at 320 nm for 2.5 hours with slit widths of 20 nm.
Figure 6:
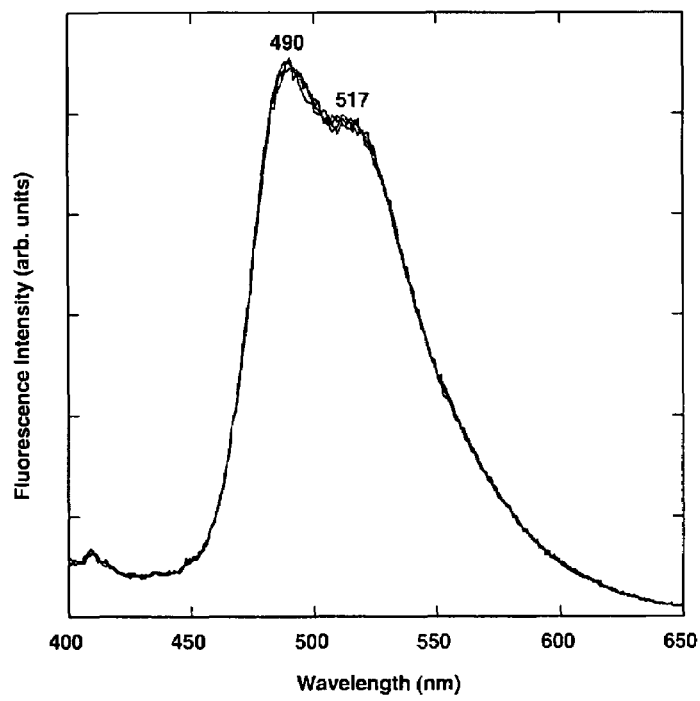
Figure 7:
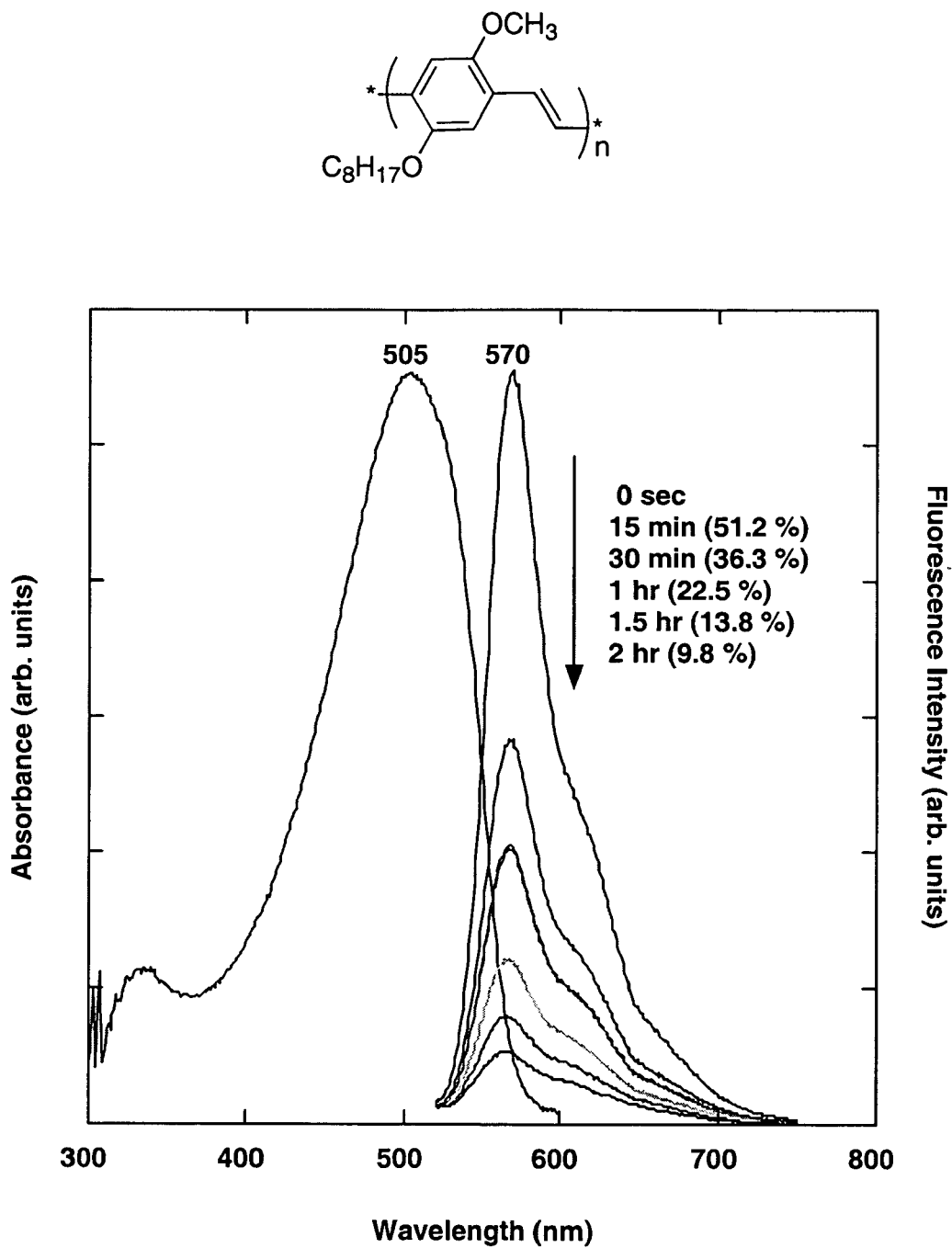
FIG. 7 depicts the extensive bleaching that occurs with MEH-PPV with excitation at 320 nm and slit widths of 20 nm in contrast to what is observed for perfluorinated alkyl PPV.
Figure 8:
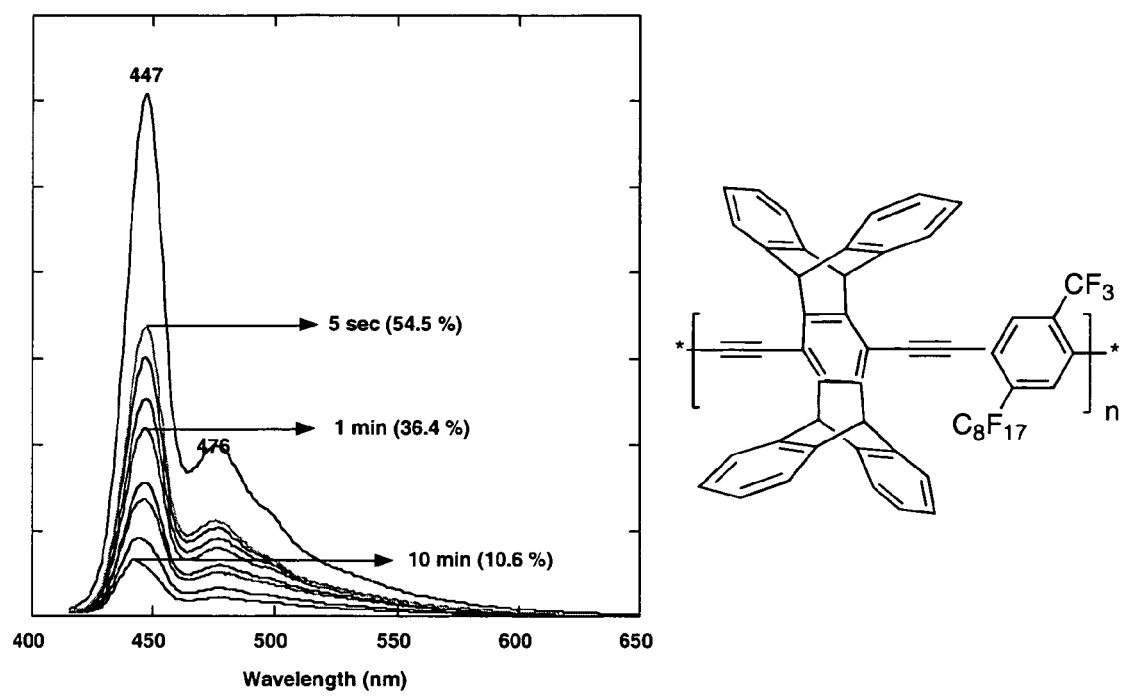
FIG. 8 depicts results from indole quenching experiments on PPEs with perfluorinated alkyls bonded directly to the conjugated backbone.

For example, photobleaching studies with UV light on trifluoromethyl containing PPV showed no change with excitation at 320 nm for 2.5 hours with slit widths of 20 nm (FIG. 6). Contrastingly, the same photobleaching experiments performed on alkoxy substituted PPV shows emissions reduced to 51.2% after just 15 min, to 36.3% after 30 min, to 22.5% after 1 hour, to 13.8% after 1.5 hours and to 9.8% after 2 hours. This extraordinary durability is unprecedented for semiconductive organic polymers and endows these materials with the critical stability needed for many sensors, photovoltaic, display, and electronic technologies. The performance of many electronic devices is expected to benefit from a reduction of the contact resistance between metal electrodes and polymers. Other polymers having strongly electron withdrawing groups used in this application are also expected to display similar stability at interfaces. In cases where electron-poor nitrogen-containing heterocyclics are present, well-defined and stable metal complexes may be formed, wherein the nitrogen atoms are bound to the metal ions.

Stable Interfaces of PPV Comprising Perfluorinated Alkyls

It is anticipated that between a metal surface and a perfluorinated alkyl polymer of the present invention a more stable interface will form than what is normally observed. It is believed that this greater stability is due to the mechanism proposed in Scheme 18 and the increased stability associated with a σ-bonds between metals and perfluorinated alkyls. Milstein, D. et al., *J. Am. Chem. Soc.,* 2001, 123, 11504.

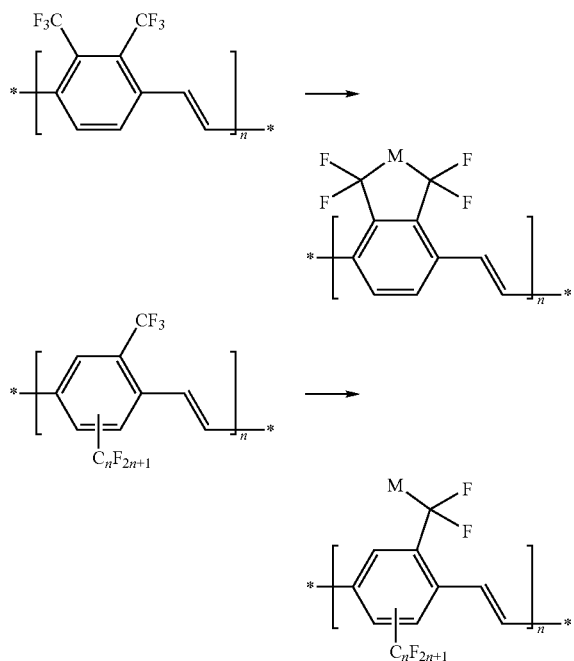

Scheme 18. Proposed route to stable metal-polymer interface.

This increased stability is important for improved OLEDs, also known as electric luminescence (EL) devices. OLEDs have advantages of high luminance, self-emission, low driving voltage, no limitation of view angle and easy fabrication. Therefore, they are applicable to planar displays. There are, however, still some difficulties associated with known OLEDs. These difficulties include, for example, lower efficiency of emission, limited luminance, and limited durability. An influencing factor for these problems is the efficiency of carrier injection. Since the OLED is a light emitter having two carrier injections wherein electrons and holes are injected from the cathode and the anode, respectively, into the organic layers where recombination occurs resulting in energy released and light emitted, the capability or efficiency of the electrode injections will highly influence the luminance and efficiency of the light emission. Therefore, it is believed that the more stable interface between the metal electrodes and perfluorinated alkyl polymers of the present invention will facilitate the charge injection processes and lead to more efficient light-emitting devices.

Fluorescence Quenching Studies

Figure 9:
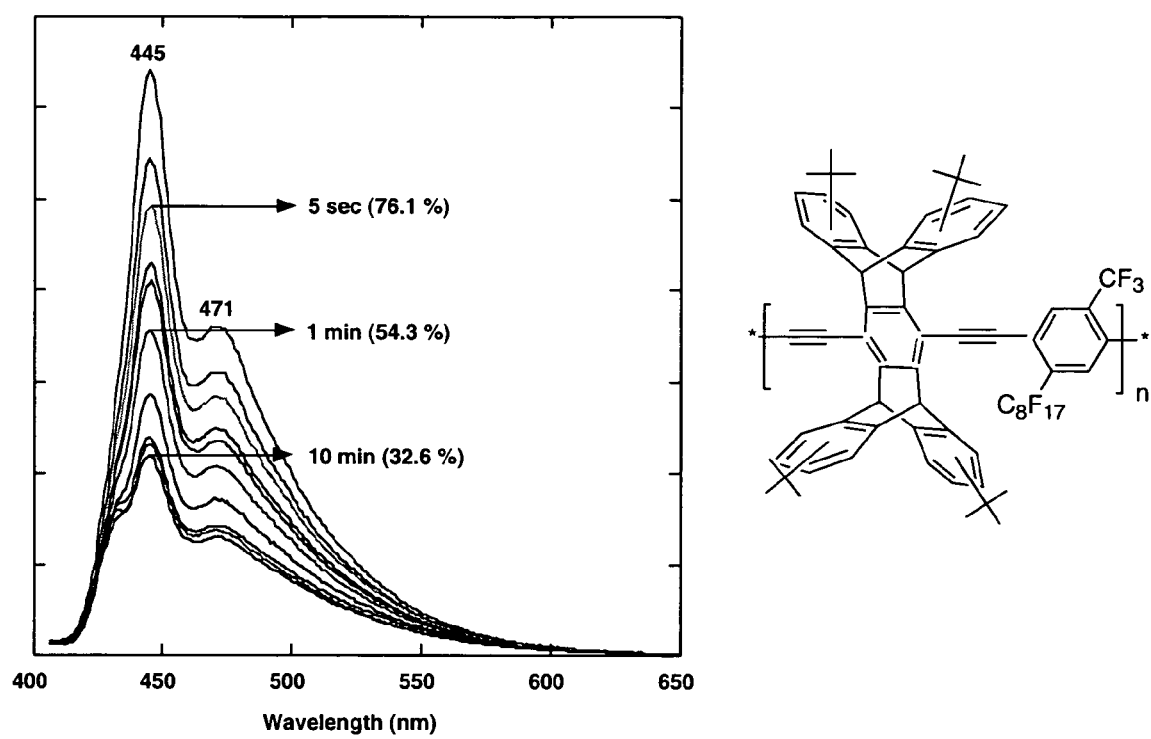
FIG. 9 depicts results from indole quenching experiments on PPEs with perfluorinated alkyls bonded directly to the conjugated backbone, wherein the PPEs are further substituted with electron donating groups.

Quenching characteristics are observed with fluorescent, semiconductive polymers which have the electron withdrawing groups directly bonded to the conjugated backbone. That is to say, quenching is observed in the presence of electron donating molecules, such as amines. Typical semiconductive organic sensory polymers do not respond to electron donating materials and hence these materials at hand have a unique sensory function. Importantly, it has been demonstrated that these materials are highly quenched by indole and the same effect is expected for tyrosine (see FIG. 9). Quenching studies measuring the effect of indole on perfluorinated alkyl substituted PPE shows a reduction in fluorescence to 54.5% in 5 seconds, to 36.4% in 1 minute, and to 10.6% in 10 minutes. Interestingly, when the same set of experiments was carried out on the same perfluorinated alkyl substituted PPE, except for the presence of t-butyl groups on the non-conjugated aryls, the reduction in fluorescence was not as great. After 5 seconds fluorescence reduced to 76.1%, after 1 minute to 54.3%, and after 10 minutes to 32.6%. This decreased quenching effect indole has on the latter PPE can be explained by the presence of the electron donating t-butyl groups which result in a more electron rich and sterically bulky system. Because the fluorescent, semiconductive polymers of the present invention quench in the presence of tyrosine and indole (present in tryptophan) it is envisioned that the fluorescent, semiconductive polymers of the present invention may be used as a general sensor for proteins. Similar results are expected from the interaction of nucleotide bases with highly electron poor polymers thereby representing a detection technology for these analytes. The detectible signal would be the reduction in fluorescence resulting from protein induced quenching. In a broader sense, any oxidizable material could potentially be detected. The basic materials could include, for example, nerve agent simulants, such as dimethyl-methyl-phosphonate (DMMP).

Study on Highly Emissive Excimers

Inter-chain interactions can significantly modify the energetics of the excited states (excitons) in conjugated polymers. For example, inter-chain interactions present in ground state give strong red shifts of the luminescence, through the formation of dimer or aggregates states. For these materials, such inter-chain interactions often produce a reduction in quantum yield for luminescence.

In the design of highly emissive materials with well-defined structures, polyphenylenethylenes (PPEs) were used for molecular scaffolds due to their efficient singlet exciton transport. We incorporated [2.2.2] bicyclic systems to rigid PPE backbone since these types of molecule are known to form inclusion complexes or dimers, depending on functional groups attached onto the system.

Figure 10:
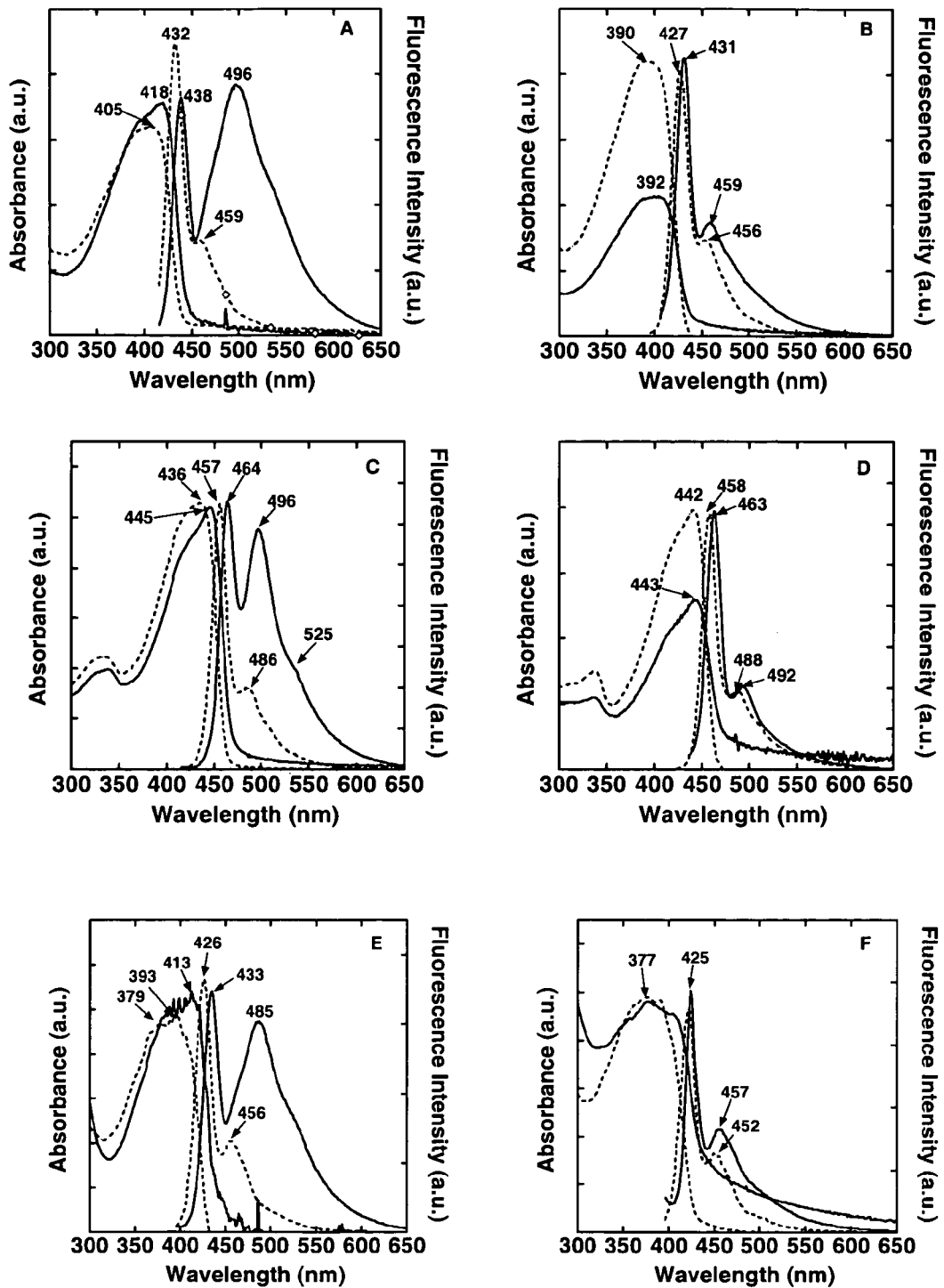
FIG. 10 depicts the absorption and emission spectra of polymers A-F in chloroform (dotted line) and solid film (solid line). All polymer samples were excited at 380 nm.
Figure 11:
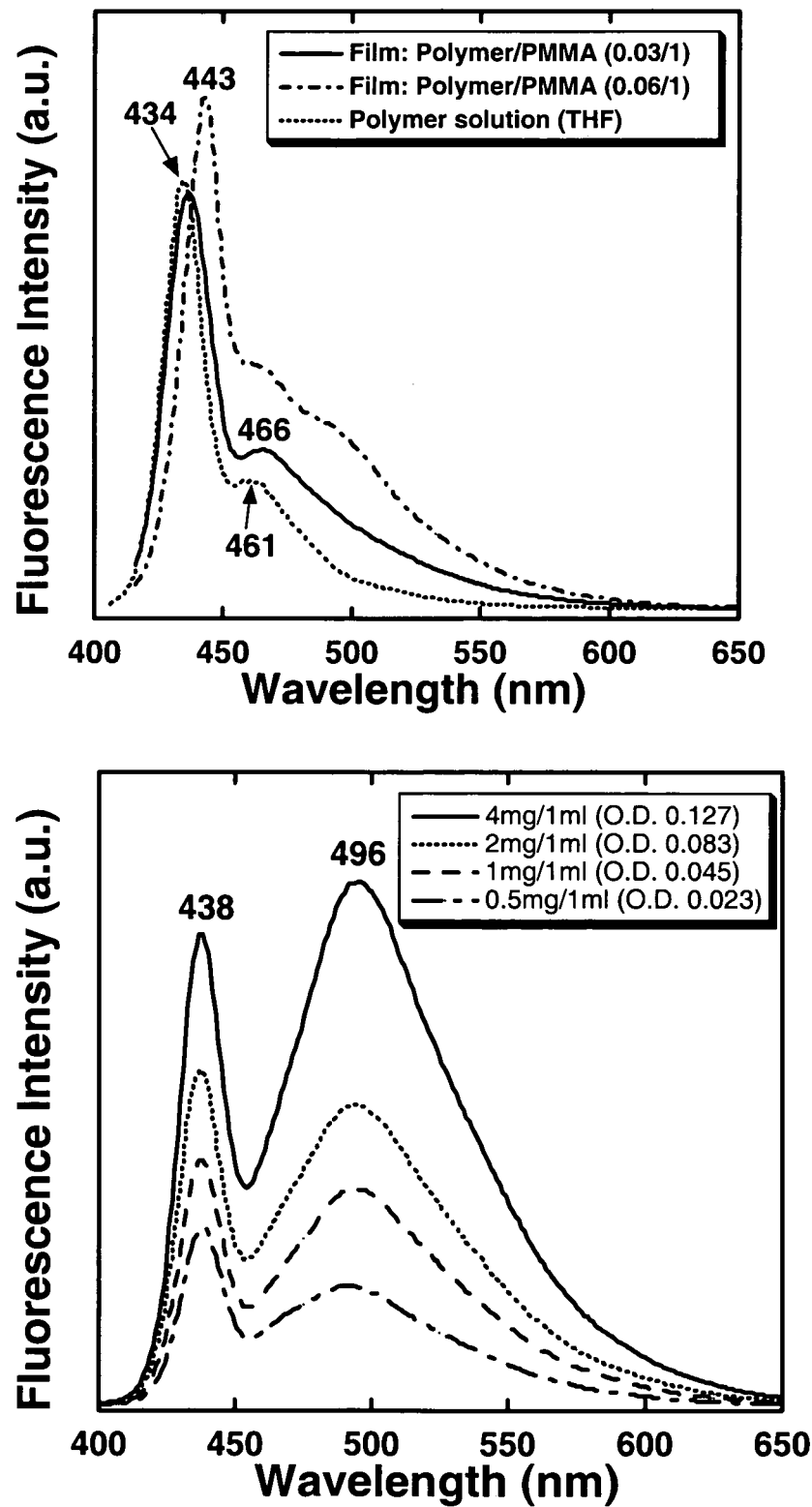
FIG. 11 depicts the fluorescence spectra of (a) polymer A films (isomer mixture) depending on film thickness (b) polymer A films in PMMA (O.D: 0.05 for 0.03/1 and 0.3 for 0.06/1) and solution.
Figure 12:
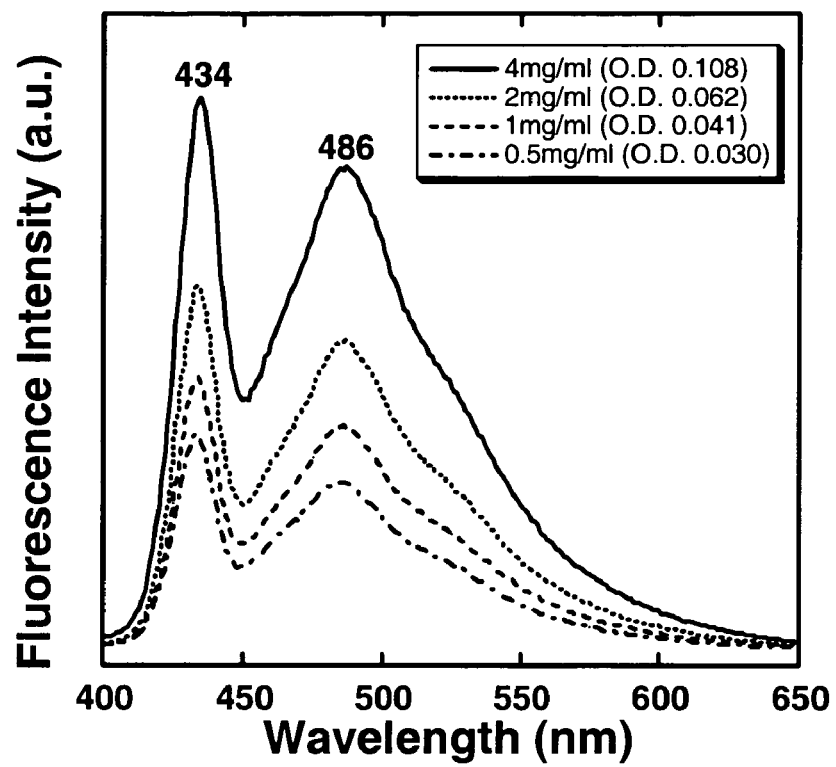
FIG. 12 depicts the fluorescence spectra of (a) polymer E films (isomer mixture) depending on film thickness (b) polymer E films in PMMA (O.D: 0.03 for 0.02/1) and solution.
Figure 12:
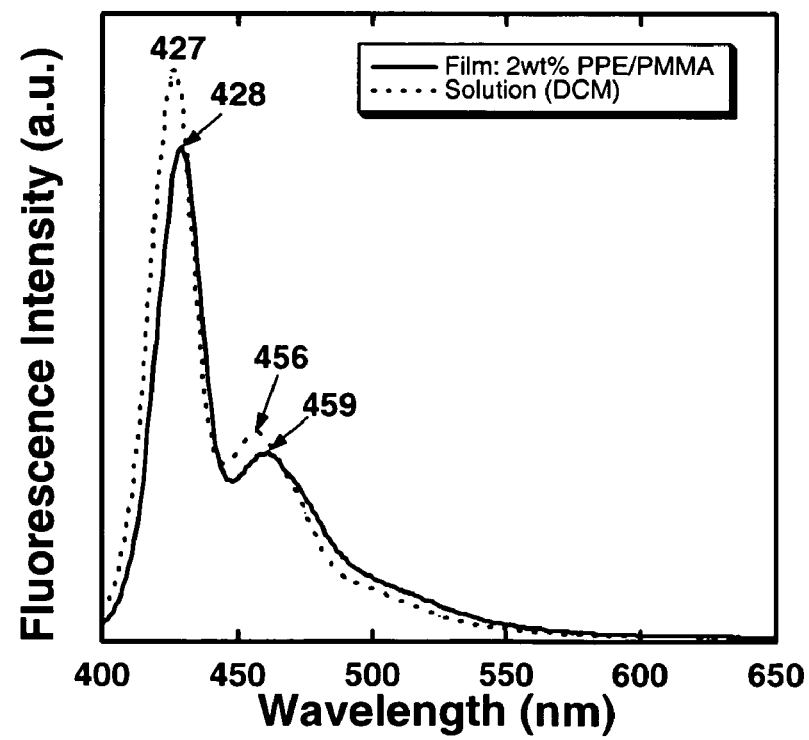

As shown in Scheme 16, the monomers 103-a and 103-b are prepared in 3 steps from pentacene quinone in high yield and copolymerized with dihalide monomers or homopolymerized by palladium catalyzed coupling reaction. The photophysical properties of polymers in solution and solid state were investigated. As shown in the absorption and emission spectra of polymers, they show small Stokes shift in solution and solid state (FIG. 10). Surprisingly, we observed unusual broad, red-shifted featureless peaks in emission spectra of polymer A and E films. Unlike aggregates, which are red-shifted in both emission and absorption, red-shifted peaks for polymer A and E films were not observed in absorption spectra. Also, their absorption and excitation spectra are similar, indicating that emissive species have the same origin. To further investigate the origin of red-shifted emission in polymer A film, fluorescence spectra were investigated by changing film thickness of polymer A film (FIG. 11(a)). As the thickness of polymer A film increased, the ratio of maximum emission intensity of peak at longer wavelength to peak at shorter wavelength increased whereas any new red-shifted peak in the absorption spectra for polymer A film was not observed. These results are consistent with strong intermolecular interactions in the excited state. In addition, spin-cast films of polymer A in poly(methyl methacrylate) (PMMA) with different weight ratios of polymer to PMMA were prepared to minimize inter-chain interaction such as excimer formation. As shown in FIG. 11(b), polymer A/PMMA (0.03/1) film behaves like solution, demonstrating that excimer formation may be avoided by reducing inter-chain interactions. Therefore, film of polymer A in a PMMA matrix is strong blue fluorescent film, whereas polymer A film without PMMA is strong green fluorescent by emissive excimer formation. On the other hand, none of these behaviors was observed for polymer B, C, D and F films, whereas this tendency to excimer formation was observed in similar PPE system such as polymer E as shown in FIGS. 10 and 12. However polymer E without perfluoroalkyl substituted aromatic unit showed less tendency to excimer formation, compared by polymer A. As a result, polymer A and E films, which showed broad red-shifted peak, may have different packing arrangements, which control the strength of the inter-chain coupling. Generally, the luminescence of polymer thin films originated from aggregation or excimer formation shows low quantum yield due to efficient self-quenching which is typical of most conjugated polymers. However, high quantum yields for polymer A in solid state (21%) as well as in solution (87%, quinine sulfate in 0.1 N $H_2SO_4$ as standard) are observed like those of polymers B both in solution (84%) and solid state (22%). The quantum yield of polymer film in PMMA (2 wt % polymer A/PMMA) is 81%, which is close value of that of polymer A solution.

Figure 13:
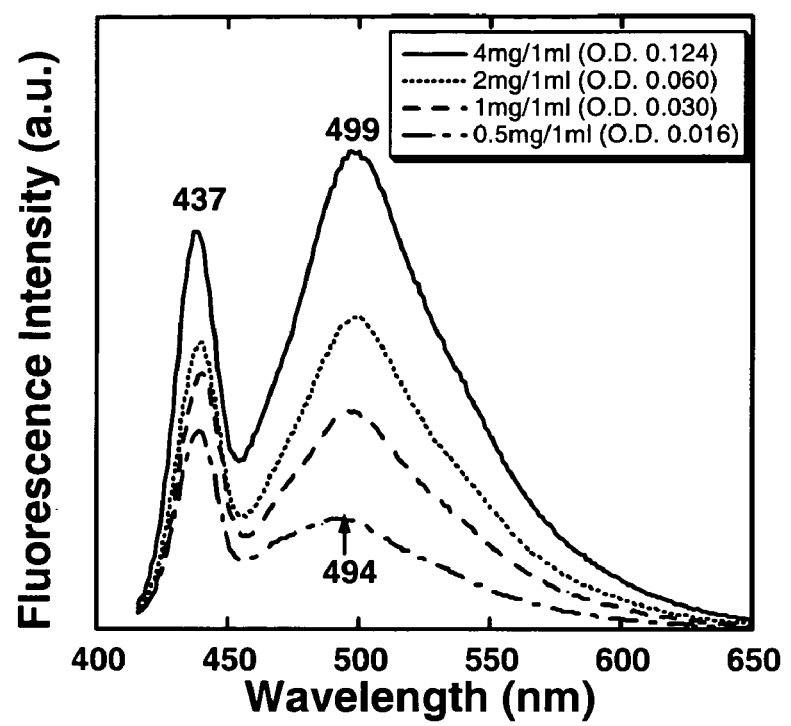
FIG. 13 depicts the fluorescence spectra of (a) syn- (b) anti-poylmer A films depending on film thickness.
Figure 13:
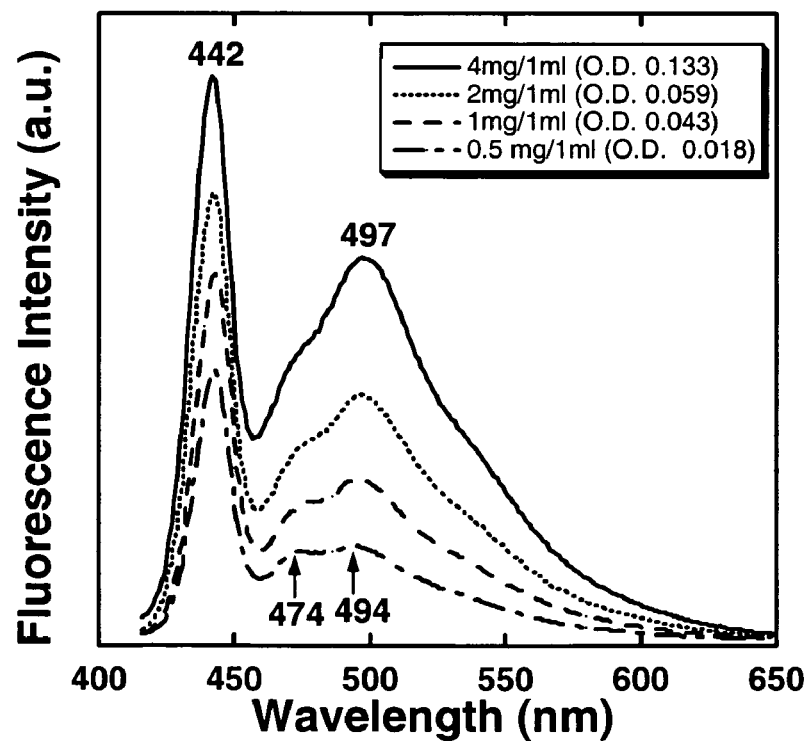
Figure 14:
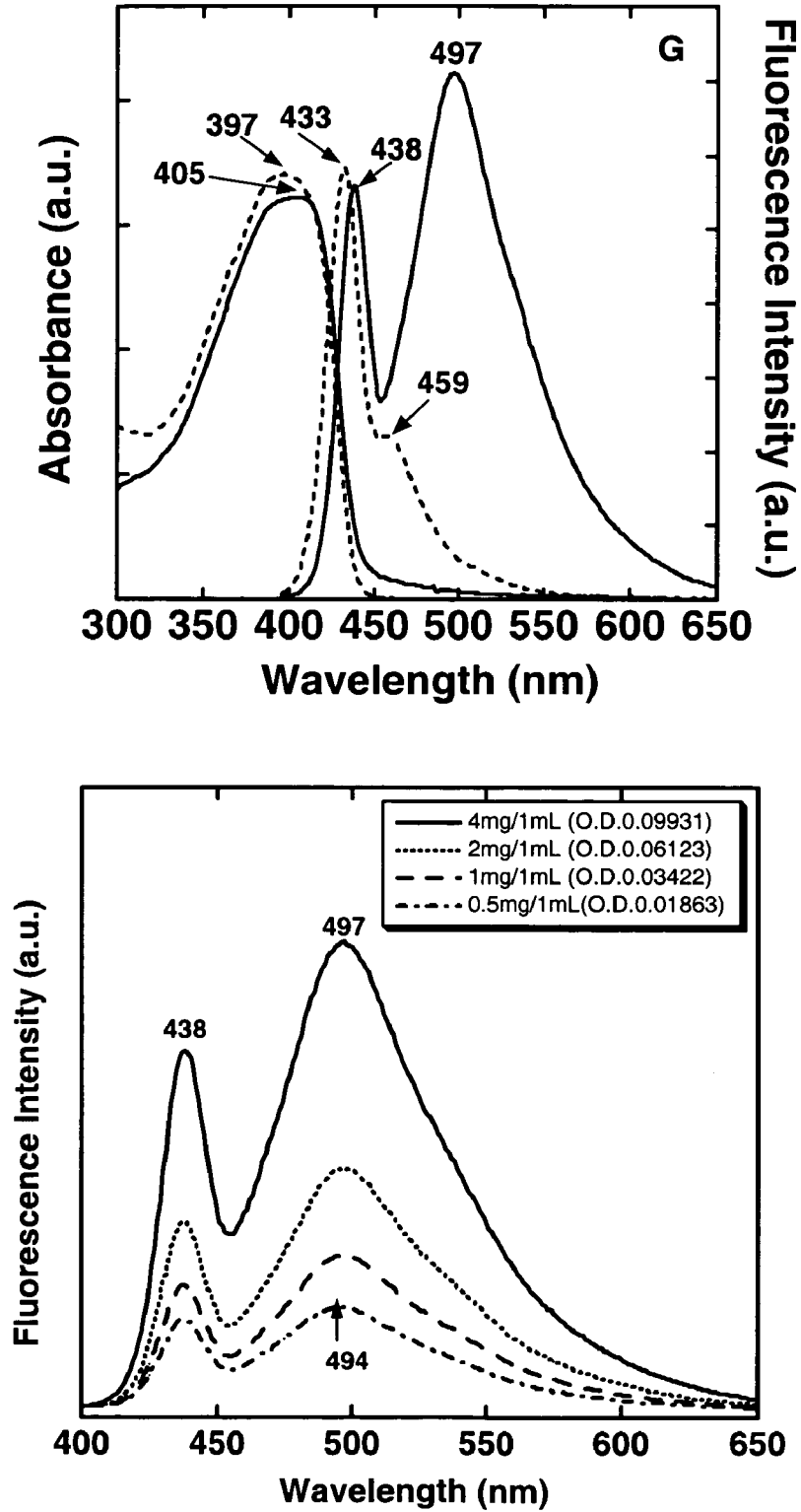
FIG. 14 depicts (a) the absorption and fluorescence spectra of poylmer G in chloroform (dotted line) and solid film (solid line) (b) the fluorescence spectra of polymer G films (anti isomer) depending on film thickness.

In order to explore the effect of conformational difference of polymer on excimer formation, absorption and emission spectra of syn- and anti-polymer A films, which copolymerized with one isomer of monomer 103-a, were investigated. As shown in FIG. 13, anti-polymer A film exhibited larger tendency to form excimer when compared to syn-polymer A film of the same optical density, suggesting that anti-conformation in polymer A film may contribute to the increase of excimer formation through a well-organized structure. Since emissive excimers were not observed in polymer films with trifluoromethyl groups on [2.2.2] bicyclic ring systems (B, D, and F) or polymer films having alkoxy substituted aromatic units (C and D) whereas polymer films with ester groups on [2.2.2] bicyclic ring systems (A and E) displayed emissive excimer formation, polymer G having bis-perfluorooctyl groups was prepared to investigate the effect of perfluorinated substituents on excimer formation as shown in Scheme 17. As shown in fluorescence spectra of polymer G thin film, much stronger tendency to excimer formation was observed when compared polymer A film with the same optical density (FIG. 13). This may be due to the contribution of perfluorinated chains to the control of inter-chain packing and the degree of intermolecular excimer formation. In summary, spectroscopic results showed the existence of low energy sites in polymer A, E and G films with ester functional groups on [2.2.2] bicyclic ring systems. These sites were better accessed by well-defined structures without reducing emission efficiency.

Determination of pI (Isoelectric Point)

Figure 15:
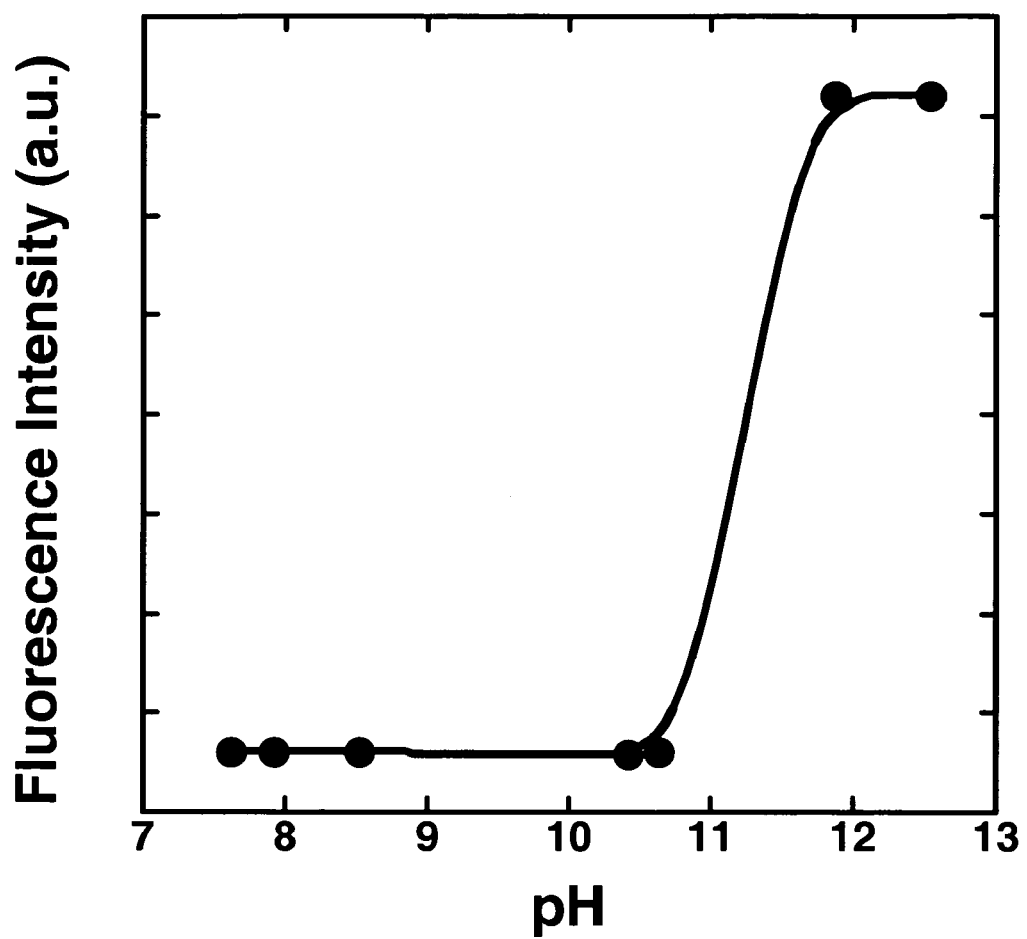
FIG. 15 depicts the emission intensity as a function of pH of polymer H containing cytochrome C (1.25 μM) in water. The pH of solution was adjusted with 0.01 N NaOH.

We are interested to see if fluorescent conjugated polymers can provide broad-spectrum of protein detection. In a preliminary experiment to demonstrate the determination of pI of protein, protein with known pI such as cytochrome C (pI 10.65) was tested with water-soluble anionic carboxylate polymer H, which was prepared by base hydrolysis of polymer A (LiOH/THF and H2O). The fluorescence intensity was monitored as a function of pH of solution, which is composed of polymer H and cytochrome C (1.25 µM) in water. At high pH (>pH 11) where both cytochrome C and polymer H are of the same charge, the association of polymer with protein is prevented; hence the fluorescence intensity of polymer H is maximized. As the charge polarity of protein is reversed, fluorescence quenching of polymer H is observed. The interpolated fluorescence quenching response of polymer H on cytochrome C is comparable to the known pI of cytochrome C (FIG. 15). This result suggests that simple titration monitoring the fluorescence of polymer as function of pH can be used to determine the pIs of proteins and such a scheme can be part of a protocol for rapidly identifying proteins.

Analyte-recognition

The present invention generally relates to organic polymers able to participate in an analyte-recognition process, where an analyte facilitates an energy transfer between an energy donor and an energy acceptor. Certain embodiments of the invention make use of fluorescent conjugated polymers, such as poly(phenylene ethynylene)s and other polymers comprising pi-conjugated backbones. In some cases, the interaction may include energy exchange mechanisms, such as Dexter energy transfer or the strong coupling effect. Another aspect of the invention provides for the detection of biological entities, for example, pathogenic bacteria such as *E. coli*, or viruses such as influenza virus. In some cases, biological recognition elements may be used to determine the biological entity, for instance, carbohydrates that can be used to specifically interact with at least part of the biological entity, such as a protein in the cell membrane of a bacterium. Still other aspects of the invention involve articles, devices, and kits using any of the above-described systems.

Various embodiments of the invention provide for the transfer of energy from a first chromophore (an energy donor) to a second chromophore (an energy acceptor). For example, energy may be transferred along a conjugated polymer between a first chromophore of the conjugated polymer and a second chromophore of the conjugated polymer. In some cases, energy within a specific range (i.e., an energy band) may be transferred between the first chromophore and the second chromophore.

In some embodiments, the first chromophore and the second chromophore may interact through an energy exchange mechanism, such as a Dexter energy transfer mechanism or the strong coupling effect. In certain embodiments of the invention, the energy exchange may occur without the substantial involvement of the well-known Förster mechanism. Such energy transfer mechanisms may be determined, for example, by exciting the chromophores at their maximum absorbance (e.g., at a wavelength or frequency where the polymer does not significantly absorb the exciting radiation), measuring quantum yield, and comparing the yield to predicted values.

Energy transfer between the first chromophore and the second chromophore may occur due to the strong coupling effect in some cases, where the chromophores interact to give a common quantum mechanical state, i.e., where the molecules containing the chromophores are close enough to create substantial or non-negligible overlap between their respective molecular wave functions. Thus, in one set of embodiments, two or more chromophores (e.g., an energy donor and an energy acceptor) may be brought into proximity such that energy transfer may occur between the chromophores through such an energy exchange mechanism. For example, two or more chromophores may be brought to within about 10 nm of each other, and in some cases, such that the chromophores are within about 5 nm of each other, within about 3 nm of each other, within about 2 nm of each other, or within about 1 nm of each other or less. In some cases, as further discussed below, the two or more chromophores may be brought in proximity with each other using specific interactions, such as protein/carbohydrate, ligand/receptor (e.g., biotin/avidin or biotin/streptavidin), etc. In certain instances, the transfer of energy through the polymer is highly distance dependent. Thus, distances between chromophores may be determined, for example, by determining the intensity of light emission.

Certain embodiments of the invention provide for the transfer of energy from an energy donor (e.g., a conjugated polymer) to an energy acceptor (e.g., an indicator) without the need for spectral overlap between the energy donor and the energy acceptor, i.e., such that the emission spectrum of the energy donor does not necessarily significantly overlap the spectrum absorption spectrum of the energy acceptor. As used herein, "spectral overlap" is given its ordinary meaning as used in the art, i.e., when two spectra are normalized and superimposed, an area exists that is simultaneously under both curves (i.e., as determined by integrals). In one embodiment of the invention, this spectral overlap is less than about 25% of the total combined area of both curves. Minimized spectral overlap is desired, but not required, and in some cases, the overlap between the two spectra may be less than about 20%, less than about 15%, less than about 10%, less than about 5%, less than about 3%, less than about 1%, less than about 0.3%, less than about 0.1%, less than about 0.03%, or less than about 0.01% or less. In certain cases, though, there may still be some overlap between both spectra, for example, an overlap of at least about 0.1%, at least about 0.3%, at least about 1%, at least about 5%, at least about 10%, at least about 15%, etc.

In another set of embodiments, the first chromophore may have a first emission lifetime and the second chromophore may have a second emission lifetime at least about 5 times greater than the first emission lifetime, and in some cases, at least about 10 times greater, at least about 15 times greater, at least about 20 times greater, at least about 25 times greater, at least about 35 times greater, at least about 50 times greater, at least about 75 times greater, at least about 100 times greater, at least about 125 times greater, at least about 150 times greater, at least about 200 times greater, at least about 250 times greater, at least about 350 times greater, at least about 500 times greater, etc.

In yet another set of embodiments, the second chromophore may enhance emission of the first chromophore, for example, by a factor of at least about 5-fold, at least about 10-fold, at least about 30-fold, at least about 100-fold, at least about 300-fold, at least about 1000-fold, at least about 3000-fold, or at least about 10,000-fold or more in some cases.

If the energy transfer includes Förster transfer, then the energy transfer may advantageously be enhanced by larger spectral overlap, according to another embodiment of the invention. That is, energy may be transferred from the first chromophore (e.g., an energy donor, such a fluorescent polymer) to the second chromophore (e.g., an energy acceptor, such as an indicator) through Förster transfer, a Dexter mechanism, or a combination of Förster transfer and a Dexter mechanism. In cases where the energy transfer can occur by a Dexter mechanism, then the amount of energy transfer will be substantially independent of the spectral overlap between the first chromophore to the second chromophore, unlike situations in which Förster transfer is the only mechanism of energy transfer between the first chromophore and the second chromophore, where the degree of energy transfer varies with the amount of spectral overlap between the first and second chromophores. Thus, in one set of embodiments, the mechanism of energy transfer between a first chromophore and a second chromophore (e.g., Dexter vs. Förster) can be determined by determining the amount that energy transfer between the first and second chromophores is enhanced by the spectral overlap. Reduced spectral overlap may allow the energy transfer to give rise to new threshold emissions in the presence of the analyte, where the new threshold emissions have minimal overlap with emissions in the absence of analyte.

In one set of embodiments, the new threshold emission may have a peak maximum of at least about 100 nm higher in wavelength than that of the dominant non-threshold emission, i.e., the first chromophore (e.g., an energy donor) and the second chromophore (e.g., an energy acceptor) may have maximum emission wavelengths that differ by at least about 100 nm. In other cases, the new threshold emission may have a peak maximum of at least about 150 nm higher in wavelength than that of the dominant non-threshold emission. In yet other cases, the new threshold emission may have a peak maximum of at least about 200 nm, about 250 nm, about 300 nm, or more higher in wavelength than that of the dominant non-threshold emission.

Energy exchange mechanisms, in some embodiments, may also enhance spatial sensitivity, allowing the use of systems and methods that cannot be performed using only conventional techniques, for example, FRET techniques (fluorescence resonance energy transfer techniques). For example, enzymes or proteins may undergo conformational changes upon binding a biomolecule or other analyte. These conformational changes can result in small changes in the positions of respective functionality of the enzyme or protein. However, as small changes in conformation can significantly reduce orbital interactions and thereby reduce or alter energy transfer between an energy donor and an energy acceptor, the systems and methods of the present invention can allow for the determination of changes in conformation of the enzyme or protein. For example, a change in conformation of an enzyme or a protein may increase or decrease energy transfer between an energy donor (e.g., a fluorescent polymer) and an energy acceptor (e.g., an indicator), which may be detected in some fashion, for example, by detecting an increase or decrease in emission from the indicator, detecting a change in the peak maximum of the emission of the indicator, etc. Thus, certain embodiments of the present invention provide for the determination of allosteric-type binding events, for example, to determine the role of proteases, co-factors, small molecules, etc., or selective hybridization events involving DNA, RNA, etc.

One aspect of the invention provides systems and methods for determining a biological entity in a sample, for example, determining the presence, type, amount, etc. of the biological entity within a sample. A sample may be exposed to one or more of the polymers described herein, for example, including conjugated polymers comprising chromophores and/or biological recognition elements, conjugated polymers capable of mulitvalent binding, etc. If the conjugated polymer comprises a chromophore such as a fluorophore, the emission or absorbance (e.g., fluorescence, phosphorescence, etc.) of the conjugated polymer may then be determined to determine the biological entity. For instance, the biological entity may facilitate an interaction between the conjugated polymer comprising the chromophore and an indicator that can be determined to determine the biological entity. The sample may be taken from any suitable source where the presence of the biological entity is to be determined, for example, from food, water, plants, animals, bodily fluids (for example lymph, saliva, blood, urine, milk and breast secretions, etc.), tissue samples, environmental samples (for example, air, water, soil, plants, animals, etc.), or the like. In one embodiment, the biological entity is a pathogen.

Exemplification

The invention now being generally described, it will be more readily understood by reference to the following examples, which are included merely for purposes of illustration of certain aspects and embodiments of the present invention, and are not intended to limit the invention.

General Methods. NMR ($^1$H and $^{13}$C) spectra were recorded on Varian Mercury 300 MHz or Bruker Avance 400 MHz spectrometers. The chemical shift data for each signal are given in units of δ(ppm) relative to tetramethylsilane (TMS) where δ(TMS)=0, and referenced to the residual solvent. High-resolution mass spectra were obtained with a Finnigan MAT 8200 system using sector double focus and an electron impact source with an ionizing voltage of 70 V. UV-vis spectra were obtained from a Cary 50 UV-Visible Spectrophotometer. Fluorescence spectra were measured with a SPEX Fluorolog-τ3 fluorometer (model FL312, 450W xenon lamp) equipped with model 1935B polarization kit. The spectra in solution were obtained at room temperature using a quartz cuvette with a path length of 1 cm. Polymer thin film spectra were recorded by front-face (22.5°) detection. Fluorescence quantum yields of polymers in THF solution were determined relative equal-absorbing solutions of quinine sulfate ($\Phi_F$=0.53 in 0.1 N sulfuric acid). The quantum yields for solid-state thin films were obtained relative to 0.01 mol % 9,10-diphenylanthracene in PMMA ($\Phi_F$=0.83) as a reference. The time decay of fluorescence was determined by a phase-modulation method, using frequencies from 10 to 300 MHz. The molecular weights of polymers were determined by using a PLgel 5 μm Mixed-C (300×7.5 mm) column and a diode detector at 254 nm at a flow rate of 1.0 mL/min in THF. The molecular weights were reported relative to polystyrene standards purchased from Polysciences, Inc. Polymer thin films on a cover glass (18×18 mm) were spin cast on a EC101DT photoresist spinner (Headway Research, Inc.) using a spin rate of 3000 rpm from THF solution. Melting point (m.p.) determination was performed using a Laboratory Devices MEL-TEMP instrument (open capillaries used) and was uncorrected.

Materials. All solvents were spectral grade unless otherwise noted. Anhydrous THF, xylene, isopropanol and carbon tetrachloride were purchased from Aldrich Chemical Co., Inc. All other compounds including analytes (Aldrich) were used as received. All air and water-sensitive synthetic manipulations were performed under an argon atmosphere using standard Schlenk techniques.

EXAMPLE 1

1,4-Dimethylanthracene (1)

To a solution of 1,4-dimethylanthraquinone (1 g, 4.24 mmol) suspended in 40 mL of isopropanol was added sodium borohydride (1.6 g, 42.4 mmol) in portions over 1 h at room temperature with stirring. The reaction mixture was left to stir at this temperature for an additional 30 min before heating to reflux overnight. The solution was then cooled to room temperature and quenched by pouring into 5% HCl solution. The mixture was left to stir for 1 hr and the solution was filtered to give a yellow solid. The solid was further recrystallized from ethanol to give the product 1 as a bright yellow solid (0.795 g, 92%): m.p. 70-72° C. (lit[1]. m.p. 74° C.); $^1$H NMR (300 MHz, CDCl$_3$): 8.56 (2H, s), 8.06 (2H, dd, J=6.5 and 3.3 Hz), 7.50 (2H, dd, J=6.5 and 3.3 Hz), 7.22 (2H, s), 2.82 (6H, s); HR-MS (EI) calcd. for C$_{16}$H$_{14}$ (M$^+$): 206.11, found: 206.11.

EXAMPLE 2

9,10-Dihydro-9,10-(1',2'-dicarbomethoxy)etheno-1, 4-dimethyl anthracene (2a)

To a solution of 1,4-dimethylanthracene 1 (0.55 g, 2.67 mmol) in 10 mL xylene was added dimethylacetylenedicarboxylate (1.90 g, 13.34 mmol) at room temperature and stirred at 140° C. for 24 h. The mixture was allowed to cool to room temperature and the reaction solvent was removed under vacuum to give a solid. Further purification by recrystallization from a mixture of dichloromethane and methanol (1:3) gave the product 2a as a white solid (0.84 g, 90%): m.p. 139-140° C.; $^1$H NMR (300 MHz, CDCl$_3$): 7.38 (2H, dd, J=5.4 and 3.0 Hz), 7.03 (2H, dd, J=5.4 and 3.0 Hz), 6.75 (2H, s), 5.72 (2H, s), 3.81 (6H, s), 2.46 (6H, s); $^{13}$C NMR (75 MHz, CDCl$_3$): 166.2, 147.3, 144.0, 142.1, 130.1, 126.8, 125.6, 124.0, 52.8, 49.6, 18.7; HR-MS (EI) calcd. for C$_{22}$H$_{20}$O$_4$ (M$^+$): 348.14, found: 348.13.

EXAMPLE 3

9,10-Dihydro-9,10-(1',2'-bis(trifluoromethyl)) etheno-1,4-dimethyl anthracene (2b)

m.p. 155-156° C.; $^1$H NMR (300 MHz, CDCl$_3$): 7.41 (2H, dd, J=5.4 and 3.0 Hz), 7.07 (2H, dd, J=5.4 and 3.0 Hz), 6.79 (2H, s), 5.67 (2H, s), 2.44 (6H, s); $^{13}$C NMR (75 MHz, CDCl$_3$): 167.3, 143.2, 141.3, 130.3, 127.2, 126.1, 124.1, 48.1, 18.3; HR-MS (EI) calcd. for C$_{20}$H$_{14}$F$_6$ (M$^+$): 368.0994, found: 368.0995.

EXAMPLE 4

1,4-Bis(2-ethylhexyloxy)-5,8-Dimethyl-9,10-dihydro-9,10[1', 2']benzenoanthracene (2d)

1,4-dimethylanthracene (4.10 g, 19.87 mmol) and 1,4-benzoquinone (3.22 g, 29.9 mmol) was refluxed in xylenes for 40 min. Solvent was removed in vacuo and the residue were separated by flash chromatography (with polarity ramped from hexanes to 1:1 hexane:dichloromethane). The fraction containing benzenoanthracene-1,4-dione was separated, dried and redissolved in acetic acid. The solution was heated to reflux and a drop of hydrobromic acid was added. Reflux was continued for 30 min and solvent was removed under vacuum. The residue was purified by chromatography (1:10 ethyl acetate/dichloromethane) to afford 5,8-Dimethyl-9,10-dihydro-9,10[1',2']benzenoanthracene-1,4-diol (4.9 g, 79%): HR-MS (EI) calcd for $C_{22}H_{18}O_2$ (M$^+$): 314.1307, found: 314.1313. This material was used in subsequent reactions without further characterizations. 5,8-Dimethyl-9,10-dihydro-9,10[1',2']benzenoanthracene-1,4-diol (8.3 g, 26.4 mmol) was dissolved in DMF (30 mL) and sodium hydride (60% suspension in mineral oil, 4.2 g, 0.11 mol) was added in small portions. The reaction mixture was stirred for 30 min under nitrogen and 2-ethylhexyl bromide (17.8 g, 0.092 mol) was added. The reaction mixture was heated for 16 h at 100° C. and the solvent was removed. The residue was purified by column chromatography (1:10 dichloromethane/hexane) to afford the product 2d as an amorphous solid (9.90 g, 70%). $^1$H NMR (300 MHz, CDCl$_3$): 7.42 (2H, m), 7.02 (2H, m), 6.75 (2H, s), 6.50 (2H, s), 6.18 (2H, s), 3.87 (2H, s), 3.85 (2H, s), 2.53 (6H, s), 1.86 (2H, m), 1.72-1.44 (18H, m), 1.07-0.96 (12H, m); $^{13}$C NMR (75 MHz, CDCl$_3$): 148.47, 146.09, 144.04, 135.63, 135.59, 129.60, 126.12, 124.92, 123.81, 109.36, 109.25, 71.10, 44.12, 40.00, 39.93, 31.22, 31.14, 29.60, 19.45, 24.51, 24.48, 23.50, 23.46, 18.61, 18.58, 14.48, 11.74, 11.58; HR-MS (EI) calcd for $C_{38}H_{50}O_2$ (M$^+$): 538.3811, found: 538.3824.

EXAMPLE 5

9,10-Dihydro-9,10-(1',2'-dicarbomethoxy)etheno-1, 4-bis(bromomethyl) anthracene (3a)

A mixture of the methyl ester 2a (200 mg, 0.575 mmol), N-bromosuccinimide (214 mg, 1.2 mmol) and 3 mg AIBN in 5 mL carbon tetrachloride was stirred under reflux for 24 h. The mixture was cooled to room temperature and filtered to remove salts. The filtrate was washed with CCl$_4$ and the solution was evaporated to give a crude product. This was purified by column chromatography (5:1 hexane/ethyl acetate as eluant) to give 3a as a white powder (174 mg, 60%): m.p. 168-170° C.; $^1$H NMR (300 MHz, CDCl$_3$): 7.53 (2H, dd, J=5.0 and 3.0 Hz), 7.09 (2H, dd, J=5.0 and 3.0 Hz), 6.98 (2H, s), 5.92 (2H, s), 4.75 (2H, d, J=10.2 Hz), 4.55 (2H, d, J=10.2 Hz), 3.84 (6H, s); $^{13}$C NMR (75 MHz, CDCl$_3$): 166.0, 147.0, 145.0, 143.0, 133.1, 126.8, 126.3, 124.8, 53.0, 49.4, 30.4; HR-MS (EI) calcd. for $C_{22}H_{18}O_4Br_2$ (M$^+$): 503.9566, found: 505.9524.

EXAMPLE 6

9,10-Dihydro-9,10-(1',2'-bis(trifluoromethyl)) etheno-1,4-bis(bromomethyl)-anthracene (3b)

This compound was prepared in a similar procedure as 3a except that benzene was used as a solvent and benzoyl peroxide was used as the initiator. m.p. 168-170° C.; $^1$H NMR (300 MHz, CDCl$_3$):7.53 (2H, dd, J=5.1 and 3.0 Hz), 7.12 (2H, dd, J=5.1 and 3.0 Hz), 7.02 (2H, s), 5.87 (2H, s), 4.71 (2H, d, J=10.5 Hz), 4.53 (2H, d, J=10.5 Hz); $^{13}$C NMR (75 MHz, CDCl$_3$):144.0, 142.2, 133.3, 127.3, 126.6, 124.9, 47.9, 29.6; HR-MS (EI) calcd. for $C_{20}H_{12}F_6Br_2$ (M$^+$): 523.92, found: 523.92.

EXAMPLE 7

1,4-Bis(2-ethylhexyloxy)-5,8-bis(bromomethyl)-9, 10-dihydro-9,10[1',2']benzeno-anthracene (3d)

Compound 2d (1.37 g, 2.54 mmol), N-bromosuccimide (0.996 g, 5.60 mmol) and benzoyl peroxide (5.0 mg) were refluxed in benzene (100 mL) for 8 h. The solvent was removed and the residue was purified by column chromatography (1:4 dichloromethane/hexane) to afford the product 3d as an amorphous solid (1.07 g, 61%): $^1$H NMR (300 MHz, CDCl$_3$): 7.48 (2H, m), 7.02 (2H, m), 6.92 (2H, s), 6.51 (2H, s), 6.31 (2H, s), 4.84 (2H, m), 4.53 (2H, m), 3.88 (4H, s), 1.82 (2H, s), 1.65-1.38 (18H, m), 1.07-0.96 (12H, m); $^{13}$C NMR (75 MHz, CDCl$_3$): 148.50, 146.54, 144.70, 134.42, 134.38, 132.36, 126.00, 125.34, 124.28, 109.88, 109.78, 71.40, 71.37, 43.89, 39.97, 39.92, 31.30, 31.28, 30.51, 29.62, 29.50, 24.61, 24.56, 23.51, 23.49, 14.52, 14.50, 11.77, 11.66; HR-MS (EI) calcd for $C_{38}H_{48}Br_2O_2$: 694.2021, found: 694.2001.

EXAMPLE 8

Polymer 4a

Compound 3a (60 mg, 0.12 mmol) was placed in a 25 mL Schlenk flask with a stir bar. The flask was evacuated and back-filled with argon three times, followed by the addition of dry THF (3 mL). Under an atmosphere of argon, an excess of potassium t-butoxide (1 M solution in THF, 0.59 mmol) was added to the reaction solution and this was left to stir for 2 hours at room temperature. The reaction mixture was then precipitated into a mixture of methanol and water (10:1). The polymer 4a (30 mg, 73%) was collected by filtration as a yellow-orange solid: $^1$H NMR (300 MHz, CDCl$_3$): 8.0-7.8 (2H, br), 7.7-7.4 (4H, br), 7.2-6.9 (2H, br), 6.4-6.1 (2H, br), 1.6-1.4 (18H, br); $M_n$=123 kDa, PDI=2.5.

EXAMPLE 9

Polymer 4b $^1$H NMR (300 MHz, CDCl$_3$): 7.9-7.6 (6H, br), 7.4-7.3 (2H, br), 6.4-6.2 (2H, br); $M_n$=684 kDa, PDI=2.5.

EXAMPLE 10

Polymer 4d $^1$H NMR (300 MHz, CDCl$_3$): 7.8-6.5 (m, br, 12H), 3.8 (br, 4H), 1.5-0.86 (m, br, 30H); $M_n$=890 kDa, PDI=1.7.

EXAMPLE 11

1,4-bis(trifluoromethyl)-2,5-dibromobenzene (1)

Into a 1000 mL round-bottomed flask were placed 250 mL trifluoroacetic acid, 1,4-bis(trifluoromethyl)benzene (19 g, 88.7 mmol), and 60 mL sulfuric acid (98%). The mixture was stirred vigorously and NBS (47.4 g, 267 mmol) was added in portions at 60° C. over 5-hour period. After stirring at the temperature for 2 d, the mixture was poured into 500 mL of ice-water. The precipitates were filtered and sublimed to give a white solid (30 g, 91%): m.p. 64-65° C.; $^1$H NMR (300 MHz, CDCl$_3$): 8.01 (2H, s); $^{13}$C NMR (75 MHz, CDCl$_3$): 134.3, 123.4, 119.7, 119.3; $^{19}$F NMR (282 MHz, CDCl$_3$): −64.4; HR-MS (EI) calcd. for $C_8H_2F_6Br_2$ (M$^+$): 369.8422, found: 369.8529.

EXAMPLE 12

1,4-bis(trifluoromethyl)-2,5-dibenzoic acid (2)

At −75° C., precooled tetrahydrofuran (80 mL) and compound 1 (12.5 g, 33.6 mmol) dissolved in THF (60 mL) were consecutively added to n-butyllithium (2.5 M solution in hexane, 30 mL, 75 mmol). A white precipitate formed instaneously. After 30 min of vigorous stirring at −75° C., the mixture was poured on freshly crushed dry ice. The reaction mixture was diluted with diethyl ether (150 mL) and the organic layer was extracted with 2 M NaOH (3×50 mL). The acid was collected as a white powder after acidification with 2 M HCl of the aqueous phase and recrystallized from hexane to give a white solid (7 g, 70%): m.p.>230° C.; $^1$H NMR (300 MHz, CDCl$_3$): 8.34 (2H, s), 2.06 (2H, s); $^{13}$C NMR (75 MHz, CDCl$_3$): 165.1, 134.7, 131.8, 129.1, 124.5; $^{19}$F NMR (282 MHz, CDCl$_3$): −61.5; HR-MS (ESI) calcd. for C$_{16}$H$_{14}$ ([M−H]$^-$): 300.99, found: 300.99.

EXAMPLE 13

1,4-bis(trifluoromethyl)-2,5-dihydroxymethylbenzene (3)

Compound 2 (10 g, 33 mmol) was placed into Schlenk flask and followed by the addition of THF (150 mL). Into the resulting solution was added BH$_3$-THF (1 M solution in THF, 86.1 mL) dropwise at 0° C. After stirring at room temperature for 48 h, a mixture of diethyl ether (100 mL) and water (100 mL) was added to the reaction mixture. The organic layer was separated, washed with water (3×50 mL) and dried over MgSO$_4$. The solid was purified by column chromatography (5:1 hexane/ethyl acetate as eluant) to afford compound 3 as a white solid (7.1 g, 79%): $^1$H NMR (300 MHz, Acetone-d$_6$): 8.14 (2H, s), 4.87 (4H, s), 2.83 (2H, s); $^{19}$F NMR (282 MHz, Acetone-d$_6$): −62.1; HR-MS (EI) calcd. for C$_{10}$H$_8$F$_6$O$_2$ (M$^+$): 274.0423, found: 274.0412.

EXAMPLE 14

1,4-bis(trifluoromethyl)-2,5-dibromomethylbenzene (4)

At 0° C., PBr$_3$ (10.4 mL, 109 mmol) was slowly added to compound 3 (5 g, 18 mmol) dissolved in THF (125 mL). The reaction mixture was stirred for 30 min at 0° C. and then stirred for 40 h at room temperature. After the addition of water (20 mL) to quench the reaction under ice-bath, organic layer was diluted with diethyl ether (100 mL). The organic layer was washed with water (3×100 mL), dried over anhydrous MgSO$_4$, evaporated, and sublimed to give compound 4 as a white solid (4.6 g, 65%): m.p. 80-81° C.; $^1$H NMR (300 MHz, CDCl$_3$): 7.89 (2H, s), 4.65 (4H, s); $^{13}$C NMR (75 MHz, CDCl$_3$): 137.1, 130.8, 124.9, 121.3, 27.1; $^{19}$F NMR (282 MHz, CDCl$_3$): −61.2; HR-MS (EI) calcd. for C$_{10}$H$_6$F$_6$Br$_2$ (M$^+$): 397.8735, found: 397.8744.

EXAMPLE 15

1,4-bis(trifluoromethyl)-2,5-dichloromethylbenzene (5)

Tosyl chloride (3.9 g, 20.4 mmol), 4-dimethylaminopyridine (936.3 mg, 7.7 mmol), and distilled triethylamine (1.73 mL, 12.4 mmol) were added sequentially to a solution of compound 3 in dichloromethane (30 mL) under Ar at room temperature. The reaction mixture was stirred at this temperature for 4 h. The resulting solution was evaporated and the residue was diluted with hexane (100 mL). The organic layer was washed with water (3×50 mL), dried over anhydrous MgSO$_4$, evaporated, and purified by column chromatography (hexane as eluant) to give product 5 as a white solid (700 mg, 62%); $^1$H NMR (300 MHz, CDCl$_3$): 7.98 (2H, s), 4.78 (4H, s); $^{19}$F NMR (282 MHz, CDCl$_3$): −60.6; HR-MS (EI) calcd. for C$_{10}$H$_6$F$_6$Cl$_2$ (M$^+$): 309.9745, found: 309.9738.

EXAMPLE 16

2,5-bis(trifluoromethyl)-1,4-xylene-bis(triphneylphosphonium bromide) (6)

Triphenylphosphine (730 mg, 2.75 mmol) was added to compound 4 (500 mg, 1.25 mmol) dissolved in DMF (5 mL) at room temperature. The reaction mixture was stirred and heated to reflux for 24 h. After cooling to room temperature, this solution was poured into 150 mL dried ethyl acetate. The precipitate was then filtered, washed with diethyl ether and dried in vacuo to give a white solid 6 (786 mg, 95%).

EXAMPLE 17 oligomer (7)

A solution of sodium ethoxide (30.6 mg, 0.45 mmol) dissolved in abs. ethanol (2 mL) was added dropwise to a solution of compound 6 (60 mg, 0.09 mmol) dissolved in chloroform (2 mL) with stirring at room temperature. 2,5-Bis(trifluoromethyl)benzaldehyde (43.9 mg, 0.18 mmol) was then added to the reaction mixture. After stirring at room temperature overnight, the reaction was quenched by the addition of water. The solvent was removed in vacuo, the residue was dissolved in dichloromethane (30 mL), and the organic layer was washed with water (3×20 mL), dried over MgSO$_4$, and concentrated in vacuo again. The crude product was purified by column chromatography (hexane as eluant) to afford compound 7 as a white solid (34 mg, 56%): $^1$H NMR (300 MHz, CDCl$_3$): 7.86 (2H, d), 7.63 (2H, d), 7.16 (4H, s), 7.13 (1H, d), 7.09 (1H, d), 7.02 (1H, d), 6.99 (1H, d); $^{19}$F NMR (282 MHz, CDCl$_3$): −61.9, −62.4, −64.5; HR-MS (EI) calcd. for C$_{28}$H$_{12}$F$_{18}$(M$^+$): 690.0646, found: 690.0670; $\lambda_{max}$ (abs, CHCl$_3$)=313 nm, $\lambda_{max}$(emi, CHCl$_3$)=393, 413 nm.

EXAMPLE 18

2,5-bis(perfluorobutyl)-p-xylene (8)

A solution of C$_4$F$_9$I (0.96 mL, 5.6 mmol) was added dropwise over 10 min to a stirred mixture of 2,5-diiodo-ρ-xylene (0.5 g, 1.4 mmol), copper powder (1.4 g, 22.4 mmol) in DMSO (10 mL) at 130° C. The reaction mixture was subsequently stirred for a further 24 h at this temperature. After cooling to room temperature, it was poured into a beaker containing dichloromethane (30 mL) and water (30 mL). After filtering, the organic layer was separated, washed with water (3×30 mL) and dried over MgSO$_4$. The residue was purified by column chromatography (hexane as eluant) to give the product 8 as a white solid (553 mg, 73%).

EXAMPLE 19

2,5-bis(perfluorobutyl)-1,4-dibromomethylbenzene (9)

A mixture of compound 8 (200 mg, 0.37 mmol), N-bromosuccinimide (138 mg, 0.78 mmol) and AIBN (2 mg, 0.01 mmol) in carbon tetrachloride (5 mL) was stirred under reflux for 24 h. The mixture was cooled to room temperature and filtered to remove salts. The filtrate was washed with $CCl_4$ and the solution was evaporated to give a crude product. This was purified by recrystallization from hexane to give 9 as a white solid (100 mg, 39%): $^1$H NMR (300 MHz, $CDCl_3$): 7.82 (2H, s), 4.62 (4H, s); $^{19}$F NMR (282 MHz, $CDCl_3$): −81.6, −107.6, −121.9, −125.9; HR-MS (EI) calcd. for $C_{16}H_6F_{18}Br_2$ ([M]$^+$): 697.85, found ([M]$^+$): 697.87.

EXAMPLE 20

4-(perfluorooctyl)-α,α,α-trifluorotoluene (10)

A solution of $C_8F_{17}I$ (12 g, 22 mmol) was added dropwise over 10 min to a stirred mixture of 4-iodobenzotrifluoride (3 g, 11 mmol), copper powder (5.6 g, 0.088 mmol), 2,2'-bipyridine (120 mg, 0.8 mmol), DMSO (30 mL) at 70° C. The reaction mixture was subsequently stirred for a further 72 h at this temperature. After cooling to room temperature, it was poured into a beaker containing ether (100 mL) and water (100 mL). After filtering, the organic layer was separated, washed with water (3×50 mL) and dried over $MgSO_4$. Sublimation gave the product 10 as a white solid (5.6 g, 90%): $^1$H NMR (300 MHz, $CDCl_3$): 7.77 (4H, dd, J=8.1 and 8.4 Hz); $^{19}$F NMR (282 MHz, $CDCl_3$): −64.0, −81.4, −111.6, −121.4, −122.0, −122.1, −122, 9, −126, 3.

EXAMPLE 21

1-perfluorooctyl-4-trifluoromethyl-2,5-dibromobenzene (11)

Into a 500 mL round-bottomed flask were placed 120 mL trifluoroacetic acid, compound 10 (12 g, 21.3 mmol), and 36 mL sulfuric acid (98%). The mixture was stirred vigorously and NBS (11.4 g, 63.8 mmol) was added in portions at 60° C. over 5-hour period. After stirring at the temperature for 2 d, the mixture was poured into 200 mL of ice-water. The precipitates were filtered and sublimed to give a white solid 11 (13.5 g, 88%): $^1$H NMR (300 MHz, $CDCl_3$): 8.04 (1H, s), 7.92 (1H, s).

EXAMPLE 22

1-perfluorooctyl-4-trifluoromethyl-2,5-dibenzoic acid (12)

At −75° C., precooled tetrahydrofuran (20 mL) and compound 11 (3 g, 4.16 mmol) dissolved in THF (20 mL) were consecutively added to n-butyllithium (2.5 M solution in hexane, 3.66 mL, 9.14 mmol). After stirring at −75° C. for 60 min, the mixture was poured into freshly crushed dry ice. The reaction mixture was diluted with diethyl ether (100 mL) and the organic layer was extracted with 2 M NaOH (3×30 mL). The acid was collected as a white powder after acidification with 2 M HCl of the aqueous phase and recrystallized from hexane to give a white solid 12 (1.65 g, 61%): $^1$H NMR (300 MHz, $CDCl_3$): 8.27 (1H, s), 8.26 (1H, s), 2.07 (2H, s); $^{19}$F NMR (282 MHz, $CDCl_3$): −61.5, −82.3, −106.2, −119.4, −121.5, −122.6, −123.5, −126.9.

EXAMPLE 23

1-perfluorooctyl-4-trifluoromethyl-2,5-dihydroxymethylbenzene (13)

Compound 12 (294 mg, 0.45 mmol) was placed into Schlenk flask and followed by the addition of THF (5 mL). Into the resulting solution was added $BH_3$-THF (1 M solution in THF, 1.17 mL) dropwise at 0° C. After stirring at room temperature for 48 h, a mixture of diethyl ether (10 mL) and water (10 mL) was added to the reaction mixture. The organic layer was separated, washed with water (3×10 mL) and dried over $MgSO_4$. The solid was purified by column chromatography (5:1 hexane/ethyl acetate as eluant) to afford compound 13 as a white solid (284 mg, 51%): $^1$H NMR (300 MHz, Acetone-$d_6$): 8.26 (1H, s), 8.26 (1H, s), 4.92 (2H, s), 4.90 (2H, s), 2.86 (2H, s); $^{19}$F NMR (282 MHz, Acetone-$d_6$): −62.6, −82.3, −106.7, −121.5, −122.2, 122.6, −123.5, −126.9.

EXAMPLE 24

1-perfluorooctyl-4-trifluoromethyl-2,5-dibromomethylbenzene (14)

At 0° C., $PBr_3$ (0.24 mL, 2.54 mmol) was slowly added to compound 13 (317 mg, 0.51 mmol) dissolved in THF (10 mL). The reaction mixture was stirred for 30 min at 0° C. and then stirred for 40 h at room temperature. After the addition of water (2 mL) to quench the reaction under ice-bath, organic layer was diluted with diethyl ether (20 mL). The organic layer was washed with water (3×10 mL), dried with anhydrous $MgSO_4$, evaporated, and sublimed to give compound 14 as a white solid (240 mg, 63%): $^1$H NMR (300 MHz, $CDCl_3$): 7.90 (1H, s), 7.79 (1H, s), 4.64 (2H, s), 4.62 (2H, s); $^{19}$F NMR (282 MHz, $CDCl_3$): −61.3, −81.3, −107.1, −120.8, −121.5, 122.0, −122.9-126.3; HR-MS (ESI) calcd. for $C_{17}H_6F_{20}Br_2$ ([M−H]$^-$): 746.8433, found ([M−HBr+$CH_3$]$^-$: 682.92.

EXAMPLE 25

2-(perfluorodecyl)-p-xylene (15)

A solution of $C_{10}F_{21}I$ (4.2 g, 6.5 mmol) was added dropwise over 10 min to a stirred mixture of 2-bromo-ρ-xylene (1 g, 5.4 mmol), copper powder (1.9 g, 29.7 mmol), DMSO (80 mL) at 130° C. The reaction mixture was subsequently stirred for a further 2 d at this temperature. After cooling to room temperature, it was poured into a beaker containing dichloromethane (50 mL) and saturated potassium iodide solution (50 mL). After filtering, the organic layer was separated, washed with water (3×30 mL) and dried over $MgSO_4$. Recrystallization from hexane gave the product 15 as a white solid (2.7 g, 82%): $^1$H NMR (300 MHz, $CDCl_3$): 7.31 (1H, s), 7.24 (1H, d, J=8.1 Hz)), 7.17 (1H, d, J=8.1 Hz)), 2.46 (3H, t, J=3.0 Hz)), 2.39 (3H, s); $^{19}$F NMR (282 MHz, $CDCl_3$): −81.4, −106.7, −121.1, −121.8, −122.0, −122.9, −126.3; HR-MS (EI) calcd. for $C_{18}H_9F_{21}$ (M$^+$): 624.0363, found: 624.0353.

EXAMPLE 26

2-(perfluorodecyl)-1,4-dibromomethylbenzene (16)

A mixture of compound 15 (648 mg, 1.04 mmol), N-bromosuccimide (406 mg, 2.28 mmol) and AIBN (5.1 mg, 0.03 mmol) in carbon tetrachloride (15 mL) was stirred under reflux for 24 h. The mixture was cooled to room temperature and filtered to remove salts. The filtrate was washed with $CCl_4$ and the solution was evaporated to give a crude product. This was purified by recrystallization from hexane to give 16 as a white powder (550 mg, 68%): $^1$H NMR (300 MHz, $CDCl_3$): $^{19}$F NMR (282 MHz, $CDCl_3$): −81.3, −106.5, −120.8, −121.5, −121.9, −122.9, −126.3; HR-MS (EI) calcd. for $C_{18}H_7F_{21}Br_2$ ([M−H]$^+$): 778.8495, found ([M−H]$^+$): 778.8518.

EXAMPLE 27 poly-[2,5-bis(trifluoromethyl)-ρ-phenylene vinylene] (Polymer I-a)

Compound 4 (360 mg, 0.9 mmol) was placed in a 50 mL Schlenk flask with a stir bar. The flask was evacuated and back-filled with argon three times, followed by the addition of dry THF (15 mL). Under an atmosphere of argon, an excess of potassium t-butoxide (1 M solution in THF, 2.7 mL) was added to the reaction mixture and this was left to stir for 24 h at room temperature. The resulting solution was then poured into a mixture of methanol and water (10/1, 250 mL). The polymer 5 (150 mg, 71%) was collected by filtration as a sparingly soluble yellow-orange solid: $^1$H NMR (300 MHz, THF-$d_6$): 8.5-8.3 (1H, br), 8.0-7.8 (1H, br), 5.7-5.5 (2H, br); $M_n$=13 kDa, PDI=1.9; $\lambda_{max}$(abs, THF)=374 nm, $\lambda_{max}$(emi, THF)=489, 519 nm.

poly-[2,5-bis(perfluorobutyl)-ρ-phenylene vinylene] (Polymer I-b)

Mn=5,005, PDI=1.04; $\lambda_{max}$(abs, THF)=320 nm, $\lambda_{max}$(emi, THF)=440 nm.

poly-[1-perfluorooctyl-4-trifluoromethyl-ρ-phenylene vinylene] (Polymer I-c)

Mn=3,040, PDI=1.16; $\lambda_{max}$(abs, THF)=354 nm, $\lambda_{max}$(emi, THF)=470, 496 nm.

poly-[2-(perfluorodecyl)-ρ-phenylene vinylene] (Polymer I-d)

Mn=1,800, PDI=1.40; $\lambda_{max}$(abs, DMF)=378 nm, $\lambda_{max}$(emi, DMF)=488 nm.

EXAMPLE 28

1,1'-[2,5-bis(trifluoromethyl)-1,4-phenylene-bis(methylene)]-bis[tetrahydrothiopheni-um] dibromide (17a)

Tetrahydrothiophene (0.27 mL, 3 mmol) was added to a suspension of compound 4 (200 mg, 0.5 mmol) in dry methanol (5 mL). The solid was dissolved to form a clear solution within 10 min. This solution was filtered via 0.45 μm membrane filter and then heated to 50° C. with stirring for 24 h. After cooling down to room temperature, the solvent was completely removed in vacuo and cold acetone (10 mL) was added to the residue. The precipitate was then filtered and dried to give compound 17a as a colorless, hygroscopic solid (192 mg, 67%): $^1$H NMR (300 MHz, $D_2O$): 8.17 (2H, s), 4.76 (4H, s), 3.52-3.62 (8H, m), 2.34-2.47 (8H, m); $^{19}$F NMR (282 MHz, $D_2O$): −60.2; HR-MS (EI) calcd. for $C_{18}H_{22}F_6S_2Br_2$ (M$^+$): 573.94, found ([M-Br]$^+$): 495.04.

poly-[2,5-bis(trifluoromethyl)-1,4-phenylene vinylene] (18a)

To a deoxygenated solution of compound 17a (267 mg, 0.46 mmol) in a mixture of water (2 mL) and methanol (1 mL) cooled in an ice bath was added dropwise an ice-cold aqueous sodium hydroxide solution (1 M, 0.46 mL) over 10 min. The reaction mixture was stirred at 0° C. for 8 h under Ar and then neutralized with 0.5 M HCl (0.5 mL). The solution was then dialyzed against water over 3 days (3×500 mL), after which the solvent was completely removed.

Polymer I-a

Thin films of polymer I-a could be obtained by spin-coating the precursor polymer solution 18a by thermal conversion at 200° C. and 10$^{-6}$ mbar for 5 h: $\lambda_{max}$(emi)=485, 513 nm.

EXAMPLE 29

1,4-bis(trifluoromethyl)-2,5-diiodobenzene (19)

To a solution of 30 mL $H_2SO_4$ was added periodic acid (3.18 g, 14 mmol) and potassium iodide (6.90 g, 42 mmol) under ice bath and then 1,4-bis(trifluoromethyl)benzene (2.17 mL, 14 mmol) was added. The reaction mixture was then stirred at 70° C. for 5 h. After cooling down to room temperature, the resulting solution was poured into ice-water and then extracted with diethyl ether (100 mL) and 10% sodium thiosulfate (50 mL). The organic layer was washed with 10% sodium thiosulfate (3×50 mL), dried over $MgSO_4$, filtered, and concentrated. The residue was recrystallized from hexane to give 19 as a white solid (4.24 g, 65%): $^1$H NMR (300 MHz, $CDCl_3$): δ 8.20 (s, 2H); $^{19}$F N (282 MHz, $CDCl_3$): −64.2; HR-MS (EI) calcd. for $C_8H_2F_6I_2$ (M$^+$): 465.81, found: 465.8387.

EXAMPLE 30 poly-[2,5-bis(trifluoromethyl)-ρ-phenylene vinylene] (Polymer I-a)

A mixture of compound 19 (30 mg, 0.06 mmol), bis(tributylstannyl)ethylene (36.4 mg, 0.06 mmol), tri(t-butylphosphine) (0.73 mg, 0.004 mmol), tri(dibenzylideneacetone)dipalladium (0.82 mg, 0.001 mmol), and LiCl (5.1 mg, 0.12 mmol) dissolved in NMP was stirred at 80-100° C. for 48 h. The reaction mixture was cooled to room temperature and then extracted with chloroform and water. The organic layer was evaporated and the collected precipitate was washed with methanol to give sparingly soluble polymer I-a. GPC data was obtained from soluble portion in THF: $M_n$=2,650, PDI=1.05. $\lambda_{max}$(abs, $CHCl_3$)=339 nm, $\lambda_{max}$(emi, $CHCl_3$)=406, 423 nm.

EXAMPLE 31

2,5-bis(trifluoromethyl)-1,4-benzenedicarboxyaldehyde (20)

At −75° C., precooled tetrahydrofuran (10 mL) and compound 1 (2 g, 5.4 mmol) dissolved in THF (10 mL) were consecutively added to n-butyllithium (1.6 M solution in hexane, 7.4 mL, 11.8 mmol). A white precipitate formed instaneously. After 30 min of vigorous stirring at −75° C., N,N-dimethylformaldehyde (3 mL, 38.8 mmol) was slowly added to the reaction mixture and then stirred for 1 h at −40° C. The dialdehyde was isolated after neutralization with 2 M HCl, ethereal extraction, and recrystallization from hexane to give a white solid 20 (539 mg, 37%): $^1$H NMR (300 MHz, $CDCl_3$): δ 10.47 (s, 2H), 8.55 (s, 2H); HR-MS (EI) calcd. for $C_{10}H_4F_6O_2$ (M$^+$): 270.01, found: 270.01.

EXAMPLE 32

2-methoxy-5-(2'-ethylhexyloxy)-1,4-xylene-bis(triphneylphosphonium bromide (22)

Triphenylphosphine (1.38 g, 5.24 mmol) was added to 1,4-bis(bromomethyl)-2((2-ethylhexyl)oxy)-5-methoxybenzene 21(1 g, 2.38 mmol) dissolved in DMF (10 mL) at room temperature. The reaction mixture was stirred and heated to reflux for 24 h. After cooling to room temperature, this solution was poured into 300 mL dried ethyl acetate. The precipitate was then filtered, washed with diethyl ether and dried in vacuo to give a white solid 22 (1.4 g, 93%).

EXAMPLE 33 poly-[(2-methoxy-5-(2'-ethylhexyloxy)-1,4-phenylene vinylene-alt-2,5-bis(trifluoro methyl)1,4-phenylene vinylene] (Polymer II-a)

Into a mixture of compound 20 (10 mg, 0.037 mmol) and 22 (24.6 mg, 0.037 mmol) dissolved in chloroform (1.5 mL) was added sodium ethoxide (12.6 mg, 0.19 mmol) dissolved in ethanol (1.5 mL). The reaction mixture was stirred at room temperature overnight. The reaction was quenched with 2% HCl solution and the solution was poured into 100 mL of methanol to give orange polymer. The polymer II-a was isolated by filteration, dried, and reprecipitated in methanol: $^1$H NMR (300 MHz, CDCl$_3$): 8.05-7.75 (2H, br), 7.55-7.20 (2H, br), 6.96-6.55 (4H, br), 3.85-3.65 (3H, br), 1.45-0.45 (17H, br); $M_n$=5,522, PDI=1.32; $\lambda_{max}$(abs, THF)=483 nm, $\lambda_{max}$(emi, THF)=531,564 nm.

EXAMPLE 34

1,4-xylene-bis(diethyl)phosphonate (24)

A mixture of bis(halomethyl)benzene 23 (1 g, 3.79 mmol) and triethylphosphite (1.64 g, 9.85 mmol) was heated to 130° C. for 1 to 1.5 h with distillation set-up to collect ethyl halide in situ. The temperature was increased to 160° C. under reduced pressure to distill the excess phosphite. The mixture was allowed to cool to room temperature and product was purified by recrystallization from ether as a white solid (700 mg, 48.9%).

EXAMPLE 35

2-perfluorooctyl-5-trifluoromethyl-1,4-xylene-bis(diethyl)phosphonate (25)

Synthetic procedure of compound 25 followed that of compound 24.

EXAMPLE 36

Polymer II-b

A mixture of compound 20 (10 mg, 0.037 mmol) and 24 (13.99 mg, 0.037 mmol) in toluene was stirred and heated to 110° C. under Ar. A solution of potassium tert-butoxide (1 M solution in THF, 0.15 mL) was added all at once into hot mixture resulting in color change. The mixture was heated to reflux for 17 h and then cooled down to room temperature. The resulting solution was diluted with toluene (10 mL) and 10% acetic acid (5 mL) was added. Organic layer was separated and washed with water until neutral. Water was removed from organic layer by Dean-Stark distillation to give insoluble orange solid (Polymer II-b).

Polymer II-c $M_n$=3,138, PDI=1.23; $\lambda_{max}$(abs, THF)=508 nm, $\lambda_{max}$(emi, THF)=549, 594 nm.

EXAMPLE 37

Polymer III-a

A solution of potassium tert-butoxide (1 M solution in THF, 0.45 mL) was added dropwise to a mixture of compound 4 (21 mg, 0.05 mmol) and compound 21 (20 mg, 0.05 mmol) in tetrahydrofuran (4.5 mL) at room temperature. After stirring at the temperature for 24 h, the resulting mixture was poured into methanol (125 mL). The precipitate was filtered out and reprecipitated from tetrahydrofuran/methanol to afford polymer III-a: $^1$H NMR (300 MHz, CDCl$_3$): 8.05-7.75 (2H, br); $M_n$=19 kDa, PDI=2.14; $\lambda_{max}$(abs, CHCl$_3$)=488 nm, $\lambda_{max}$(emi, CHCl$_3$)=548 nm.

Polymer III-b $M_n$=20 kDa, PDI=8.98; $\lambda_{max}$(abs, THF)=331, 485 nm, $\lambda_{max}$(emi, THF)=440, 564 nm.

Polymer III-c $M_n$=28 kDa, PDI=2.70; $\lambda_{max}$(abs, THF)=508 nm, $\lambda_{max}$(emi, THF)=549, 594 nm.

Polymer III-d $M_n$=8,368, PDI=2.22; $\lambda_{max}$(abs, THF)=329 nm, $\lambda_{max}$(emi, THF)=483, 508 nm.

Polymer III-e $\lambda_{max}$(abs, THF)=342 nm, $\lambda_{max}$(emi, THF)=449 nm.

EXAMPLE 38

6,13-bis(triisopropylsilylethynyl)pentacene (101)

Under an atmosphere of argon, 16.2 mL of n-butyllithium (40.5 mmol, 2.5 M solution in hexane) was added dropwise to 9.1 mL (40.5 mmol) of triisopropylsilyl acetylene in 50 mL of dry tetrahydrofuran at 0° C. The mixture was kept at 0° C. for another 40 min before it was transferred to a solution of 6,13-pentacenequinone (5 g, 16.2 mmol) in 50 mL of dry tetrahydrofuran at 0° C. The mixture was warmed to room temperature and stirred overnight. The reaction was quenched with 15 mL of 10% HCl and then subjected to a CHCl$_3$/H$_2$O workup. The solvent was removed and the resulting solid was collected by filtration. This crude solid was dissolved in 50 mL of acetone and then a solution of tin(II) chloride dihydrate (9.2 g, 40.5 mmol) in 50% of acetic acid (50 mL) was added dropwise. This mixture was stirred at room temperature for another 24 h. The resulting blue solid product was filtered. The solid was then dissolved in hexane and washed with water and sodium bicarbonate and then dried over magnesium sulfate. The hexane solution is then poured onto a silica plug, which is flushed with hexane (200 mL), followed by 9:1 hexane/methylene chloride to elute a deep blue solid (8.8 g, 92%): m.p. 220-221° C.; $^1$H NMR (300 MHz, CDCl$_3$): 9.31 (s, 4H), 7.98 (dd, J=6.6 and 3.0 Hz, 4H), 7.42 (dd, J=6.6 and 3.0 Hz, 4H), 1.39 (s, 42H); HR-MS (EI) calcd. for C$_{44}$H$_{54}$Si$_2$ (M$^+$): 638.38, found: 638.37. (lit. m.p.

210° C., Anthony, J. E.; Brooks, J. S.; Eaton, D. L.; Parkin, S. R. *J. Am. Chem. Soc.* 2001, 123, 9482-9483)

EXAMPLE 39

Compound 102a

To a solution of 6,13-bis(triisopropylsilylethynyl)pentacene 101 (1 g, 1.57 mmol) in 40 mL xylene was added dimethylacetylenedicarboxylate (1.93 mL, 15.7 mmol) at room temperature and stirred at 140° C. for 48 h. The mixture was allowed to cool to room temperature and the reaction solvent was removed under vacuum to give solid residues. The crude mixture was purified by column chromatography using 20% EtOAc in hexane as eluent to give pure mixture of two isomers (syn and anti) (1.3 g, 90%). The two isomers were separated by their solubility difference. Recrystallization using hexane gave an anti-isomer as a white solid. Further column chromatography of residue solution gave an syn-isomer as a white solid: 102a-syn; mp>300° C.; $^1$H NMR (300 MHz, CDCl$_3$): δ 7.27 (dd, J=5.4 and 3.0 Hz, 4H), 6.97 (dd, J=5.4 and 3.0 Hz, 4H), 5.90 (s, 4H), 3.79 (s, 12H), 1.29 (s, 42H); $^{13}$C NMR (75 MHz, CDCl$_3$): δ 165.6, 147.7, 143.6, 143.5, 125.8, 124.2, 115.5, 101.1, 99.7, 52.6, 51.2, 19.0, 11.6; HR-MS (EI) calcd. for C$_{56}$H$_{66}$O$_8$Si$_2$ (M$^+$):922.4291, found: 922.4263. 102a-anti; mp>300° C.; $^1$H NMR (300 MHz, CDCl$_3$): δ 7.33 (dd, J=5.4 and 3.0 Hz, 4H), 7.04 (dd, J=5.4 and 3.0 Hz, 4H), 5.89 (s, 4H), 3.73 (s, 12H), 1.29 (s, 42H); $^{13}$C NMR (75 MHz, CDCl$_3$): □165.5, 147.7, 143.6, 143.5, 125.9, 124.3, 115.5, 101.1, 99.7, 52.6, 51.1, 19.1, 11.6; HR-MS (EI) calcd. for C$_{56}$H$_{66}$O$_8$Si$_2$ (M$^+$): 922.4291, found: 922.4263.

Compound 102b

Hexafluoro-2-butyne (1.52 g, 9.39 mmol) was condensed in a 60 mL pressure tube by a dry ice/acetone cooling bath. A solution of 6,13-bis(triisopropylsilylethynyl)pentacene 101 (2 g, 3.13 mmol) in xylene (10 mL) was slowly added through a septum. The pressure tube was then capped and heated in a 100° C. oil bath for 24 h. After being cooled to room temperature, the reaction mixture was concentrated, and the residue was crystallized from hexane. The white crystalline material was collected by filtration and dried (1.7 g) to give major isomer of anti conformation. The mother liquor was concentrated and purified by column chromatography using 30% EtOAc in hexane as eluent to give a second batch of 102b (0.8 g). Total yield: 83%. 102b-syn; mp>300° C.; $^1$H NMR (300 MHz, CDCl$_3$): δ 7.31 (dd, J=5.4 and 3.3 Hz, 4H), 7.04 (dd, J=5.4 and 3.3 Hz, 4H), 5.92 (s, 4H), 1.28 (s, 42H); HR-MS (EI) calcd. for C$_{52}$H$_{54}$F$_{12}$Si$_2$ (M$^+$): found: 962.3421. 102b-anti; mp>300° C.; $^1$H NMR (300 MHz, CDCl$_3$): δ 7.41 (dd, J=5.4 and 3.3 Hz, 4H), 7.14 (dd, J=5.4 and 3.3 Hz, 4H), 5.92 (s, 4H), 1.28 (s, 42H); HR-MS (EI) calcd. for C$_{52}$H$_{54}$F$_{12}$Si$_2$ (M$^+$): found: 962.3421.

EXAMPLE 40

Compound 103a

Tetrabutylammonium fluoride (1 M in THF; 0.015 mL, 0.146 mmol) was added to a stirred solution of 102a-anti (45 mg, 0.049 mmol) in THF (3 mL) at room temperature. The mixture was allowed to stir for 30 min at this temperature. The reaction mixture was concentrated in vacuo and the residue was passed through a short plug of silica. The crude product was crystallized from hexane and dichloromethane (10:1) to give 103a-anti as a white solid (27.5 mg, 92%): 103a-anti; mp>300° C.; $^1$H NMR (300 MHz, CDCl$_3$): δ7.42 (dd, J=5.4 and 3.3 Hz, 4H), 7.05 (dd, J=5.4 and 3.3 Hz, 4H), 5.89 (s, 4H), 3.75 (s, 12H), 3.67 (s, 2H); $^{13}$C NMR (75 MHz, CDCl$_3$): δ165.8, 147.2, 144.1, 143.4, 126.0, 124.4, 114.7, 85.7, 52.7, 50.9, HR-MS (EI) calcd. for C$_{38}$H$_{26}$O$_8$ (M$^+$): 610.16, found: 610.16. 103a-syn; mp>300° C.; $^1$H NMR (300 MHz, CDCl$_3$): δ7.37 (dd, J=5.4 and 3.0 Hz, 4H), 6.99 (dd, J=5.4 and 3.0 Hz, 4H), 5.89 (s, 4H), 3.81 (s, 12H), 3.67 (s, 2H); $^{13}$C NMR (75 MHz, CDCl$_3$): δ165.8, 147.2, 144.1, 143.4, 125.9, 124.4, 114.7, 85.7, 52.8, 50.9; HR-MS (EI) calcd. for C$_{38}$H$_{26}$O$_8$ (M$^+$): 610.16, found: 610.16.

Compound 103b

Tetrabutylammonium fluoride (1 M in THF; 1.56 mL, 1.56 mmol) was added to a stirred mixture solution of two isomer 102b (500 mg, 0.52 mmol) in THF (20 mL) at room temperature. The mixture was allowed to stir for 30 min at this temperature. The reaction mixture was concentrated in vacuo and the residue was passed through a short plug of silica. The crude product was concentrated and purified by column chromatography (10% EtOAc in hexane) to give 103b as a white solid mixture of two isomers (283 mg, 84%): 103b-anti; mp>300° C.; $^1$H NMR (300 MHz, CDCl$_3$): δ7.50 (dd, J=5.4 and 3.3 Hz, 4H), 7.15 (dd, J=5.4 and 3.3 Hz, 4H), 5.89 (s, 4H), 3.76 (s, 2H); $^{19}$F NMR (MHz, CDCl$_3$): δ–61.9; HR-MS (EI) calcd. for C$_{34}$H$_{14}$F$_{12}$ (M$^+$):650.09, found: 650.09. 103b-syn; mp>300° C.; $^1$H NMR (300 MHz, CDCl$_3$): δ7.41 (dd, J=5.4 and 3.3 Hz, 4H), 7.06 (dd, J=5.4 and 3.3 Hz, 4H), 5.89 (s, 4H), 3.76 (s, 2H); $^{19}$F NMR (MHz, CDCl$_3$): δ–61.7; HR-MS (EI) calcd. for C$_{34}$H$_{14}$F$_{12}$ (M$^+$): 650.09, found: 650.09.

EXAMPLE 41

Compound 104

A solution of C$_8$F$_{17}$I (18.2 g, 33 mmol) was added dropwise over 10 min to a stirred mixture of copper powder (4.3 g, 67.5 mmol) in dry DMSO (30 mL) at 140° C. After 45 min, 1,4-diiodobenzene (5.0 g, 15 mmol) was added and the mixture was stirred for 3 days at this temperature. After cooling to room temperature, aqueous ammonia (50 mL) was added and the supernatant was decanted. The solid lump was washed with several portions of aqueous ammonia. The lump was dissolved in boiling toluene (500 mL) and filtered, giving a light yellow filterate with a white precipitate. The mixture was cooled. The white precipitate was filtered, washed with toluene (2×100 mL) and methylene chloride (2×100 mL) and dried to give the product 104 as a white solid (2.7 g, 20%): $^1$H NMR (300 MHz, CDCl$_3$): δ7.77 (s, 4H); HR-MS (EI) calcd. for C$_{22}$H$_4$F$_{34}$ ([M]$^+$): 913.9765, found ([M]$^+$): 913.9738.

EXAMPLE 42

Compound 105

Into a 100 mL round-bottomed flask were placed 20 mL trifluoroacetic acid, compound 104 (300 mg, 0.328 mmol), and 6 mL sulfuric acid (98%). The mixture was stirred vigorously and NBS (175 mg, 0.984 mmol) was added in portions at 70° C. over a 5-hour period. After stirring at 70° C. for 2 d, the mixture was poured into 50 mL of ice-water. The precipitates were filtered and recrystallized from toluene to give a white solid 105 (88 mg, 25%): $^1$H NMR (300 MHz, CDCl$_3$): δ7.95 (s, 2H); HR-MS (EI) calcd. for C$_{22}$H$_2$F$_{34}$Br$_2$ ([M]$^+$): 1069.7975, found ([M]$^+$): 1069.7939.

EXAMPLE 43

Polymers A-D and G

A general procedure is illustrated by the synthesis of polymer A. Compound 103a (20 mg, 0.033 mmol), 1-perfluorooctyl-4-trifluoromethyl-2,5-dibromobenzene (23 mg, 0.032 mmol), CuI (0.36 mg, 0.002 mmol), and Pd(Ph$_3$)$_4$ (3.7 mg, 0.0032 mmol) were placed in a 25 ml Schlenk tube with a stir bar. The flask was evacuated and back-filled with argon three times, followed by the addition of diisopropylamine/toluene (1:2, 3 mL) under an atmosphere of argon. This mixture was heated at 70° C. for 3 days and then subjected to a CHCl$_3$/H$_2$O workup. The combined organic phase was washed with 10% NH$_4$Cl, and then dried (MgSO$_4$). The solvent was removed in vacuo, and the residue dissolved in chloroform was reprecipitated in methanol. The resulting precipitate was filtered and washed with MeOH and acetone to give a yellow solid (24 mg, 65%). Removal of oligomer and impurities was achieved by subjecting the solid to sequential extractions in Soxhlet extractor with MeOH, acetone, followed with chloroform. The chloroform fraction was characterized.

EXAMPLE 44

Polymers E-F

A general procedure is illustrated by the synthesis of polymer E. Compound 103a (25 mg, 0.041 mmol), pentiptycene quinone (24.5 mg, 0.053 mmol), CuI (2.4 mg, 0.012 mmol), and Pd(PPh$_3$)$_4$ (1.2 mg, 0.001 mmol) were combined under Ar in a 25-mL Schienk tube. To this were added 3 mL of toluene and 0.5 mL of diisopropylamine. The solution was stirred at 60° C. under Ar for 72 h. The reaction mixture was then cooled, taken up in 50 mL of chloroform, and extracted with a saturated aqueous ammonium chloride solution (3×40 mL). The organic phase was then dried (MgSO$_4$), and the solvent was removed under reduced pressure. This solid was redissolved in a minimum hot solvent and reprecipitated into methanol to give green solid. The solid was collected by filtration and washed repeatedly with hot methanol. Removal of oligomer and impurities was achieved by subjecting the solid to sequential extractions in Soxhlet extractor with MeOH, acetone, followed with chloroform. The chloroform fraction was characterized.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A fluorescent, semiconductive polymer comprising a conjugated backbone and electron withdrawing groups bonded to the polymer, wherein the fluorescent, semiconductive polymer is represented by formula Ia, Ib, Ic or Id:

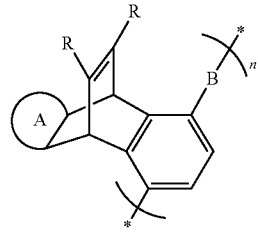

Ia

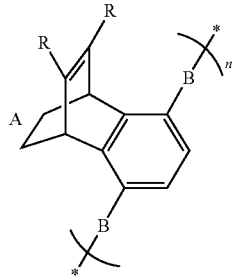

Ib

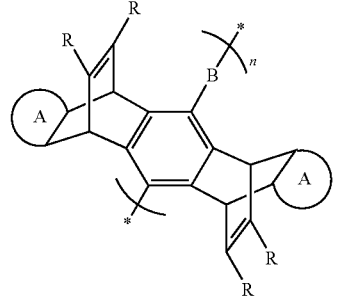

Ic

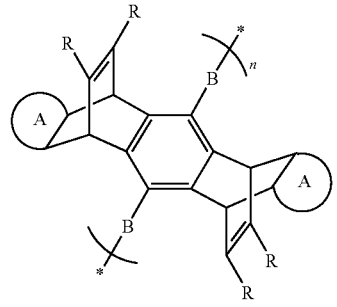

Id wherein, independently for each occurrence:
R is an electron withdrawing group selected from the group consisting of esters, perhalogenated alkyls, perhalogenated aryls, nitriles, and electron deficient heteroaryls;
B is a double bond, triple bond, or aryl; optionally substituted by one or more R$_1$;
R$_1$ is R, H, C$_{1-12}$ alkyl, C$_{2-12}$ alkenyl, C$_{2-12}$ alkynyl, aryl, aralkyl, heteroaryl, or heteroaralkyl;
A is a fused aryl, cycloalkyl, or cycloalkenyl ring;
* depicts an end group for the polymer selected from the group consisting of H, halide, alkyl, alkoxy, and aryl; and
n is an integer greater than 1.

2. The fluorescent, semiconductive polymer of claim 1, wherein R is an ester or a perhalogenated alkyl group.

3. The fluorescent, semiconductive polymer of claim 1, wherein R is an ester.

4. The fluorescent, semiconductive polymer of claim 1, wherein R is —CO$_2$CH$_3$ or —CO$_2$C(CH$_3$)$_3$.

5. The fluorescent, semiconductive polymer of claim 1, wherein R is a perfluorinated alkyl group.

6. The fluorescent, semiconductive polymer of claim 1, wherein R is a perfluorinated C$_{1-12}$ alkyl group.

7. The fluorescent, semiconductive polymer of claim 1, wherein R$_1$ is —CF$_3$, —C$_4$F$_9$, C$_8$F$_{17}$, or —C$_{10}$F$_{21}$.

8. The fluorescent, semiconductive polymer of claim 1, wherein R$_1$ is —CF$_3$.

9. The fluorescent, semiconductive polymer of claim 1, wherein R$_1$ is —C$_4$F$_9$.

10. The fluorescent, semiconductive polymer of claim 1, wherein R$_1$ is —C$_8$F$_{17}$.

11. The fluorescent, semiconductive polymer of claim 1, wherein R$_1$ is —C$_{10}$F$_{21}$.

12. The fluorescent, semiconductive polymer of claim 1, wherein R$_1$ is H.

13. The fluorescent, semiconductive polymer of claim 1, wherein A is a fused benzene ring.

14. The fluorescent, semiconductive polymer of claim 1, wherein n is greater than about 10, 100, or 1000.

15. The fluorescent, semiconductive polymer of claim 1, wherein R is —CO$_2$Me, R$_1$ is H, A is a fused benzene ring, and n is greater than about 10, 100, or 1000.

16. The fluorescent, semiconductive polymer of claim 1, wherein R is —CF$_3$, R$_1$ is H, A is a fused benzene ring, and n is greater than about 10, 100, or 1000.

17. A fluorescent, semiconductive polymer comprising a conjugated backbone and electron withdrawing groups bonded to the polymer, wherein the fluorescent, semiconductive polymer comprises formula II:

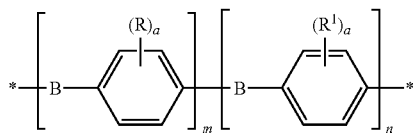

II wherein, independently for each occurrence:
B is a double bond, triple bond, or aryl;
R is an electron withdrawing group selected from the group consisting of esters, perhalogenated alkyls, perhalogenated aryls, nitriles, and electron deficient heteroaryls;
R$^1$ is R, H, C$_{1-6}$ alkyl, C$_{2-8}$ alkenyl, C$_{2-8}$ alkynyl, aryl, aralkyl, heteroaryl, heteroaralkyl, C$_{1-12}$ alkoxy, an electron deficient ring, or any two adjacent R$^1$ taken together form a monocyclic, bicyclic, tricyclic, or tetracyclic ring which may be substituted by one or more R;
* depicts an end group for the polymer selected from the group consisting of H, halide, alkyl, alkoxy, and aryl;
a is an integer from 1-4 inclusive; and
m and n are integers greater than or equal to one.

18. The fluorescent, semiconductive polymer of claim 17, wherein B is a double bond.

19. The fluorescent, semiconductive polymer of claim 17, wherein B is a triple bond.

20. The fluorescent, semiconductive polymer of claim 17, wherein B is aryl.

21. The fluorescent, semiconductive polymer of claim 17, wherein R is a perhalogenated alkyl.

22. The fluorescent, semiconductive polymer of claim 17, wherein R is a perfluorinated alkyl.

23. The fluorescent, semiconductive polymer of claim 17, wherein R is an ester.

24. The fluorescent, semiconductive polymer of claim 17, wherein R is —CO$_2$CH$_3$ or —CO$_2$C(CH$_3$)$_3$.

25. The fluorescent, semiconductive polymer of claim 17, wherein R is —CF$_3$, —C$_4$F$_9$, —C$_8$F$_{17}$, or —C$_{10}$F$_{21}$.

26. The fluorescent, semiconductive polymer of claim 17, wherein R is —CF$_3$.

27. The fluorescent, semiconductive polymer of claim 17, wherein R is —C$_4$F$_9$.

28. The fluorescent, semiconductive polymer of claim 17, wherein R is —C$_8$F$_{17}$.

29. The fluorescent, semiconductive polymer of claim 17, wherein R is —C$_{10}$F$_{21}$.

30. The fluorescent, semiconductive polymer of claim 17, wherein at least one R$^1$ is a perfluorinated C$_{1-12}$ alkyl.

31. The fluorescent, semiconductive polymer of claim 17, wherein two R$^1$ are perfluorinated C$_{1-12}$ alkyls.

32. The fluorescent, semiconductive polymer of claim 17, wherein at least one R$^1$ is a C$_{1-12}$ alkoxy group.

33. The fluorescent, semiconductive polymer of claim 17, wherein two R$^1$ are C$_{1-12}$ alkoxy groups.

34. The fluorescent, semiconductive polymer of claim 17, wherein a is 2.

35. The fluorescent, semiconductive polymer of claim 17, wherein m and n are greater than about 10, 100, or 1000.

36. The fluorescent, semiconductive polymer of claim 17, wherein two sets of adjacent R$^1$ each form a monocyclic ring.

37. The fluorescent, semiconductive polymer of claim 17, wherein two sets of adjacent R$^1$ each form a bicyclic ring.

38. The fluorescent, semiconductive polymer of claim 17, wherein two sets of adjacent R$^1$ each form a tricyclic ring.

39. The fluorescent, semiconductive polymer of claim 17, wherein two sets of adjacent R$^1$ each form a tetracyclic ring.

40. The fluorescent, semiconductive polymer of claim 17, wherein two sets of adjacent R$^1$ each form either a monocyclic, bicyclic, tricyclic, or tetracyclic structure.

41. The fluorescent, semiconductive polymer of claim 17, wherein two sets of R$^1$ are each independently selected from the group consisting of

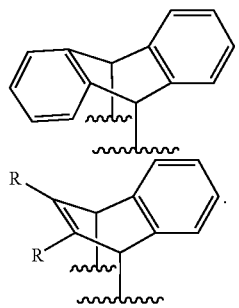

and

* * * * *

UNITED STATES PATENT AND TRADEMARK OFFICE
CERTIFICATE OF CORRECTION

PATENT NO. : 7,700,366 B2 Page 1 of 1
APPLICATION NO. : 11/005634
DATED : April 20, 2010
INVENTOR(S) : Timothy M. Swager and Youngmi Kim It is certified that error appears in the above-identified patent and that said Letters Patent is hereby corrected as shown below:

In column 1, at lines 14-18, please replace:
"This invention was made with support provided by the U.S. Army through the Institute for Soldier Nanotechnologies, under Contract DAAD-19-02-D-0002 with the U.S. Army Research Office; the government, therefore, has certain rights in the invention." with --This invention was made with government support under Grant Nos. DAAD19-01-1-0676 and DAAD19-02-D-0002, awarded by the ARO. The government has certain rights in this invention.--

Signed and Sealed this

Fourteenth Day of September, 2010

David J. Kappos
*Director of the United States Patent and Trademark Office*